(12) United States Patent
Evans et al.

(10) Patent No.: US 7,723,116 B2
(45) Date of Patent: *May 25, 2010

(54) APPARATUS, METHODS AND PROCESSES FOR SORTING PARTICLES AND FOR PROVIDING SEX-SORTED ANIMAL SPERM

(75) Inventors: Kenneth M. Evans, College Station, TX (US); Thomas B. Gilligan, Fort Collins, CO (US)

(73) Assignee: XY, Inc., Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/442,735

(22) Filed: May 25, 2006

(65) Prior Publication Data

US 2007/0117086 A1    May 24, 2007

Related U.S. Application Data

(63) Continuation of application No. 10/556,981, filed as application No. PCT/US2004/015457 on May 15, 2004.

(60) Provisional application No. 60/471,509, filed on May 15, 2003.

(51) Int. Cl.
    *G01N 33/48*    (2006.01)
    *G01N 21/64*    (2006.01)
    *C12Q 1/00*     (2006.01)
    *C12M 3/00*     (2006.01)

(52) U.S. Cl. .......................... 436/63; 436/55; 436/164; 436/172; 422/73; 422/82.05; 422/82.08; 435/4; 435/287.1

(58) Field of Classification Search .................. 436/63, 436/164, 165, 43, 50, 55, 172; 422/67, 68.1, 422/73, 82.05, 82.08; 435/2, 4, 287.1; 702/21
See application file for complete search history.

(56) References Cited

U.S. PATENT DOCUMENTS

| 3,005,756 A | 10/1961 | VanDemark et al. |
| 3,299,354 A | 1/1967  | Hogg |
| 3,499,435 A | 3/1970  | Rockwell et al. |
| 3,547,526 A | 12/1970 | Devereux |

(Continued)

FOREIGN PATENT DOCUMENTS

BR    9704313    6/1999

(Continued)

OTHER PUBLICATIONS

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

(Continued)

*Primary Examiner*—Maureen M Wallenhorst
(74) *Attorney, Agent, or Firm*—Cindee Ewell; Ryan Christensen

(57) ABSTRACT

A flow cytometry system (1) for sorting haploid cells, specifically irradiatable sperm cells, with an intermittingly punctuated radiation emitter (56). Embodiments include a beam manipulator (21) and even split radiation beams directed to multiple nozzles (5). Differentiation of sperm characteristics with increased resolution may efficiently allow differentiated sperm cells to be separated higher speeds and even into subpopulations having higher purity.

69 Claims, 16 Drawing Sheets

U.S. PATENT DOCUMENTS

| | | |
|---|---|---|
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Toboada et al. |
| 4,538,733 A | 9/1985 | Hoffman |
| 4,545,677 A | 10/1985 | Chupp |
| 4,559,309 A | 12/1985 | Evenson |
| 4,573,796 A * | 3/1986 | Martin et al. ............... 356/318 |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |

| | | | | | |
|---|---|---|---|---|---|
| 4,954,715 A | 9/1990 | Zold | 5,444,527 A | 8/1995 | Kosaka |
| 4,957,363 A | 9/1990 | Takeda et al. | 5,447,841 A | 9/1995 | Grey et al. |
| 4,959,354 A | 9/1990 | Barbetti | 5,447,842 A | 9/1995 | Simons |
| 4,965,204 A | 10/1990 | Civin | 5,452,054 A | 9/1995 | Dewa et al. |
| 4,979,093 A | 12/1990 | Laine et al. | 5,457,526 A | 10/1995 | Kosaka |
| 4,980,277 A | 12/1990 | Junilla | 5,461,145 A | 10/1995 | Kudo et al. |
| 4,981,580 A | 1/1991 | Auer | 5,464,581 A | 11/1995 | Van den Engh |
| 4,983,038 A | 1/1991 | Ohki et al. | 5,466,572 A | 11/1995 | Sasaki et al. |
| 4,987,539 A | 1/1991 | Moore et al. | 5,467,189 A | 11/1995 | Kreikebaum et al. |
| 4,988,619 A | 1/1991 | Pinkel | 5,469,375 A | 11/1995 | Kosaka |
| 4,989,977 A | 2/1991 | North, Jr. | 5,471,294 A | 11/1995 | Ogino |
| 4,999,283 A | 3/1991 | Zavos et al. | 5,471,299 A | 11/1995 | Kaye et al. |
| 5,005,981 A | 4/1991 | Schulte et al. | 5,475,487 A | 12/1995 | Mariella, Jr. et al. |
| 5,007,732 A | 4/1991 | Ohki et al. | 5,480,774 A | 1/1996 | Hew et al. |
| 5,017,497 A | 5/1991 | De Grooth | 5,480,775 A | 1/1996 | Ito et al. |
| 5,021,244 A | 6/1991 | Spaulding | 5,483,469 A | 1/1996 | Van den Engh et al. |
| 5,030,002 A | 7/1991 | North, Jr. | 5,488,469 A | 1/1996 | Yamamoto et al. |
| 5,034,613 A | 7/1991 | Denk et al. | 5,492,534 A | 2/1996 | Atheyde |
| 5,040,890 A | 8/1991 | North, Jr. | 5,494,795 A | 2/1996 | Guerry et al. |
| 5,043,591 A | 8/1991 | Ludlow et al. | 5,495,719 A | 3/1996 | Gray, Jr. |
| 5,055,393 A | 10/1991 | Kwoh et al. | 5,496,272 A | 3/1996 | Chung et al. |
| 5,057,413 A | 10/1991 | Terstappen et al. | 5,503,994 A | 4/1996 | Shear et al. |
| 5,072,382 A | 12/1991 | Kamentsky | 5,514,537 A | 5/1996 | Chandler |
| 5,076,472 A | 12/1991 | Gross et al. | 5,523,573 A | 6/1996 | Hanninen et al. |
| 5,079,959 A | 1/1992 | Miyake et al. | 5,532,155 A | 7/1996 | Ranoux |
| 5,084,004 A | 1/1992 | Ranoux | 5,547,849 A | 8/1996 | Baer et al. |
| 5,087,295 A | 2/1992 | Gross et al. | 5,548,395 A | 8/1996 | Kosaka |
| 5,088,816 A | 2/1992 | Tomioka et al. | 5,548,661 A | 8/1996 | Price et al. |
| 5,089,714 A | 2/1992 | Ludlow et al. | 5,550,058 A | 8/1996 | Corio et al. |
| 5,098,657 A | 3/1992 | Blackford et al. | 5,556,764 A | 9/1996 | Sizto et al. |
| 5,101,978 A | 4/1992 | Marcus | 5,558,998 A | 9/1996 | Hammond et al. |
| 5,116,125 A | 5/1992 | Rigler | 5,559,032 A | 9/1996 | Pomeroy et al. |
| 5,127,729 A | 7/1992 | Oetliker et al. | 5,578,449 A | 11/1996 | Frasch et al. |
| 5,132,548 A | 7/1992 | Borden et al. | 5,579,159 A | 11/1996 | Ito |
| 5,135,759 A | 8/1992 | Johnson | 5,584,982 A | 12/1996 | Dovichi et al. |
| 5,138,181 A | 8/1992 | Lefevre et al. | 5,589,457 A | 12/1996 | Wiltbank |
| 5,142,140 A | 8/1992 | Yamazaki et al. | 5,596,401 A | 1/1997 | Kusuzawa |
| 5,142,462 A | 8/1992 | Kashima | 5,601,234 A | 2/1997 | Larue |
| 5,144,224 A | 9/1992 | Larsen | 5,601,235 A | 2/1997 | Booker et al. |
| 5,150,313 A | 9/1992 | Van den Engh et al. | 5,601,533 A | 2/1997 | Hancke et al. |
| 5,158,889 A | 10/1992 | Hirako et al. | 5,602,039 A | 2/1997 | Van den Engh |
| 5,159,397 A | 10/1992 | Kosaka et al. | 5,602,349 A | 2/1997 | Van den Engh |
| 5,159,403 A | 10/1992 | Kosaka | 5,608,519 A | 3/1997 | Gourley et al. |
| 5,162,306 A | 11/1992 | Donaldson | 5,620,842 A | 4/1997 | Davis et al. |
| 5,167,926 A | 12/1992 | Kimura et al. | 5,622,820 A | 4/1997 | Rossi |
| 5,180,065 A | 1/1993 | Touge et al. | 5,627,037 A | 5/1997 | Ward et al. |
| 5,182,617 A | 1/1993 | Yoneyama et al. | 5,633,503 A | 5/1997 | Kosaka |
| 5,195,979 A | 3/1993 | Schinkel et al. | 5,641,457 A | 6/1997 | Vardanega |
| 5,199,576 A | 4/1993 | Corio et al. | 5,643,796 A | 7/1997 | Van Den Engh et al. |
| 5,204,884 A | 4/1993 | Leary et al. | 5,650,847 A | 7/1997 | Maltsev et al. |
| 5,215,376 A | 6/1993 | Schulte et al. | 5,658,751 A | 8/1997 | Yue et al. |
| 5,219,729 A | 6/1993 | Hodgen | 5,660,997 A | 8/1997 | Spaulding |
| 5,247,339 A | 9/1993 | Ogino | 5,663,048 A | 9/1997 | Winkfein et al. |
| 5,259,593 A | 11/1993 | Orme et al. | 5,665,315 A | 9/1997 | Robert et al. |
| 5,260,764 A | 11/1993 | Fukuda et al. | 5,672,880 A | 9/1997 | Kain |
| 5,274,240 A | 12/1993 | Mathies et al. | 5,674,743 A | 10/1997 | Ulmer |
| 5,275,787 A | 1/1994 | Yuguchi et al. | 5,675,401 A | 10/1997 | Wangler et al. |
| 5,298,967 A | 3/1994 | Wells | 5,682,038 A | 10/1997 | Hoffman |
| 5,315,122 A | 5/1994 | Pinsky et al. | 5,684,575 A | 11/1997 | Steen |
| 5,316,540 A | 5/1994 | McMannis et al. | 5,687,727 A | 11/1997 | Kraus et al. |
| 5,317,162 A | 5/1994 | Pinsky et al. | 5,690,815 A | 11/1997 | Krasnoff et al. |
| 5,346,990 A | 9/1994 | Spaulding | 5,690,895 A | 11/1997 | Matsumoto et al. |
| RE34,782 E | 11/1994 | Dandliker et al. | 5,691,133 A | 11/1997 | Critser et al. |
| 5,359,907 A | 11/1994 | Baker et al. | 5,693,534 A | 12/1997 | Alak et al. |
| 5,366,888 A | 11/1994 | Fry et al. | 5,696,157 A | 12/1997 | Wang et al. |
| 5,367,474 A | 11/1994 | Auer et al. | 5,700,692 A | 12/1997 | Sweet |
| 5,370,842 A | 12/1994 | Miyazaki et al. | 5,701,012 A | 12/1997 | Ho |
| 5,371,585 A | 12/1994 | Morgan et al. | 5,707,808 A | 1/1998 | Roslaniec et al. |
| 5,395,588 A | 3/1995 | North, Jr. et al. | 5,708,868 A | 1/1998 | Ishikawa |
| 5,400,179 A | 3/1995 | Ito | 5,712,807 A | 1/1998 | Bangham |
| 5,412,466 A | 5/1995 | Ogino | 5,719,666 A | 2/1998 | Fukuda et al. |
| 5,437,987 A | 8/1995 | Ten et al. | 5,719,667 A | 2/1998 | Miers |
| 5,439,362 A | 8/1995 | Spaulding | 5,726,009 A | 3/1998 | Connors et al. |

| | | | | | |
|---|---|---|---|---|---|
| 5,726,364 A | 3/1998 | Van den Engh | 6,130,034 A | 10/2000 | Aitken |
| 5,726,751 A | 3/1998 | Altendorf et al. | 6,132,961 A | 10/2000 | Gray et al. |
| 5,730,941 A | 3/1998 | Lefevre et al. | 6,133,044 A | 10/2000 | Van den Engh |
| 5,736,330 A | 4/1998 | Fulton | 6,133,995 A | 10/2000 | Kubota |
| 5,739,902 A | 4/1998 | Gjelsnes et al. | 6,139,800 A | 10/2000 | Chandler |
| 5,745,308 A | 4/1998 | Spangenberg | 6,140,121 A | 10/2000 | Ellington et al. |
| 5,747,349 A | 5/1998 | den Engh et al. | 6,143,535 A | 11/2000 | Paisson |
| 5,759,767 A | 6/1998 | Lakowicz et al. | 6,143,901 A | 11/2000 | Dervan |
| 5,777,732 A | 7/1998 | Hanninen et al. | 6,146,837 A | 11/2000 | van de Winkel |
| 5,780,230 A | 7/1998 | Li et al. | 6,149,867 A | 11/2000 | Seidel et al. |
| 5,786,560 A | 7/1998 | Tatah et al. | 6,153,373 A | 11/2000 | Benjamin et al. |
| 5,790,692 A | 8/1998 | Price et al. | 6,154,276 A | 11/2000 | Mariella, Jr. |
| 5,793,485 A | 8/1998 | Gourley | 6,175,409 B1 | 1/2001 | Nielsen et al. |
| 5,796,112 A | 8/1998 | Ichie | 6,177,277 B1 | 1/2001 | Soini |
| 5,798,276 A | 8/1998 | Haugland et al. | 6,193,647 B1 | 2/2001 | Beebe et al. |
| 5,799,830 A | 9/1998 | Carroll et al. | 6,201,628 B1 | 3/2001 | Basiji et al. |
| 5,804,436 A | 9/1998 | Okun et al. | 6,207,392 B1 | 3/2001 | Weiss et al. |
| 5,815,262 A | 9/1998 | Schrof et al. | 6,208,411 B1 | 3/2001 | Vaez-Iravani |
| 5,819,948 A | 10/1998 | Van den Engh | 6,211,477 B1 | 4/2001 | Cardott et al. |
| 5,824,269 A | 10/1998 | Kosaka et al. | 6,214,560 B1 | 4/2001 | Yguerabide et al. |
| 5,831,723 A | 11/1998 | Kubota et al. | 6,221,654 B1 | 4/2001 | Quake et al. |
| 5,835,262 A | 11/1998 | Iketaki et al. | 6,221,671 B1 | 4/2001 | Groner et al. |
| 5,840,504 A | 11/1998 | Blecher | 6,238,920 B1 | 5/2001 | Nagai et al. |
| 5,844,685 A | 12/1998 | Gontin | 6,247,323 B1 | 6/2001 | Maeda |
| 5,846,737 A | 12/1998 | Kang | 6,248,590 B1 | 6/2001 | Malachowski |
| 5,866,344 A | 2/1999 | Georgiou | 6,256,096 B1 | 7/2001 | Johnson |
| 5,868,767 A | 2/1999 | Farley et al. | 6,263,745 B1 | 7/2001 | Buchanan et al. |
| 5,872,627 A | 2/1999 | Miers | 6,283,920 B1 | 9/2001 | Eberle et al. |
| 5,873,254 A | 2/1999 | Arav | 6,296,810 B1 | 10/2001 | Ulmer |
| 5,874,266 A | 2/1999 | Paisson | 6,309,815 B1 | 10/2001 | Tash et al. |
| 5,876,942 A | 3/1999 | Cheng et al. | 6,316,234 B1 | 11/2001 | Bova |
| 5,880,457 A | 3/1999 | Tomiyama et al. | 6,317,511 B1 | 11/2001 | Horiuchi |
| 5,880,474 A | 3/1999 | Norton et al. | 6,322,901 B1 | 11/2001 | Bawendi et al. |
| 5,883,378 A | 3/1999 | Irish et al. | 6,323,632 B1 | 11/2001 | Husher et al. |
| 5,888,730 A | 3/1999 | Gray et al. | 6,326,144 B1 | 12/2001 | Bawendi et al. |
| 5,891,734 A | 4/1999 | Gill et al. | 6,328,071 B1 | 12/2001 | Austin |
| 5,893,843 A | 4/1999 | Rodrigues Claro | 6,329,158 B1 | 12/2001 | Hoffman et al. |
| 5,895,764 A | 4/1999 | Sklar et al. | 6,332,540 B1 | 12/2001 | Paul et al. |
| 5,895,922 A | 4/1999 | Ho | 6,357,307 B2 | 3/2002 | Buchanan et al. |
| 5,899,848 A | 5/1999 | Haubrich | 6,368,786 B1 | 4/2002 | Saint-Ramon et al. |
| 5,909,278 A | 6/1999 | Deka et al. | 6,372,422 B1 | 4/2002 | Seidel et al. |
| 5,912,257 A | 6/1999 | Prasad et al. | 6,372,506 B1 | 4/2002 | Norton |
| 5,916,144 A | 6/1999 | Prather et al. | 6,384,951 B1 | 5/2002 | Basiji et al. |
| 5,916,449 A | 6/1999 | Ellwart et al. | 6,395,305 B1 | 5/2002 | Buhr et al. |
| 5,917,733 A | 6/1999 | Bangham | 6,411,904 B1 | 5/2002 | Chandler |
| 5,919,360 A | 7/1999 | Contaxis, III et al. | 6,400,453 B1 | 6/2002 | Hansen |
| 5,919,621 A | 7/1999 | Brown | 6,411,835 B1 | 6/2002 | Modell et al. |
| 5,934,885 A | 8/1999 | Farrell et al. | 6,416,190 B1 | 7/2002 | Grier et al. |
| 5,962,238 A | 10/1999 | Sizto et al. | 6,423,505 B1 | 7/2002 | Davis |
| 5,972,710 A | 10/1999 | Weigl et al. | 6,423,551 B1 | 7/2002 | Weiss et al. |
| 5,973,842 A | 10/1999 | Spangenberg | 6,432,638 B2 | 8/2002 | Dervan et al. |
| 5,985,216 A | 11/1999 | Rens et al. | 6,452,372 B1 | 9/2002 | Husher et al. |
| 5,985,538 A | 11/1999 | Stachecju | 6,454,945 B1 | 9/2002 | Weigl et al. |
| 5,990,479 A | 11/1999 | Weiss et al. | 6,456,055 B2 | 9/2002 | Shinabe et al. |
| 5,991,028 A | 11/1999 | Cabib et al. | 6,463,314 B1 | 10/2002 | Haruna |
| 5,998,140 A | 12/1999 | Dervan et al. | 6,465,169 B2 | 10/2002 | Walderich et al. |
| 5,998,212 A | 12/1999 | Corio et al. | 6,473,176 B2 | 10/2002 | Basiji et al. |
| 6,002,471 A | 12/1999 | Quake | 6,482,652 B2 | 11/2002 | Furlong et al. |
| 6,003,678 A | 12/1999 | Van den Engh | 6,489,092 B1 | 12/2002 | Benjamin et al. |
| 6,042,025 A | 3/2000 | Crampton et al. | 6,495,333 B1 | 12/2002 | Willmann et al. |
| 6,042,249 A | 3/2000 | Spangenberg | 6,495,366 B1 | 12/2002 | Briggs |
| 6,050,935 A | 4/2000 | Ranoux et al. | 6,503,698 B1 | 1/2003 | Dobrinsky et al. |
| 6,071,689 A | 6/2000 | Seidel et al. | 6,511,853 B1 | 1/2003 | Kopf-Sill et al. |
| 6,079,836 A | 6/2000 | Burr et al. | 6,514,722 B2 | 2/2003 | Paisson et al. |
| 6,086,574 A | 7/2000 | Carroll et al. | 6,524,860 B1 | 2/2003 | Seidel et al. |
| 6,087,352 A | 7/2000 | Trout | 6,528,802 B1 | 3/2003 | Karsten et al. |
| 6,090,947 A | 7/2000 | Dervan et al. | 6,534,308 B1 | 3/2003 | Palsson et al. |
| 6,097,485 A | 8/2000 | Lievan | 6,537,829 B1 | 3/2003 | Zarling et al. |
| 6,111,398 A | 8/2000 | Graham | 6,540,895 B1 | 4/2003 | Spence et al. |
| 6,117,068 A | 9/2000 | Gourley et al. | 6,563,583 B2 | 5/2003 | Ortyn et al. |
| 6,119,465 A | 9/2000 | Mullens et al. | 6,576,291 B2 | 6/2003 | Bawendi et al. |
| 6,120,735 A | 9/2000 | Zborowski et al. | 6,577,387 B2 | 6/2003 | Ross, III et al. |
| 6,128,133 A | 10/2000 | Bergmann | 6,580,504 B1 | 6/2003 | Ortyn et al. |

| | | |
|---|---|---|
| 6,587,203 B2 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,704,313 B1 | 3/2004 | Duret et al. |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 4/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,759 B2 | 9/2004 | Heldt |
| 6,793,387 B1 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozeboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 * | 9/2006 | Kurabayashi et al. ........ 436/165 |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Asbury et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0002027 A1 * | 1/2003 | Fritz ............................. 356/39 |
| 2003/0129091 A1 | 1/2003 | Seidel et al. |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0113765 A1 | 6/2003 | Dempcy et al. |
| 2003/0119050 A1 | 6/2003 | Shai |
| 2003/0119206 A1 | 6/2003 | Shai |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0098421 A1 | 11/2003 | Ho |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0107150 A1 | 6/2004 | Neas et al. |
| 2004/0132001 A1 | 7/2004 | Seidel et al. |
| 2005/0003472 A1 | 1/2005 | Muhammad |
| 2005/0011582 A1 | 1/2005 | Haug |
| 2005/0064383 A1 | 3/2005 | Bashkin et al. |
| 2005/0112541 A1 | 5/2005 | Durack |
| 2005/0214733 A1 | 9/2005 | Graham et al. |
| 2005/0244805 A1 | 11/2005 | Ludwig et al. |
| 2005/0028224 A1 | 12/2005 | Ludwig et al. |
| 2005/0282245 A1 | 12/2005 | Ludwig et al. |
| 2006/0067916 A1 * | 3/2006 | Schenk et al. ............... 424/93.7 |
| 2006/0118167 A1 | 6/2006 | Neas et al. |
| 2006/0147894 A1 | 7/2006 | Sowter |
| 2006/0263829 A1 | 11/2006 | Evans et al. |
| 2006/0281176 A1 | 12/2006 | Seidel et al. |
| 2007/0017086 A1 | 1/2007 | McFadyen |
| 2007/0026378 A1 | 2/2007 | Schenk |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0099171 A1 | 5/2007 | Schenk |
| 2007/0099260 A1 | 5/2007 | Seidel et al. |

FOREIGN PATENT DOCUMENTS

| | | |
|---|---|---|
| CA | 1029833 | 4/1978 |
| CA | 1 250 808 | 3/1989 |
| CA | 2113957 A1 | 1/1994 |
| CN | 03109426.0 | 12/2005 |
| CN | 100998524 | 9/2007 |
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0 046 345 A2 | 2/1982 |
| EP | 0 068 404 B1 | 1/1983 |
| EP | 0071538 A1 | 2/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |

| | | | | | | |
|---|---|---|---|---|---|---|
| EP | 0468100 A1 | 1/1992 | | SU | 1260778 A1 | 9/1986 |
| EP | 0474 187 A2 | 3/1992 | | WO | WO 84/01265 A1 | 4/1984 |
| EP | 0 316 172 B1 | 7/1992 | | WO | WO 85/04014 A1 | 9/1985 |
| EP | 0 316 171 B1 | 9/1992 | | WO | WO 88/07198 | 9/1988 |
| EP | 0570102 A1 | 3/1993 | | WO | WO 89/04470 A1 | 5/1989 |
| EP | 0 538 786 A | 4/1993 | | WO | WO 89/04471 A1 | 5/1989 |
| EP | 0 279 000 B1 | 7/1993 | | WO | WO 90/13315 A1 | 11/1990 |
| EP | 0 553 951 A1 | 8/1993 | | WO | 9105236 | 4/1991 |
| EP | 0 288 029 B1 | 1/1994 | | WO | WO 92/08120 A1 | 5/1992 |
| EP | 0 381 694 B1 | 6/1994 | | WO | WO 92/17288 A1 | 10/1992 |
| EP | 0 361 504 B1 | 7/1994 | | WO | WO 93/10803 | 6/1993 |
| EP | 606847 A2 | 7/1994 | | WO | 9317322 A1 | 9/1993 |
| EP | 0 289 200 B2 | 8/1994 | | WO | WO 94/22001 A1 | 9/1994 |
| EP | 0 555 212 B1 | 10/1994 | | WO | WO 96/04542 A1 | 2/1996 |
| EP | 0 361 503 B1 | 11/1994 | | WO | WO 96/12171 A2 | 4/1996 |
| EP | 0 696 731 A2 | 2/1996 | | WO | WO 96/12172 | 4/1996 |
| EP | 0 705 978 A2 | 4/1996 | | WO | WO 96/12173 A1 | 4/1996 |
| EP | 0 711 991 A1 | 5/1996 | | WO | WO 96/31764 | 10/1996 |
| EP | 0 471 758 B1 | 9/1996 | | WO | WO 96/33806 A1 | 10/1996 |
| EP | 0 736 765 A1 | 10/1996 | | WO | WO 97/29354 A1 | 8/1997 |
| EP | 0 545 284 B1 | 2/1997 | | WO | WO 97/30338 A1 | 8/1997 |
| EP | 0 360 487 B1 | 7/1997 | | WO | WO 97/35189 A1 | 9/1997 |
| EP | 0 412 431 B1 | 10/1997 | | WO | WO 97/43620 A1 | 11/1997 |
| EP | 0 526 131 B1 | 1/1998 | | WO | WO 89/04472 A1 | 5/1998 |
| EP | A-0 478155 | 1/1998 | | WO | WO 98/34094 A1 | 8/1998 |
| EP | 0 822 404 A3 | 2/1998 | | WO | WO 98/48259 | 10/1998 |
| EP | 0 822 401 A2 | 4/1998 | | WO | WO 98/57152 A1 | 12/1998 |
| EP | 0781985 A3 | 7/1998 | | WO | WO 99/05504 A2 | 2/1999 |
| EP | 0 556 748 B1 | 10/1998 | | WO | WO 99/33956 A1 | 7/1999 |
| EP | 0 430 402 B1 | 1/1999 | | WO | WO 99/38883 A1 | 8/1999 |
| EP | 0 529 666 B1 | 4/2000 | | WO | WO 99/42810 A1 | 8/1999 |
| EP | 0 994 342 A3 | 4/2000 | | WO | WO 99/44035 | 9/1999 |
| EP | 0 752 133 B1 | 6/2000 | | WO | WO 99/44037 A1 | 9/1999 |
| EP | 1 018 644 A2 | 7/2000 | | WO | WO 99/47906 A1 | 9/1999 |
| EP | 1 118 268 A1 | 7/2001 | | WO | WO 99/60397 A1 | 11/1999 |
| EP | 1 147 774 A1 | 10/2001 | | WO | WO 9957955 | 11/1999 |
| EP | 0 534 033 B1 | 11/2001 | | WO | WO 99/61888 A2 | 12/1999 |
| EP | 0 925 494 B1 | 12/2001 | | WO | WO 00/06193 A1 | 2/2000 |
| EP | 0 748 316 B1 | 5/2002 | | WO | WO 00/12204 | 3/2000 |
| EP | 0 662 124 B1 | 6/2002 | | WO | WO 00/36396 | 6/2000 |
| EP | 1 245 944 A3 | 10/2002 | | WO | WO 00/49387 | 8/2000 |
| EP | 1 249 502 A2 | 10/2002 | | WO | WO 00/54026 | 9/2000 |
| EP | 1250897 A1 | 10/2002 | | WO | WO 00/56444 | 9/2000 |
| EP | 1 380 304 A2 | 1/2004 | | WO | WO 00/70080 | 11/2000 |
| EP | 1 403 633 A3 | 4/2004 | | WO | WO 01/02836 A1 | 1/2001 |
| EP | 1 100 400 B1 | 5/2004 | | WO | 01/29538 * | 4/2001 |
| EP | 1 257 168 B1 | 2/2005 | | WO | WO 01/28700 A1 | 4/2001 |
| FR | 2574656 A1 | 6/1986 | | WO | WO 01/37655 A1 | 5/2001 |
| FR | A-2 635453 | 2/1990 | | WO | WO 01/40765 A2 | 6/2001 |
| FR | 2 647 668 A | 12/1990 | | WO | WO 01/40765 A3 | 6/2001 |
| FR | 2699678 A1 | 6/1994 | | WO | WO 01/42757 A2 | 6/2001 |
| GB | 1471019 | 4/1977 | | WO | WO 01/51612 A1 | 7/2001 |
| GB | 2 121 976 A | 1/1984 | | WO | WO 01/61313 A2 | 8/2001 |
| GB | 2 122 369 A | 1/1984 | | WO | WO 01/68110 | 9/2001 |
| GB | 2 125 181 A | 2/1984 | | WO | WO 01/68226 A2 | 9/2001 |
| GB | 2 136 561 A | 9/1984 | | WO | WO 01/71348 A1 | 9/2001 |
| GB | 2 137 352 A | 10/1984 | | WO | WO 01/75161 A2 | 10/2001 |
| GB | 2145112 | 2/1985 | | WO | WO 0175176 | 10/2001 |
| GB | 2 144 542 A | 3/1985 | | WO | 2002041906 A2 | 11/2001 |
| GB | 2 153 521 A | 8/1985 | | WO | WO 01/85913 A2 | 11/2001 |
| GB | 2 243 681 A | 11/1991 | | WO | WO 01/85913 A3 | 11/2001 |
| GB | 0030480.1 | 1/2001 | | WO | WO 01/90295 A1 | 11/2001 |
| GB | 2 360 360 A | 9/2001 | | WO | WO 01/95815 A1 | 12/2001 |
| JP | 61139747 A | 6/1986 | | WO | WO 02/01189 A1 | 1/2002 |
| JP | 61159135 A | 7/1986 | | WO | WO 02/04666 A1 | 1/2002 |
| JP | 2024535 | 1/1990 | | WO | WO 02/19594 | 3/2002 |
| JP | 4126064 A | 4/1992 | | WO | WO 02/19943 A1 | 3/2002 |
| JP | 4126065 A | 4/1992 | | WO | WO 02/20850 A2 | 3/2002 |
| JP | 4126066 A | 4/1992 | | WO | WO 02/21102 A2 | 3/2002 |
| JP | 4126079 A | 4/1992 | | WO | WO 02/23163 A1 | 3/2002 |
| JP | 4126080 A | 4/1992 | | WO | WO 02/25269 A2 | 3/2002 |
| JP | 4126081 A | 4/1992 | | WO | WO 02/26114 A2 | 4/2002 |
| SU | 1056008 | 11/1983 | | WO | WO 02/28311 A2 | 4/2002 |

| | | |
|---|---|---|
| WO | WO 02/29106 A2 | 4/2002 |
| WO | 02041906 A2 | 5/2002 |
| WO | WO 02/41906 A2 | 5/2002 |
| WO | WO 02/43486 A1 | 6/2002 |
| WO | WO 02/43574 A2 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | 03020877 A2 | 8/2002 |
| WO | WO 02/060880 A1 | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | 03020877 A2 | 3/2003 |
| WO | WO 03/056330 A2 | 7/2003 |
| WO | WO 03/056335 A2 | 7/2003 |
| WO | WO 03/ 072765 A1 | 9/2003 |
| WO | WO 03/078065 A1 | 9/2003 |
| WO | WO 03/078972 A1 | 9/2003 |
| WO | WO2004001401 | 12/2003 |
| WO | WO 2004/006916 A1 | 1/2004 |
| WO | WO 2004/009237 A1 | 1/2004 |
| WO | WO 2004/012837 A1 | 2/2004 |
| WO | WO 2004/012837 A3 | 2/2004 |
| WO | WO 2004/017041 A1 | 2/2004 |
| WO | WO 2004/017041 A3 | 2/2004 |
| WO | WO 2004/024227 A1 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A1 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | 2006012597 A2 | 2/2006 |
| WO | WO 2006/015056 A2 | 2/2006 |
| WO | 2006060770 A2 | 8/2006 |
| WO | 2007016090 A2 | 2/2007 |

OTHER PUBLICATIONS

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2)106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D., et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Toni and Currin, John Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $IN Asia B. Japan; www.agnet.org/library/article/eb384b.html.

Crichton,E. et al., J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H., et al.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R. P., et al. "Prospects for Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Baker, R.D., et al., "Effect of Volume of Semen, Number of Sperm and Drugs on Transport of Sperm in Artificially Inseminated Gilts", J. Anim. Sci. 27:88-93. (1968).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).

Bedford, S .J. and Hinrichs, K., "The Effect of Insemination Volume on Pregnancy Rates of Pony Mares", Therio. 42:571-578. (1994).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., et al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Borini et al. Cryopreservation of Mature Oocytes: The use of a trypsin inhibitor enhances fertilization and obtained embryos rates, Fertil. Steril. (1997), vol. 68 (Suppl.).

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef -Production III. Culling Strategies and Nontraditional Management-Systems", J. Anim. Sci. 65:963. 1987.

Bracher, V. and Allen, W.R., "Videoendoscopic Examination of the Mare's Uterus: I. Findings in Normal Fertile Mares", Equine Veterinary Journal, vol. 24, p. 274-278. 1992.

Branscomb, D. P., The LLNL high-speed sorter: Design features,operational characteristics, and bioloical utility, Cyometry, 6:290-301 (1985).

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice vol. 8 No. 1 Apr. 1992 pp. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriogenology p. 395.

Burns, P. D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

*Celestron: Telescope Basics*: www.celestron.com/tb-2ref/htm; 4 pages.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273. 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran et al. The predetermination of embryonic sex using flow cytometrically separated X and Y spermatozoa, Human Reproduction Update 1996, vol. 2, No. 4 pp. 355-363.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-363.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-169.

da Silva, Coutinho M.A.." Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

*DakoCytomation, "MoFlo® Sorters"* http://www.dakocvtomation.us/prod_productrelatedinformation?url=gprod_moflo_index.htm one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al:" Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Dhali et al. Vitrification of Buffalo (Bubalus Bubalis)Oocytes, Embryo Theriogenology vol. 53, pp. 1295-1303 (2000).

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y-Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing☐Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper -Mayer".

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. ABSTRACT.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117(1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu Photonics K.K. Electronic Tube Center, Photomultiplier Tubes, Brochure Dec. 1997.

Hamamatsu, "*Photomultiplier Tubes.*" web page, http://www.optics.org/hamamatsu/pmt.html. Printed on Apr. 15, 2000 4.

Hamamatsu. "*Technical Information. Optical Detector Selection: A Delicate Balancing Act*", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology , vol. 59. (2003) pp. 209.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine."

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) The Early Calving of Heifers and its Impact on Beef Production. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-660.

Johnson, A. L. "Pulsatile Administration of Gonadotropin Releasing Hormone Advances Ovulation in Cycling Mares", Biol. Reprod. 35:1123—1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.

Johnson, L.A., "Flow Cytometric Determination of Spermatozoa Sex Ratio in Semen Purportedly Enriched for X or Y Bearing Spermatozoa", Therio. 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al. "Sex Preselection: High-speed Flow Cytometric Sorting of X and Y Sperm for Maximum Efficiency", Therio. vol. 52, p. 1323-1341 (1999).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for DNA Using an Improved Preparation Method and Staining with Hoechst 33342." Gamete Research 17: 203-212. (1987).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) The Early Calving of Heifers and its Impact on Beef Production. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in Glycoprotein Hormones Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-289 (2001).

Lindsey, A., et al., "Hysteroscopic Insemination of Mares with Nonfrozen Low-dose Unsexed or Sex-sorted Spermatozoa", pp. 1-15 currently unpublished.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy,".

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) The Early Calving of Heifers and its Impact on Beef Production. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. Equine Reproduction. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548.

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49:1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;l. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121.

Parrish, J. J., et al., "Capacitation of Bovine Sperm by Heparin", Department of Meat and Animal Science, Biology of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M. et at., "Comparative Motility of X and Y Chromosome-Bearing Bovine Sperm Separated on the Basis of DNA Content", Mol. Reprod. And Develop. 1998, vol. 50,pp323-327.

Perry, E. J., "Historical Background" the Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049—1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22, (1974).

Pinkel et al., "Flow Chambers and Sample Handling", Flow Cytometry: Instrumentation and Data Analysis, Van Dilla et al. (Eds. ), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, Naouka Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115-118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rens W., et al Slit-scan flow cytometry for consistent high resdolution DNA analysis of X- and Y- chromosome bearing sperm, Cytometry 25:191-199 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. " Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salemon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) ( 1961 & 1978 Combined) Chapters 16 and 17 are the complete article.

Schenk, J. L, et al., "Imminent Commercialization of Sexed Bovine Sperm", Proceedings, The Range Beef Cow Symposium XVL, p. 89-96 (1999).

Schenk, J. L. "Applying Semen Sexing Technology to the AI Industry", Proceedings of the 18th Technical Conference on Artificial insemination & Reproduction, 2000.

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination ", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Seidel, G. E. Jr et al., "Current Status of Sexing Mammalian Spermatozoa," Society for Reproduction and fertiity, pp. 733-743, 2002.

Seidel, G. E. Jr. "Cryopreservation of Equine Embryos" Veterinary Cliniics of North America: Equine Practice vol. 12, No. 1, Apr. 1996.

Seidel, G. E. Jr. " Sexing Bovine Sperm" The AABP Proceedings—vol. 34.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers Of Nonfrozen and Sexed Spermatozoa", Atlantic Breeders Cooperative, Therio. 48: pp. 1255-1264, (1997).

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Commercilizing Repreductive Biotechnology—The Approach used by XY, Inc.," Theriogenology, p. 5, 1999.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Seidel, G. E. Jr., "Status of Sexing Semen for Beef Cattle", Texas A & M University 45th Annual Beef Cattle Short Course and Trade Show Proceedings, Aug. 9-11, p. 11124-11127, (1999).

Seidel, G. E. Jr., Economics of Selecting for Sex: The Most Important Genetic Trait, Theriogenology 59, (2003), pp. 585-598.

Seidel, G. E. Jr., et al, "Insemination of Heifers With Very Low Numbers Of Frozen Spermatozoa", CSU, Atlantic Breeders Cooperative, Lancaster, PA, DUO Dairy, Loveland, CO, Jul. (1996).

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Sell, R. S., et al., "Single-calf Heifer Profitability Compared to Other North Dakota Beef Production Systems." Department of Ag. Eco., North Dakota State University, Ag. Econ. Rpt. 20.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry. vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

*Spectra Physics. The Solid State Laser Company, "Vangaurd 4 Watts of UV from a Quasi-CW, All Solid State Laser."* http://www.splasers.com/products/isl_products/vangaurd.html three pages, printed Nov. 14, 2002.

*Spectra-Physics Products, "Fcbar"* http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specra-physics.com.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37:1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp, 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." in: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dille et al. (Eds.), 1985, pp. 1-8.

Van Munster, E. B., "Geslachtsbepaling met interferometrie", Derde prijs NtvN-prijsyraag voor pas-gepromoveerden 65/4, (Sex Determination with Interferometry) p. 95-98 (1999).

Van Munster, E. B., et al, "Difference in Sperm Head Volume as a Theoretical Basis for Sorting X & Y-Bearing Spermatozoa: Potentials and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

van Munsterm, E. B. Interferometry in flor to sort unstained X- and Y-Chromosome-Bearing Bull Spermatozoa, Cytometry 47:192-199 (2002).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Infra Uterine Insemination Technique", Boar Semen Preservation IV, IVth International Conference on Boar Semen Preservation, Maryland, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservation of Spermatozoa and the Assessment of Their Post-Thawing Function," Reprod. Fertil. Dev. 7:871-891 (1995) Abstract.

Welch G., et al., 'Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Crybiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium und Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.nciferf.gov/ccr/flowcore/ndyag.htm, pp. 5, May 11, 2004.

NCI ETI Branch, Flow CytometryCore Laboratory, http://home.nciferf.gov/ccr/flowcore/Isrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilisation of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

U.S. Appl. No. 10/556,971, filed Nov. 15, 2005, which is a national phase of PCT/US2004/015457, filed May 15, 2004.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18 (2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (*bubalus bubalis*) following deposition of sexed spermatozoa near the utero tubal junction, Reproduction in Domestic Animals, vol. 40, No. 1, Feb. 2005 , pp. 73-75(3).

Dielemann, S.J., Superovulation in cattle: from understanding the biological mechanisms to genomics of the oocyte; 23rd Annual Meeting A.E.T.E.—Alghero; Sep. 2007.

Hasler, J. F., Factors influencing the success of embryo transfer in cattle; 23rd World Buiatrics Congress, Quebec, Canada Jul. 2004.

Mapletoft, R. J. et al., Superovulation in perspective, Bioniche Animal Health, Dec. 2002.

Monsanto- Pulse—U.S. Appl. No. 10/812,351, response filed Dec. 14, 2007.

U.S. Appl. No. 10/812,351, Response to Restictive Office Action filed Apr. 5, 2007.

U.S. Appl. No. 10/812,351, Office Action dated Jun. 15, 2007.

Bakst, Murray R. Fate of Fluorescent Stained Sperm following Insemination: New Light on Ovicucal Sperm Transport and Storage in the Turkey.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Arathy D.S., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81:1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times Al of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Parallel European Regional Application No. 04 749 513.0; Office action dated Jun. 4, 2008.

Parallel European Regional Application No. 04 749 513.0; Office action dated Aug. 7, 2007.

Parallel European Regional Application No. 04 749 513.0; Office action dated Sep. 29, 2006.

Parallel U.S. Appl. No. 10/556,981, Office action dated Sep. 19, 2008.

Parallel U.S. Appl. No. 10/821,351, Office action dated Mar. 3, 2008.

Parallel U.S. Appl. No. 10/821,351, Notice of Allowability dated Sep. 23, 2008.

Bakst, Murray R. Fate of Fluorescent Stained Sperm following Insemination: New Light on Ovicucal Sperm Transport and Storage in the Turkey, 1994.

Bahr, G.F. et al., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6), pp. 895-902.

BD LSR II Flow Cytometer, BD Biosciences Clontech Discovery labware Immunocytometry systems Pharmingen Jan. 28, 2004.

Bermudez, D. et al., The immediate effect of IR, laser radiation on rat, germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Sabuer K. et al."Effects of Angiotensin II on the Acrosome Reaction in Equine Spermatozoa" Journal of Reproduction and Fertility vol. 120, 2002 p. 135-142.

Brooks, D.E., Manipulation of Mammalian Gametes in Vitro, Biennial Report, Waite Agricultural Research Institute 1986-1989.

Bruemmer, J.E. et al., "Effect of Pyruvate on the Function of Stallion Spermatozoa Stored for up to 48 Hours", Journal of Animal Science 2002, vol. 80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825, (1997).

Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nonge.gsnu.ac.kr/~cspark/teaching/chap196.html Sep. 23, 2002.

Conover, J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques, "3rd Ed., Butterworths, pp. 192.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado, N. et al., Correlation between sperm membrane destabilization by heparin and aniline blue staining as membrane integrity index, Archives of Andrology 40:147-152 (1998).

Denniston, D.J. et al., "Effect of Antioxidants on the Motility and Viability of Cooled Stallion Spermatozoa", Journal Reproduction Supplement 56, 2001, pp. 121-126.

De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al. Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D. et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote, R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 (1994).

Pinkel, D. et al., Flow cytometry of mammalian sperm progress in DNA and morphology measurement, The Journal of Histochemical and Cytochemistry vol. 27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G. et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (*Oncorhynchus mykiss*)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62:143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 6, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al. Spermatozoa and Seminal Plasma, Reproduction in farm animals 7th edition, 2000.

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology, Mar. 28, 2003.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., " Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa l, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. And Develop., 2002,vol. 61(1), pp. 87-92.

Hacker-Klom, U.B., et al., Effect of doxorubicin and 4'-epidoxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi- CW Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish Al bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., a flow cytometric/ sorting method for sexing mammalian sperm validated by DNA analysis and live births, Cytometry, p. 42 of supplement, Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5° C, Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland, 1991.

Johnson, L., Separation of X and Y Chromosome-bearing mammalian sperm by DNA content cytometric analysis and sorting, US Department of Agriculture.

Johnson, M.,The Macromolecular Organization of membranes and its bearing on events leading up to Fertilization, Journal of Reproduction and Fertility (1975).

Johnson, L., Verified Sex Pre-Selection in Farm Animals.

Johnson, L., Progass towards achieving sex preselection in farm animals, USDA Agricultural Research Service, (1989).

Keeler, K. et al., Flow microfluorometric analysis of living spermatozoa stained with Hoechst 33342, J. Reprod.Fert. 68:205-212 (1983).

Keij, J. et al., High speed Photodamage cell sorting: An evaluation of the Zapper Prototype, Methods in cell Biology vol. 42, (1994).

Kirchhoff, C. et al., The Molecular biology of the sperm surface:Post-Testicular Membrane Remodelling, The Fate of the Male Germ Cell, (1997).

Krueger, C. et al.,Low dose Insemination in synchronized gilts, Theriogenology 52: 1363-1373 (1999).

Lahdetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B. et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J. et al., Orientation measurments of microsphere doublets and metaphase chromosomes in flow, Cytometry 7:575-581 (1986).

Luttmer, S. et al.,Examination of living and fixed gametes and early embryos stained with supravital fluorochromes (Hoechst 33342 and 3,3'-dihexyloxacarocyanine Iodide), Gamete Research 15:267-283 (1986).

Masaki, J. et al., Effect of bull seminal plasma on the membrane characteristics of boarepididymal spermatozoa.

Maxwell, W. et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K. et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M. et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A. et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/cjas01-045.htmI.

Moruzzi, J., Selecting a mammalian species for the separationof X- and Y- chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R&D Magazine, Dec. 2003: pp. 36-37 as currently presented on and printed from http;//www.rdmag.com 2 pgs.

Gwo-Bin, L. et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J. et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R. et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge.

Edited by Bell-Prince, C. , NFCR Newsletter, http://www.Is.Ianl.gov/NFCR/newsletter-Oc98/oct98.html Jan. 6, 2004.

Rasul, Z. et al., Changes in motion characteristics, plasma membrane integrity, and acrosome morphology during cryopreservation of buffalo spermatozoa, Journal of Andrology, vol. 22 No. 2, Mar. 4, 2001.

Rees, William A., et al,Betaine Can Eliminate the Base Pair Composition Dependence of DNA Melting; Biochemistry 1993, 32, pp. 137-144.

Rens, W. et al.,An X-Y paint set and sperm FISH protocol that can be used for validation of cattle sperm separation procedures, Journals of Reproduction and Fertility, 121: 541-546 (2001).

Reyes-Mereno, C. et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R. et al., Semen Quality test and their relationship to fertility, 4th National Association of Animal Breeders, (1972).

Salisbury, G.W.,et al."Preservation of Bovine Spermatozoa in Yolk-Citrate Diluent and Field Results from its Use", Journal of Dairy Science, 1941, vol. 24(11),pp. 905-910.

Schroter, S. et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library, 1988.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291(2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter Jan. 2, 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1987).

Thurston,L. et al., Identification of Amplified restriction fragment length polymorphism markers linked to genes controlling boar sperm viability following cryopreservation, Biology of Reproduction 66: 545-554 (2002).

Tone,S.et al., A method of vital staining of mouse eggs using Hoechst dye, Department of Developmental Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch,G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc. , Sex selection Procedure, http://www.xyinc.com/sex select.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic inseminatin of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1 . p. 369.

Palma, G. et al., Sperm Physiology: The Ability to Produce Embryos In Vitro using Semen from Bulls with a Low Non-Return Rate. Therio. p. 308.

Gottlinger, Christopher et al., Cell-Cooling in Flow Cytometry by Peltier Elements. Cytometry 7:295-297 (1986).

ABSTRACTS: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Staining and Flow Cytometry. J. of Andrology, vol. 18, No. 3 May/Jun. 1997.

Parallel U.S. Appl. No. 10/821,351, Office action dated Nov. 10, 2008.

Parallel New Zealand Application No. 564309; Office action dated Feb. 19, 2009.

Parallel New Zealand Application No. 564309; Office action dated Dec. 20, 2007.

Parallel New Zealand Application No. 544103; Office action dated Oct. 29, 2008.

Parallel Australia Application No. 2004225436, Office action dated Sep. 23, 2008.

International Application No. PCT/US04/15457, Search Report dated Feb. 25, 2005.

International Application No. PCT/US04/15457, Written Opinion dated Feb. 25, 2005.

International Application No. PCT/US04/15457, International Preliminary Report on Patentability dated Dec. 18, 2008.

Parallel Chinese Patent Application No. 200480014339.1, Apparent Decision of Grant dated Apr. 3, 2009 (no translation received).

Parallel European Patent Application No. 04 749 513.0; Notice of Grant dated Jul. 10, 2009.

Parallel Australian Patent Application No. 2004225436, Office action dated Sep. 15, 2009.

Parallel Argentina Patent Application No. P 04 01 01044; Translated portion of Office Action dated Oct. 16, 2009.

Parallel New Zealand Patent Application No. 564309; Notice of acceptance dated Jul. 3, 2009.

Parallel New Zealand Patent Application No. 577678; Office Action dated Jun. 22, 2009.

Parallel New Zealand Patent Application No. 544103; Office Action dated Sep. 30, 2009.

Parallel Australian Patent Application No. 2004242121, Office action dated Apr. 22, 2009.

Parallel U.S. Appl. No. 10/812,351, Office action dated Jul. 23, 2009.

Parallel U.S. Appl. No. 12/404,931, Office action dated Jul. 23, 2009.

Parallel U.S. Appl. No. 10/556,981, Office action dated Jul. 9, 2009.

* cited by examiner

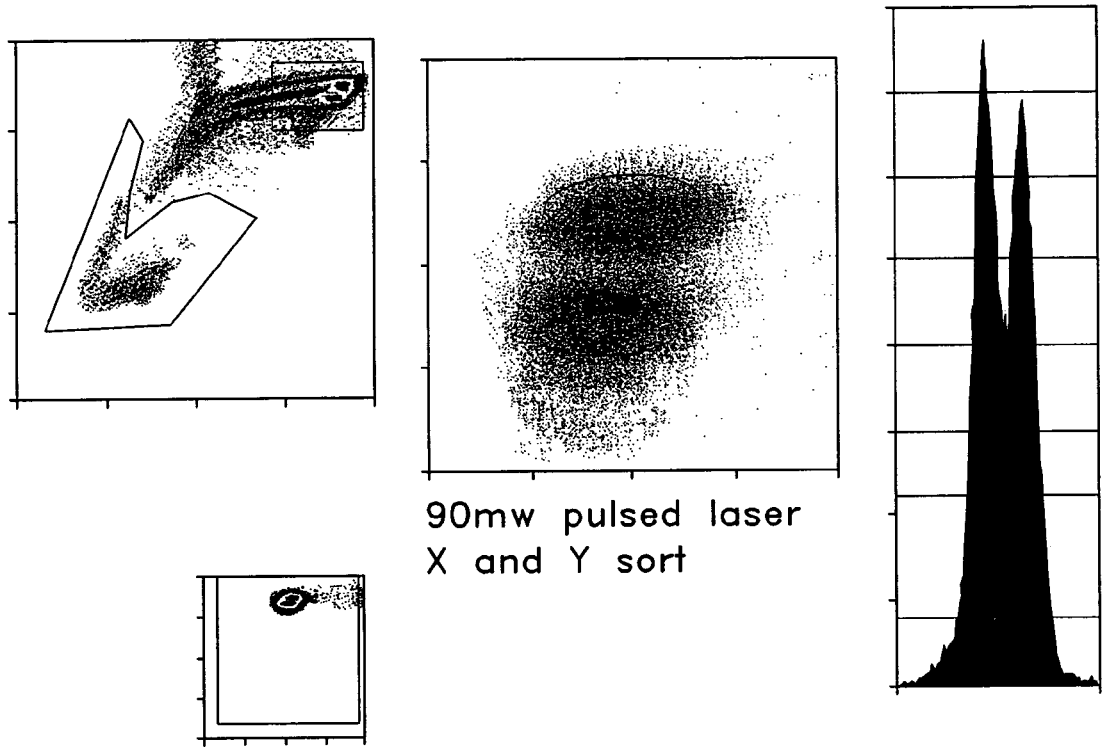
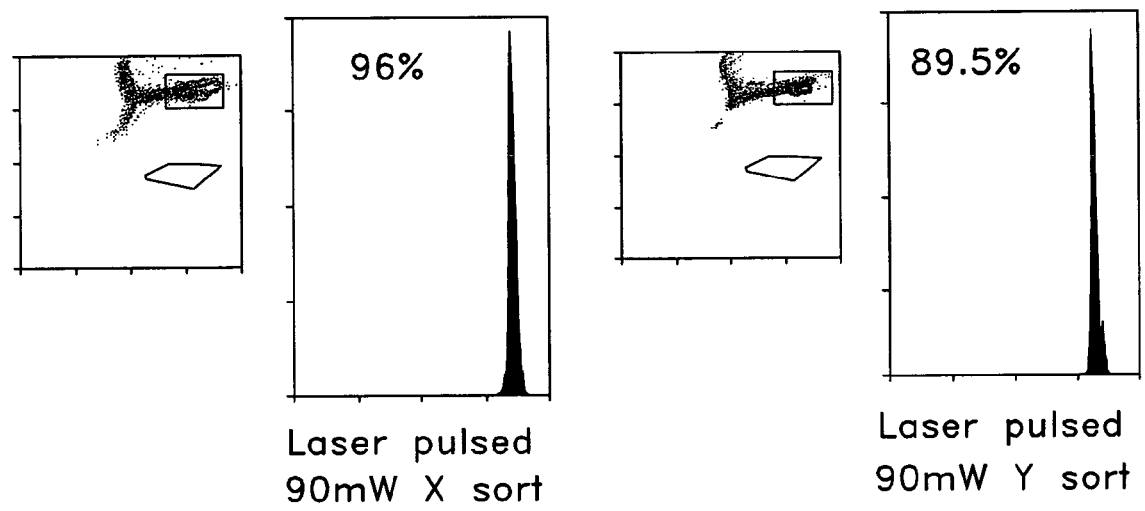
Fig. 16

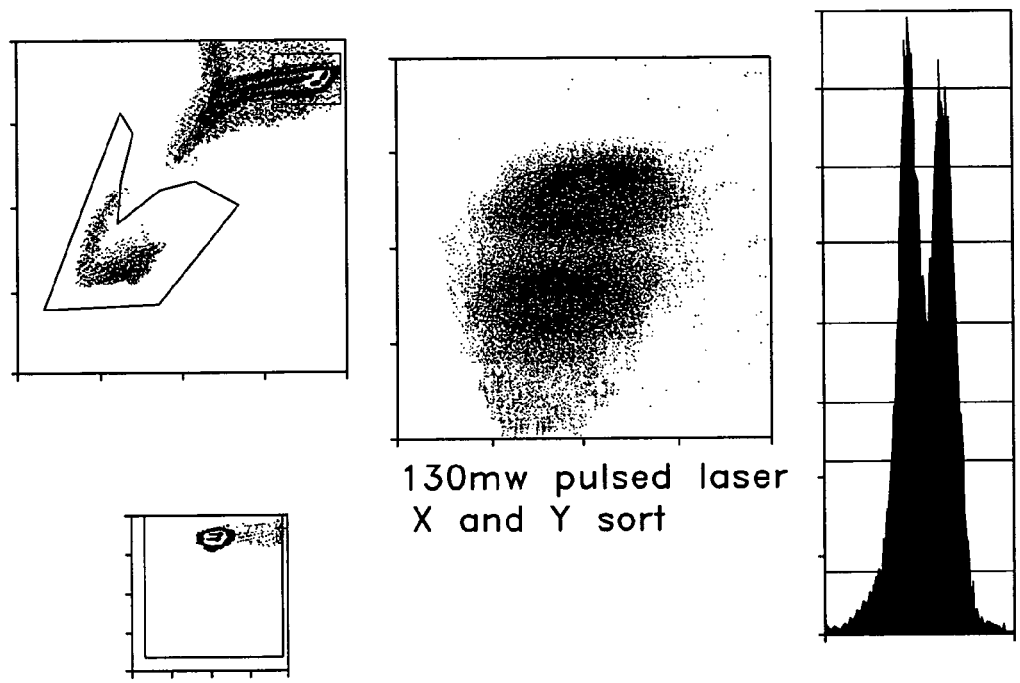
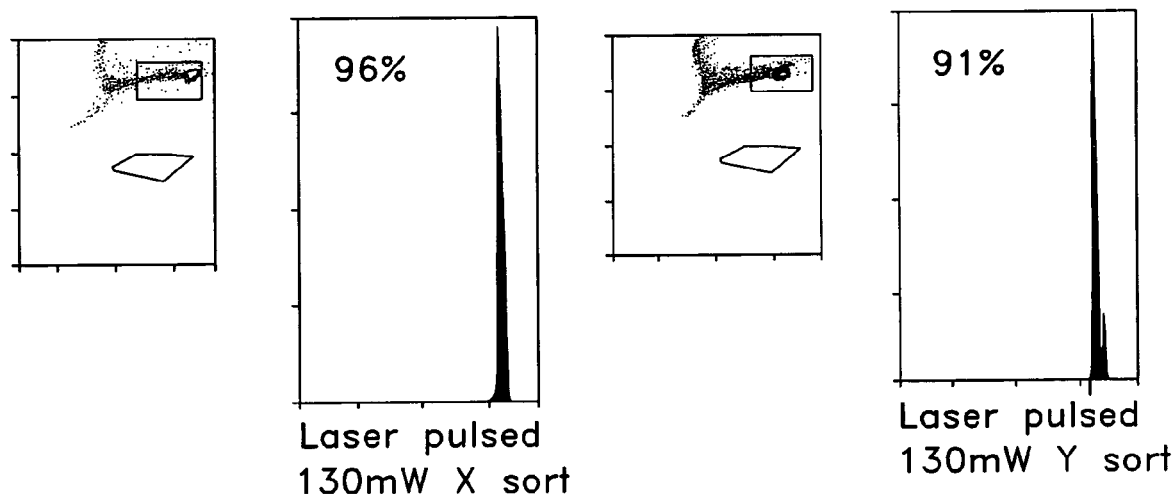
Fig. 17

APPARATUS, METHODS AND PROCESSES FOR SORTING PARTICLES AND FOR PROVIDING SEX-SORTED ANIMAL SPERM

This application is a continuation of application Ser. No. 10/556,981, filed Nov. 15, 2005, which is the United States National Stage of International Application No. PCT/US2004/015457, filed May 15, 2004 which claims the benefit of U.S. Provisional Patent Application No. 60/471,509, filed May 15, 2003, each hereby incorporated by reference herein.

I. FIELD OF THE INVENTION

The present invention relates to a flow system for particle analysis. More specifically, the invention relates to the use of a pulsed laser on a flow system for particle analysis which results in more accurate quantification of measurable properties of individual particles. It may be of particular interest in analyzing populations of very similar particles, at high speeds, allowing more efficient separation of particles into two or more different populations. The invention is particularly useful in the application of separating live X-chromosome bearing and Y-chromosome bearing sperm of all mammals at higher speeds, better purities and with equal or better sperm health outcomes, meaning less damage to sperm. The invention may contribute significant improvements to the economics of sperm sorting.

II. BACKGROUND OF THE INVENTION

Lasers can be used to deliver light to biological or non-biological particles and emission spectra can be used for the analysis of particle characteristics. In some instances, this can be applied such as where a particle is self florescent or self color absorbing, is associated by affinity, avidity, covalent bonds, or otherwise to another molecule which may be colored or fluorescent, may be associated to another molecule which is colored or fluorescent through a specific biological or modeled macromolecular interaction, such as an antibody binding event or a nucleic acid oligomer or polynucleic acid hybridization event, may obtain color or fluorescence such as through an enzymatic synthesis event, an enzymatic attachment or cleavage reaction, enzymatic conversion of a substrate, association of a florescent molecule with a nearby quencher, the reaction of a product in certain local proton (pH) or NADH or NADPH or ATP or free hydride (H—) or bound hydride R—(H—) concentrations, or may gain color or fluorescense by way of a variety of methods to associate emitted or absorbed light (electromagnetic radiation EMR).

Conventional lasers can generate a strong, perhaps intense, source of light. Through coherence properties of the beam such light may travel very long distances, perhaps across reflective mirrors which may change the angle of the light illumination beam, perhaps through prisms or refractive objects or lenses which may split it into two or more beams of equal or differing intensity, or may defocus, perhaps expand, or focus, perhaps concentrate, the beam. Such light may also be affected by filters which may reduce the net energy of the beam. Most lasers also allow the modulation of light intensity, perhaps watts, in the beam by adjustment of an input current from a power supply to the light generating element.

In some applications, conventional lasers used in the analysis and quantification of biological objects can be combined with sensitive light detectors that may be as simple, such as a photographic film or paper, or may be more complex, such as a photomultiplier tube. Often, a light detector may collect only information about a cumulative amount of light, perhaps electromagnetic radiation, EMR, or it may collect and report on the dynamic changes in intensity of light or EMR hitting all of, or portions of, localized regions of, or positions on the detector surface. The light detector may also involve use of a photoelectric coupling device, which may allow the energy of photons absorbed on the EMR by the light detector to be converted to current proportional to the incident light or EMR on the light detector surface. The photoelectric coupling device can even be integrated into an electronic circuit with an amplifier which may increase the signal or create gain such that the fluctuations or perhaps summation of amplified current may be available to an analog or digital logic circuit. Designs may also transmit a signal or data set to a user of a particle analysis instrument and this signal may be proportional to the static, cumulative, or perhaps even dynamic intensity of the light or EMR incident upon the detector.

In certain uses of laser light to analyze biological particles, a detector may measure the change in intensity of the source light after incidence upon a particle(s) being analyzed using a reference beam which takes a path without incidence upon the particle(s). In other uses of laser light, modified or unmodified particles take up a fraction of the illumination light or EMR and may emit light of a different frequency. In many cases, the presence of emission light or EMR of a certain wavelength can be used to identify or to quantify characteristics associated with specific particles, or quantitatively measure the amount or number of the specific biological particles present in the sample or in a specific region of or position in the sample.

In some cases, it can be useful to accurately determine very small differences in the illumination light or emission light from two very similar biological particles (for example an X-chromosome bearing sperm cell versus a Y-chromosome bearing sperm cell). These small differences can be analyzed by way of serial presentation of perhaps 50,000 separate emission events per second in a liquid stream. These can also be thousands of separate emissions from molecules (nucleic acids or proteins as examples) on an array field allowing analysis of genetic, genomic, proteomic, or glycomic libraries.

The traditional type of laser used for the analysis of particles in flow cytometry is a continuous wave (CW) laser. Often this provides a beam of constant intensity. However, in some instances, CW lasers can have particular disadvantages for applications as discussed here. The beam can result in modification or destruction of the sample being observed. For example, with respect to sperm cells, irradiation can result in lower fertility of the sperm cells. Second, in some instances when the laser beam continuously operates, it may be desirable to have a method of interrupting the beam if it is moved from a first location of incidence to a second location of incidence without illumination of intermediate areas.

In U.S. Pat. No. 5,596,401 to Kusuzawa, a pulsed laser may be used for imaging an object, such as a cell, in a flow cytometer. This disclosure may be related to improvements in the capture of images from particles such as coherence lowering modulations. Kusuzawa may teach a use of a continuous wave laser for particle detection and imaging.

In U.S. Pat. No. 5,895,922 and U.S. Patent Application No. 2003/0098421 to Ho, pulsed laser light may be used to illuminate and detect hazardous biological particles dispersed in an airflow stream. The invention may include an ultraviolet laser light and looking for the emission of fluorescence from potentially hazardous biological particles. This disclosure may teach the disadvantages of a laser diode apparatus.

U.S. Pat. No. 6,177,277 to Soini, describes employing a two-photon excitation and/or confocal optimal set-up. The invention may relate to the use of confocal optics to reduce an analysis volume to about 10% of standard analysis volume in a flow cytometer. A pulsed laser may provide short pulses of intense light and may allow the simultaneous absorption of two photons so that a wavelength of illuminating light beam may be longer than an emitted single photon bursts. Background signal may be reduced by use of a filter. The invention may include dual signal processing. The invention as described in Soini, may be beneficial in the analysis of small particles such as erythrocytes and bacterial cells.

In U.S. Pat. No. 6,671,044 to Ortyn, a special analysis optics and equipment may be used in an imaging flow cytometer. The Ortyn disclosure may include analyzing a sex of fetal cells in maternal blood as a method for determining the sex of a child during early pregnancy. Ortyn may indicate that analysis rates from an imaging flow cytometer may be restricted to theoretically maximizing at 500 cells per second.

With respect to particle analysis using laser light, the present invention discloses technology which addresses each of the above-mentioned problems.

For the purposes of this invention, a rapidly pulsed, high intensity pulsed laser may be used. This laser may deliver short pulses of high intensity perhaps lasting about 5-20 picoseconds, followed by intervals between pulses which are 100-1000 times as long as the pulses or about 0.5-20 nanoseconds. The light may have very high peak intensities over the period of about 5-20 picoseconds, and low net energies over the period of about 2-10 microseconds.

Flow cytometry, using a high-speed cell analysis, or high-speed cell analysis and sorting instrument, often relies on a laser light source to illuminate a stream of fluid in which particles are entrained. Particles may be caused to flow by a point of illumination at a rapid rate, often in the range of 500 to 100,000 particles per second. Often the light from the illuminating laser source is of constant intensity. The particles in the analysis stream may be of the same size, and may spend the same amount of time within the area of illumination. The amount of light illuminating each particle in a large population of particles analyzed in series may be identical. A detector may be capable of measuring scattered light, or other types of light emitted by the particle as a result of auto-fluorescence or fluorescence associated with a chemical dye, dye complex, or conjugated dye which may be targeted to one or more types of molecular species contained on or within particles in the population and can determine the identity of a particle and, in some cases, make a measurement of the quantity of a specific molecular target associated with the particle. A specific molecular structure on or even within a particle may be characterized and a quantitative measurement of the amount of associated molecular structure on or even within a particle, may yield information which may be used as a basis for sorting out or separating one type of particle from another.

In a flow cytometer, there may be a very short time duration between the exact moment that a particle is illuminated and the exact moment that a physical manipulation or an electrical condition, may be triggered to elicit separation of a specific particle from a stream containing various particles. An example of a physical manipulation may be charging of a droplet. A specific duration may be called a drop delay period, and the duration may be perhaps as brief as about 100 microseconds or perhaps as long as about 10 milliseconds, and may even be about 1 millisecond. In the case of particle sorting, information may be detected from each particle, computational analysis of the information may be determined, and comparison of the computation to a gating value or perhaps even a selection criteria may be accurately performed within a time period shorter than a duration of the drop delay.

Flow cytometer systems may be useful for measuring an average amount of a specific molecule present on or even within a population of particles. Past systems may not have measured the exact amount of a specific molecule on or even within a population of particles. Factors which can contribute to inaccurate measurements of single particles may include the saturation of a stain or even a conjugate to a particle, variation in the quanta of illumination light, effects from the shape of a particle, and perhaps even electronic noise in the detection apparatus.

An example of a particularly challenging problem is the sorting of X-chromosome bearing and Y-chromosome bearing sperm of mammals at high processing rates and high sorting purities. The population of sperm in most mammals is about 50% X-chromosome bearing and about 50% Y-chromosome bearing. A stain, such as Hoechst 33342, may form complexes with double stranded DNA. A measurement of total Hoechst 33342-DNA complex in each sperm may correlate to the total amount of DNA in each sperm. In general, mammals have larger X chromosomes than Y chromosomes and may have a differential between total DNA contents of X-chromosome bearing over Y-chromosome bearing sperm for various mammals. Such differentials may include: human having about 2.8%; rabbit having about 3.0%; pig having about 3.6%; horse having about 3.7%; cow having about 3.8%; dog having about 3.9%; dolphin having about 4.0%; and sheep having about 4.2%. The differentials may correlate to a relative difference of intensities emitted from a stained sperm being sorted for the purpose of separation of X-chromosome bearing and Y-chromosome bearing sperm.

Significant achievements have been made in developing staining conditions to stain DNA in live sperm with Hoechst 33342, such as, the use of dual orthogonal detection systems to determine sperm orientation, the use of hydrodynamic fluidics to increase the numbers of correctly oriented sperm, the setting of gain on detectors, and even the use of high-speed electronics. In the most efficient use of said achievements, it may be possible in most mammals to simultaneously sort sperm into two populations, X-chromosome bearing, and Y-chromosome bearing, at rates of 2500 per second or higher. It may also be possible to sort sperm to purities of 90% or even higher. There may be, however, a distinct problem in that at rates faster than 2500 per second, the purity of the sample may decrease.

This problem may be understood due to the observation that the co-efficient of variation (CV) in possibly even the best sperm sorting procedures may be between about 0.7%-1.5%, and with poor conditions can even be between about 2%-5%. Since the difference in DNA between X-chromosome bearing sperm and Y-chromosome bearing sperm in mammals may be as low as 2.8% as seen in humans and as high as 7.5% as can be seen in chinchillas, the CV may be lower than the DNA differential in order to achieve a large enough separation of the two populations. Humans have one of the lowest known DNA differentials and may have some of the lowest known maximum purities in sorting. It may be desirable to improve procedures which can reduce the CV.

A method which has been shown to improve the CV may be to use higher intensities of laser light illumination. For example, it is known to use continuous wave lasers to sort various sperm species with between about 100-200 milliwatts of laser illumination, and possibly with about 150 milliwatts. It has been observed that doubling or tripling the intensity and increasing the power to about 300-500 mW can improve the CV. An improved CV can be most apparent by analysis of the "split" between two peaks on a histogram. Yet, there may be problems associated with an increase of intensity or perhaps even an increase of power with a continuous wave laser. In the case of analyzing a Hoechst 33342 DNA complex with a continuous wave laser, the light source may be near a UV spectrum and may have some ionizing effect upon the DNA complex. Ionizing may then cause changes to the DNA. Accordingly, sperm sorted with high intensities continuous wave lasers such as 300-500 mW may not be as fertile. Another problem may include the energy that it may take to power a continuous laser to deliver about 150 mW of energy at near UV spectrum. Continuous wave lasers may require 10,000 mW or perhaps even more of power. Since there may already be a large amount of electrical power required to run a continuous wave laser at 150 mW, a much larger amount of power may be required to run a continuous wave laser at higher powers. Furthermore, a tube life of ion lasers may be reduced when operating at higher powers. An additional problem with the use of continuous wave lasers may be that the CV may drop significantly when using lower powers such as between about 20-80 mW.

In embodiments, the present invention provides flow cytometer designs which may incorporate the use of 2 or more flow nozzles, and even as many as dozens of flow nozzles, possibly operated by a single sorting instrument. Fields such as microfluidics, optics, electronics, and even parallel processing may be explored. In other embodiments the present invention includes the use of beam splitters to create multiple light beams. Yet, a major problem facing the development of reliable flow analysis and flow sorting in parallel may be the high intensity of laser light needed for analysis at each nozzle. This problem is particularly relevant for applications which require a very low CV in measurement of identical particles.

There is a need to provide flow systems for the analysis and sorting of particles that require a low CV value, yet may require higher laser light intensities, yet higher intensities may have negative effects on sperm and require higher power. In the search for solutions to the problems in flow systems for the analysis and sorting of particles, the field of pulsed lasers represents a possible solution.

Surprisingly, even though sperm sorted on a high speed flow cytometer may be damaged by UV light between about 300-500 mW, it is now shown in this invention that powers between about 100-500 mW may not be damaging to sperm if they are delivered in pulses. In embodiments, this may include a pulse having a peak intensity possibly as much as 1000 times higher than the intensity of a continuous wave laser. Pulsed lasers may be designed as quasi-continuous wave lasers and may have fast repetition rates such as between about 50-200 Megahertz and even up to 80 Megahertz. In embodiments, pulses may be between about 5-20 picoseconds. Pulsed lasers may be ideal for providing pulsed light to a stream of particles being analyzed in a flow cell or a flow cytometer. Particles analyzed in flow cytometers with event rates possibly between 10,000-100,000 Hertz, and even between 20,000-60,000 Hertz, may be illuminated from a few hundred pulses from a laser having repetition rates near 80,000 Hertz. Each pulse may provide an intense amount of energy.

There may be certain industrial uses of flow cytometers, as preparative instruments, which may be economically limited by the traditional methods of processing. It may be desirable to provide systems which facilitate parallel processing for industries such as those that rapidly process mammalian ejaculates for the production of large numbers of live sperm for insemination, those that process blood samples for the recovery of specified cells such as fetal cells, white blood cells, stem cells, hematopoetic cells from bone marrow, and the like. In an embodiment of the present invention, special forms of pulsed laser light can allow a single laser to illuminate a plurality of nozzles, perhaps even while not reducing the CV of the samples analyzed.

As a result, by the use of special forms of pulsed laser light, further improvements in the speed and sample purity can be seen. These types of lasers may be essential in the design and development of new flow cytometers perhaps having multiple sorting streams as well.

III. SUMMARY OF INVENTION

Accordingly, a broad object of the invention may provide a particle analysis system having a pulsed laser which can be operated at a low power.

Another broad object of the invention can be to provide a particle analysis system having a pulsed laser which may allow detection of smaller differences in illumination or emission to differentiate a particle characteristic.

Yet another broad object of the invention can be to provide a particle analysis system having a pulsed laser which allows differentiated particles to be separated into subpopulations having a higher incidence of the desired characteristic.

Another broad object of the invention can be to provide a particle analysis system having a pulsed laser which allows multiple particle differentiation systems to be run simultaneously using a single laser.

Another broad object of the invention can be to provide a particle analysis system having a pulsed laser which affords greater resolving power than conventional particle analysis systems using a CW laser.

Another broad object of the invention can be to provide a particle analysis system having a pulsed laser which generates from fluorochromes upon irradiation greater light intensity than conventional particle analysis systems using a CW laser.

Another broad object of the invention can be to provide a particle analysis system having a pulsed laser which allows differentiated particles to be separated into subpopulations at a greater rate than conventional particle analysis systems using a CW laser.

Another broad object of the invention can be to provide a particle analysis system having a pulsed laser which allows sperm cells of any species of mammal to be differentiated with increased resolution into X-chromosome or Y-chromosome bearing subpopulations. The benefits of this object of the invention may allow differentiation of sperm cells having: less DNA bound fluorochrome, less residence time in staining protocols, greater elapsed storage time prior to sorting, or perhaps even less affinity to stain due to having been frozen prior to staining protocols.

Another broad object of the invention can be to provide a particle analysis system having a pulsed laser which allows sperm cells to be separated into X-chromosome or Y-chromosome bearing subpopulations having higher purity or separated into X-chromosome or Y-chromosome bearing subpopulations at a greater number per second.

Yet another broad object of the invention can be to provide a miniaturized and parallel flow cytometer which allows a multiple of nozzles sorting in tandem to be positioned on the same apparatus, that may allow increases in the production rate of sorting, by increasing the number of nozzles which are sorting on a single apparatus.

Naturally, further independent objects of the invention are disclosed throughout other areas of the specification.

IV. BRIEF DESCRIPTION OF THE DRAWINGS

FIG. 1 provides a block diagram of an embodiment of a particle analysis system invention which includes beam manipulators such as optical elements, splitters, filters, directional or the like.

FIG. 2 provides other embodiments of beam manipulators.

Figure 5:
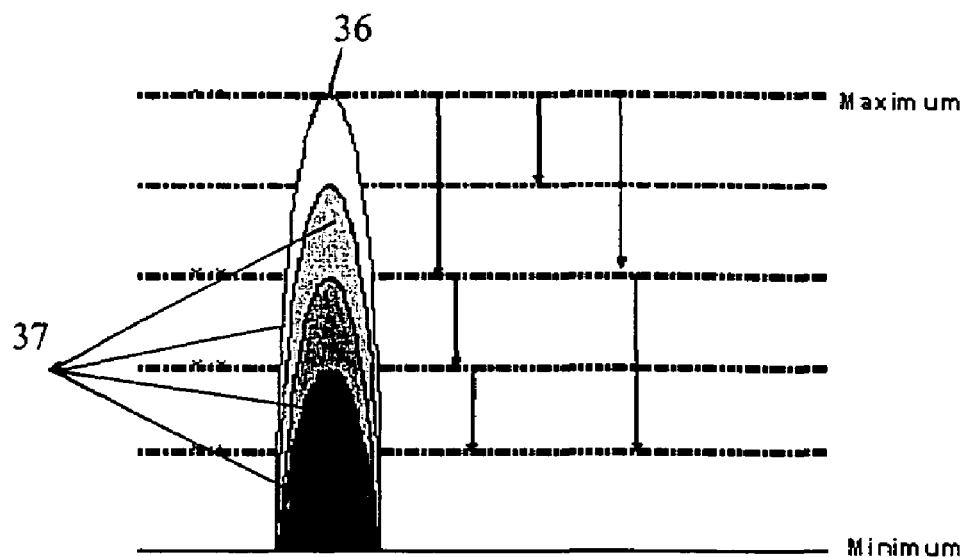

FIG. 5 provides illustrations of characteristics of a pulsed illumination beam.

Figure 6:
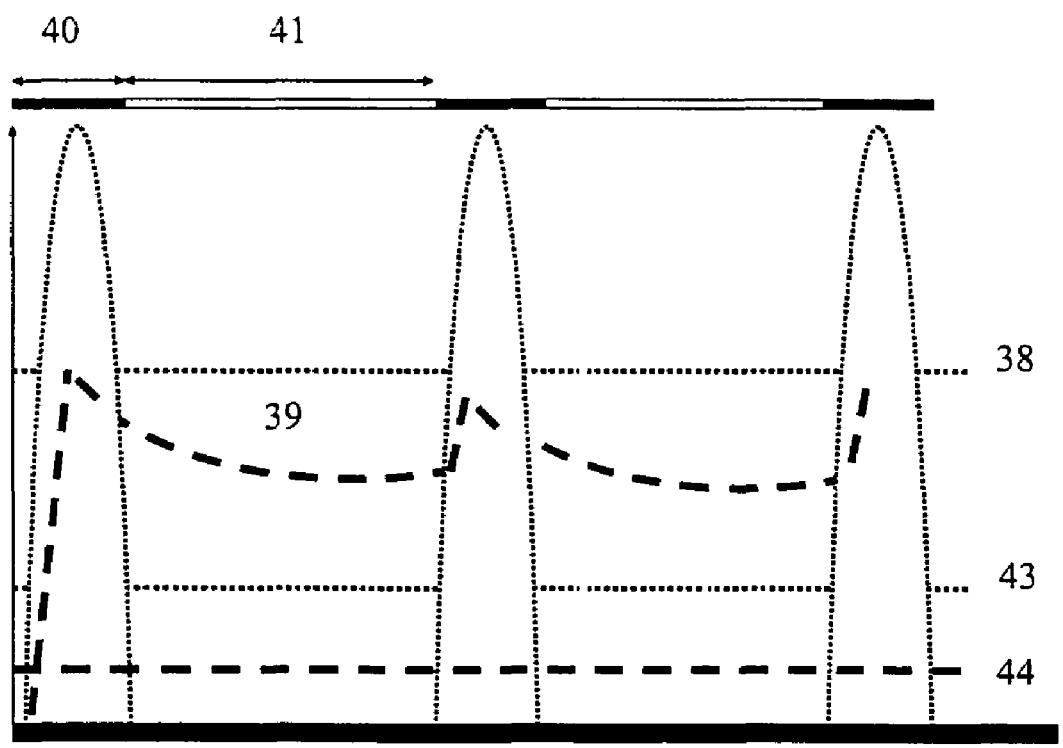

FIG. 6 provides illustrations which may differentiate characteristics of a pulsed radiation beam from a conventional continuous wave radiation beam.

Figure 7:
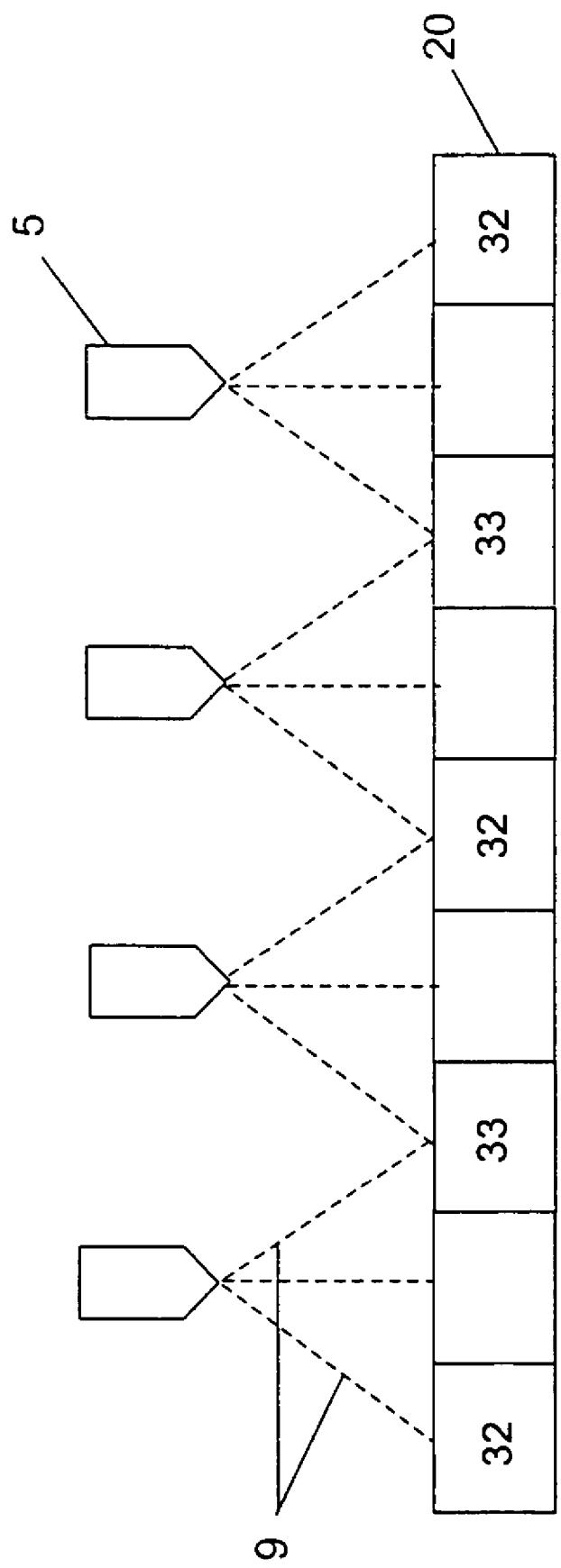

FIG. 7 shows an embodiment of the invention representing a sorting process having multiple nozzles.

Figure 8:
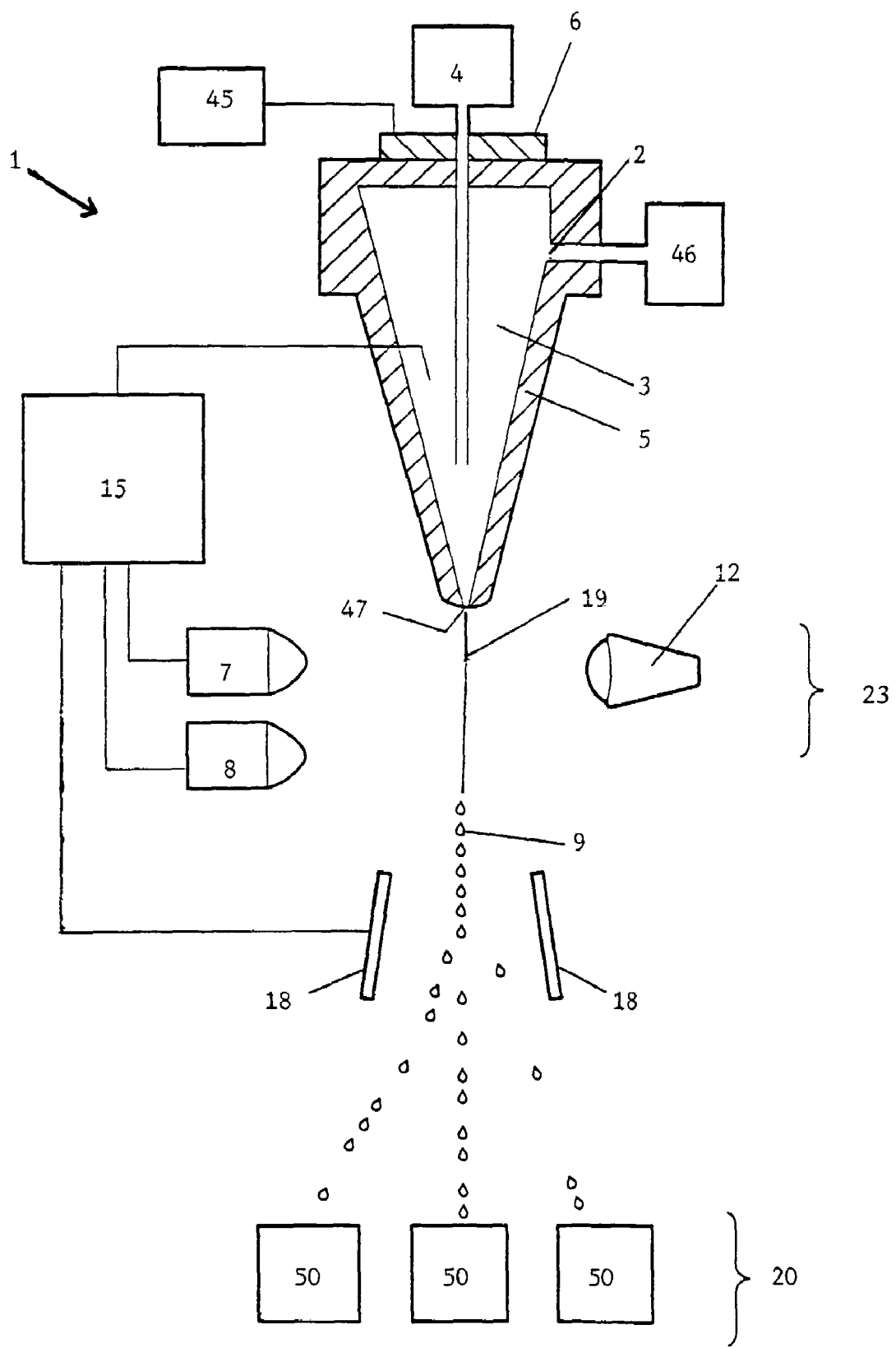

FIG. 8 is a drawing of a flow sort embodiment of the invention.

Figure 9:
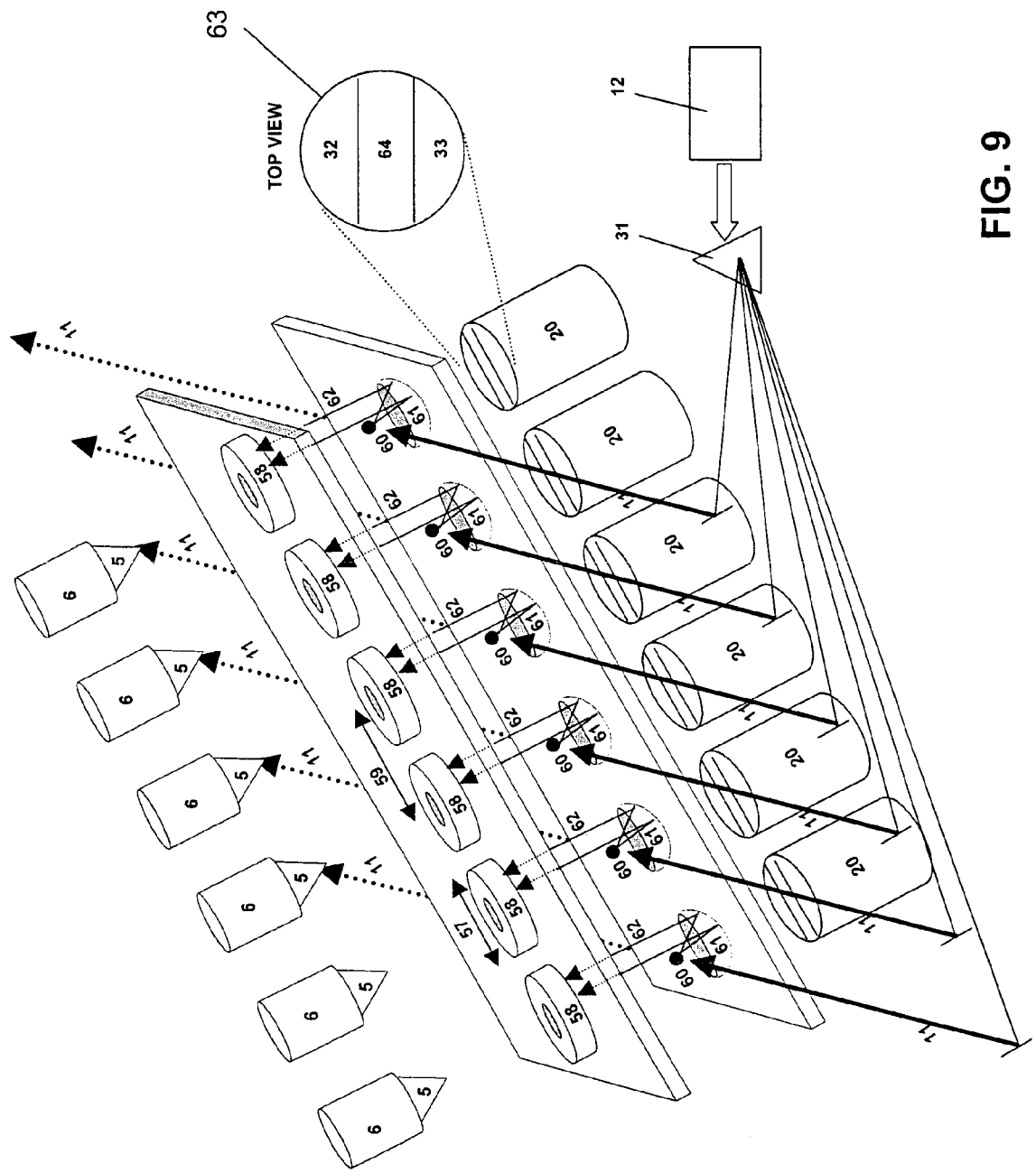

FIG. 9 provides an expanded diagram showing various embodiments of a multiple nozzle assembly.

Figure 10:
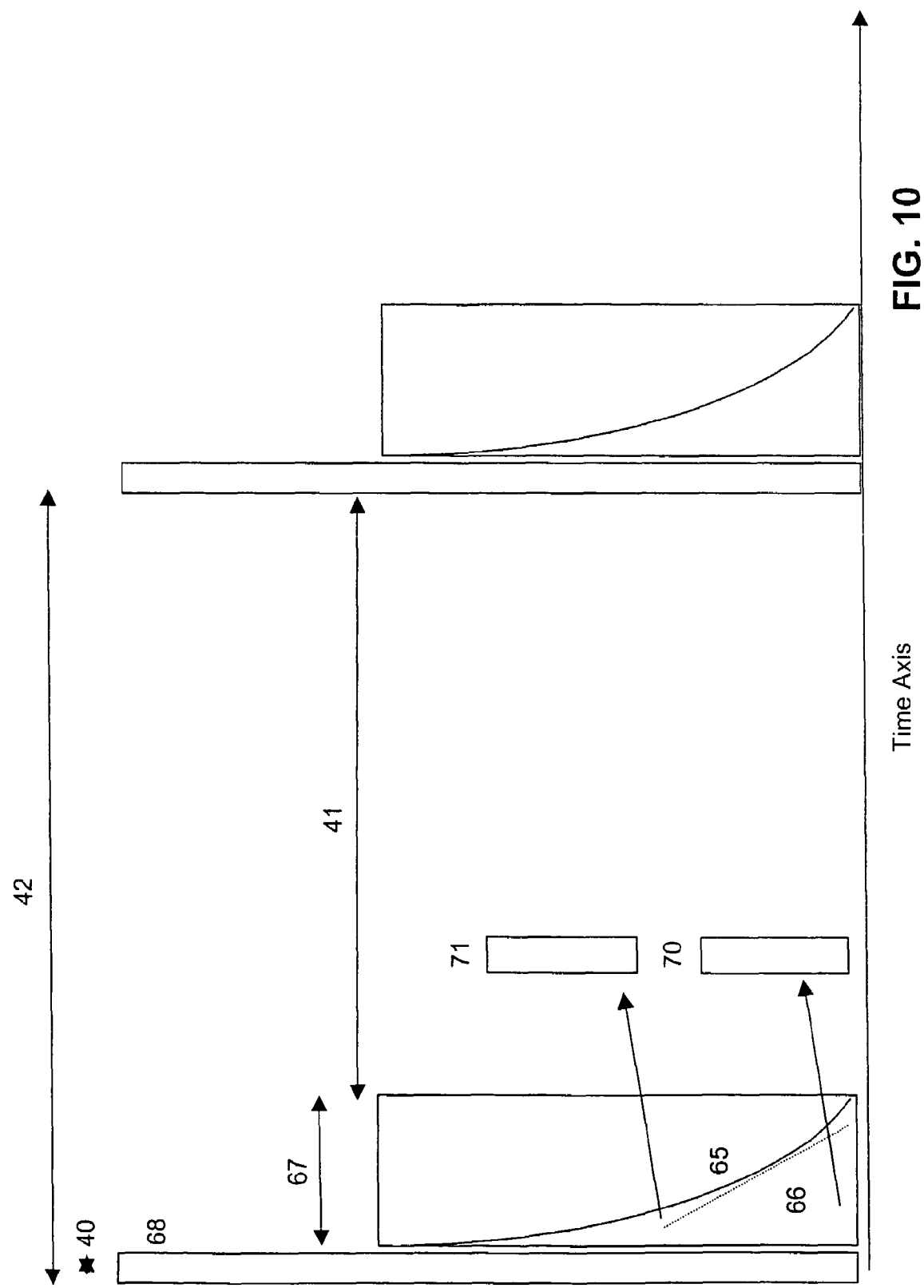

FIG. 10 depicts embodiments of certain time intervals and light energy quantities which may be derived from particular properties of pulsed light.

Figure 11:
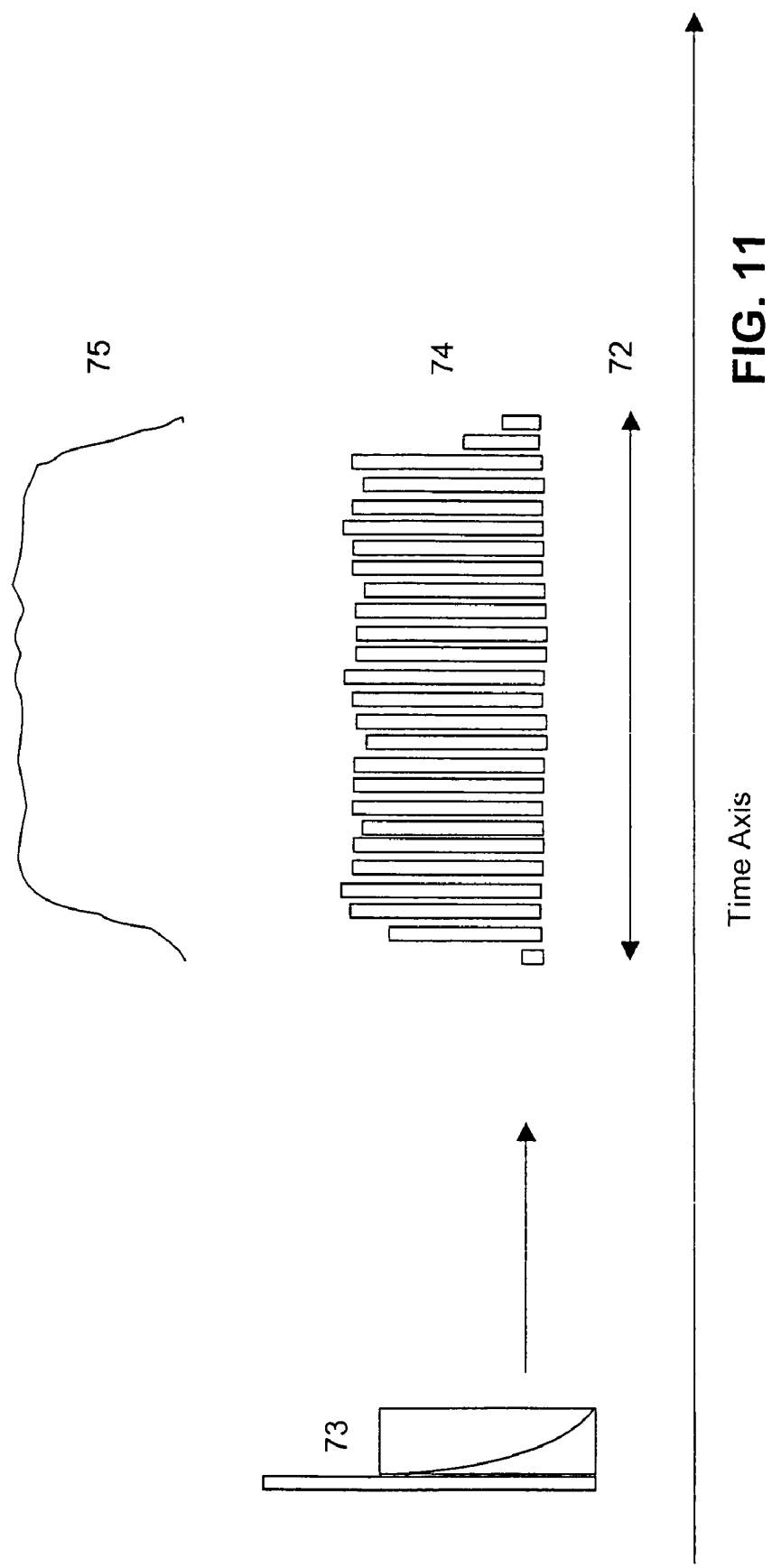

FIG. 11 is a comparison of a pulsed laser radiation beam and a continuous wave laser radiation beam.

Figure 12:
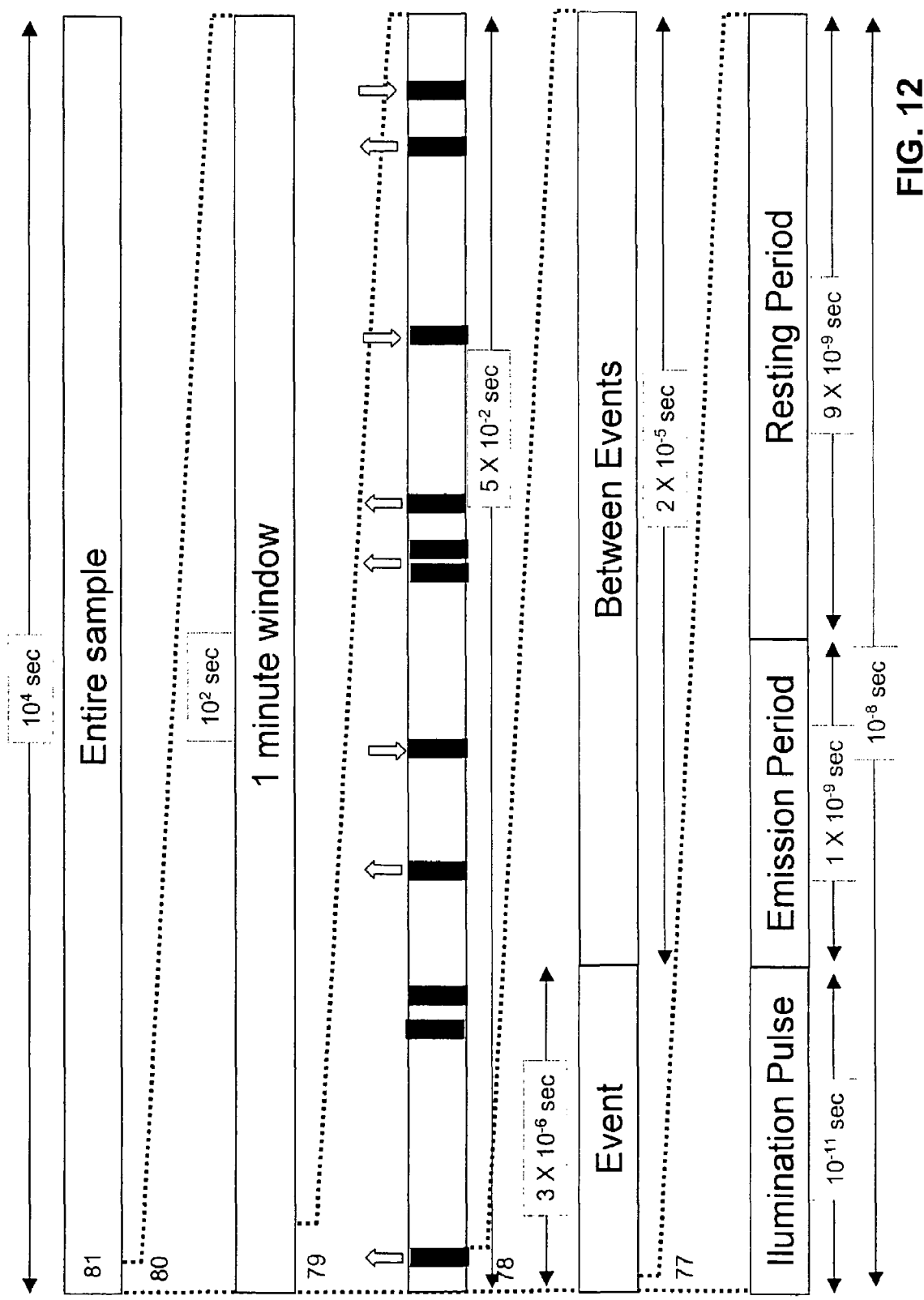

FIG. 12 is a representation of an embodiment for a sensing routine.

Figure 13:
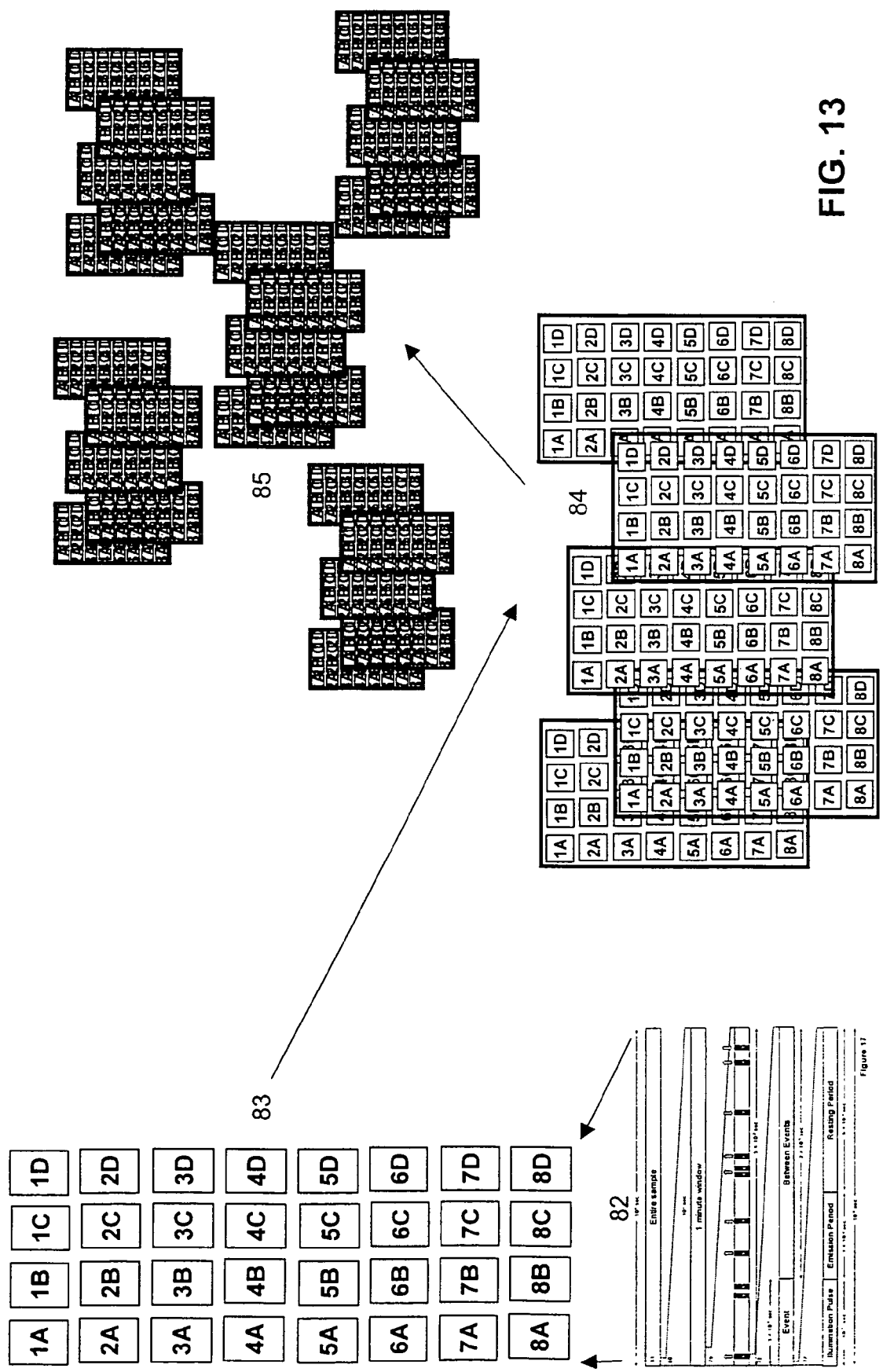

FIG. 13 is a representation of a comparison of aggregate data from various trial data.

Figure 14:
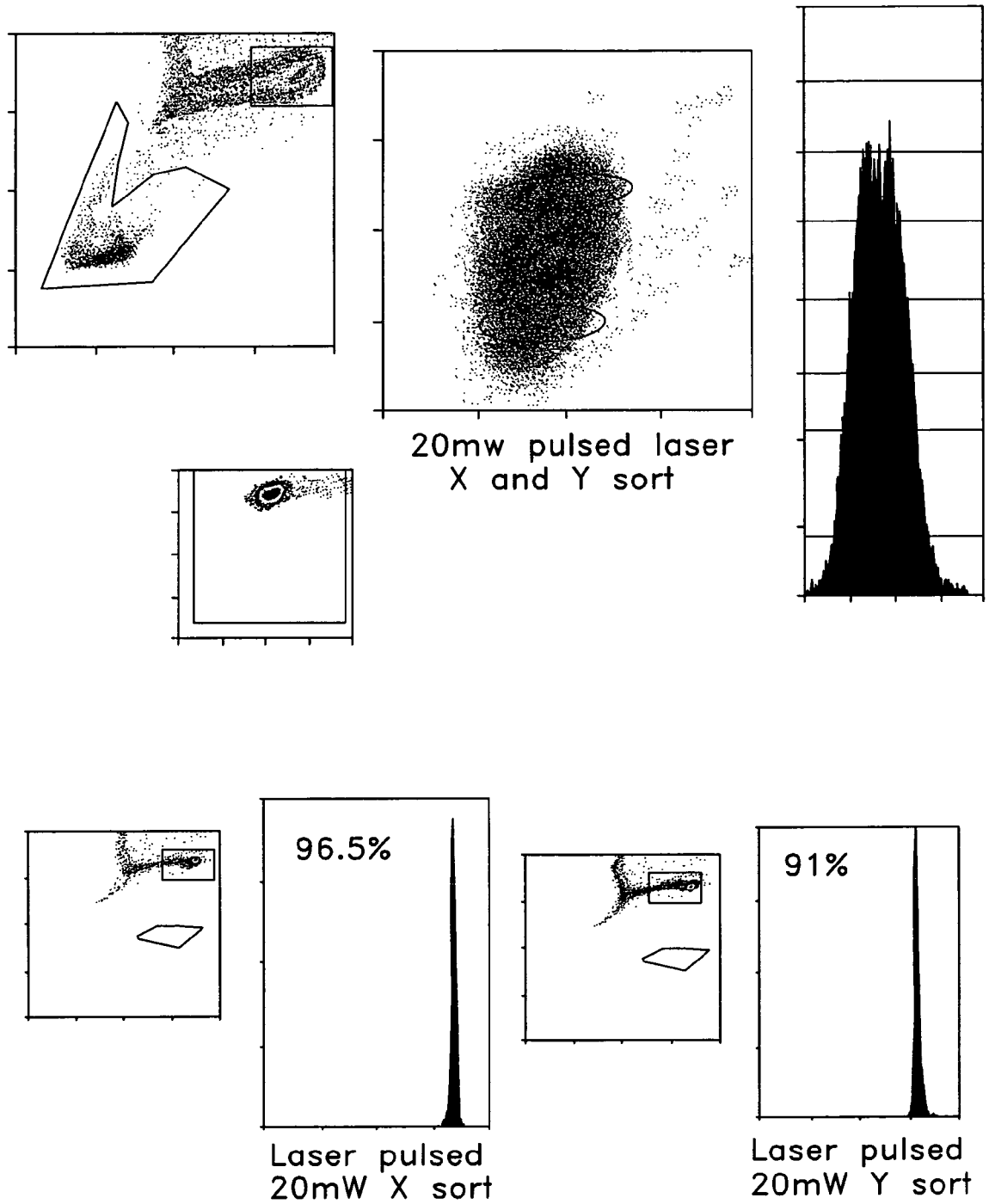

FIG. 14 provides histograms and bivariant plots of X-chromosome bearing and Y-chromosome bearing subpopulations of sperm cells using a flow sort embodiment of the invention which provides a 20 mW pulsed laser beam incident to the sperm cells analyzed.

Figure 15:
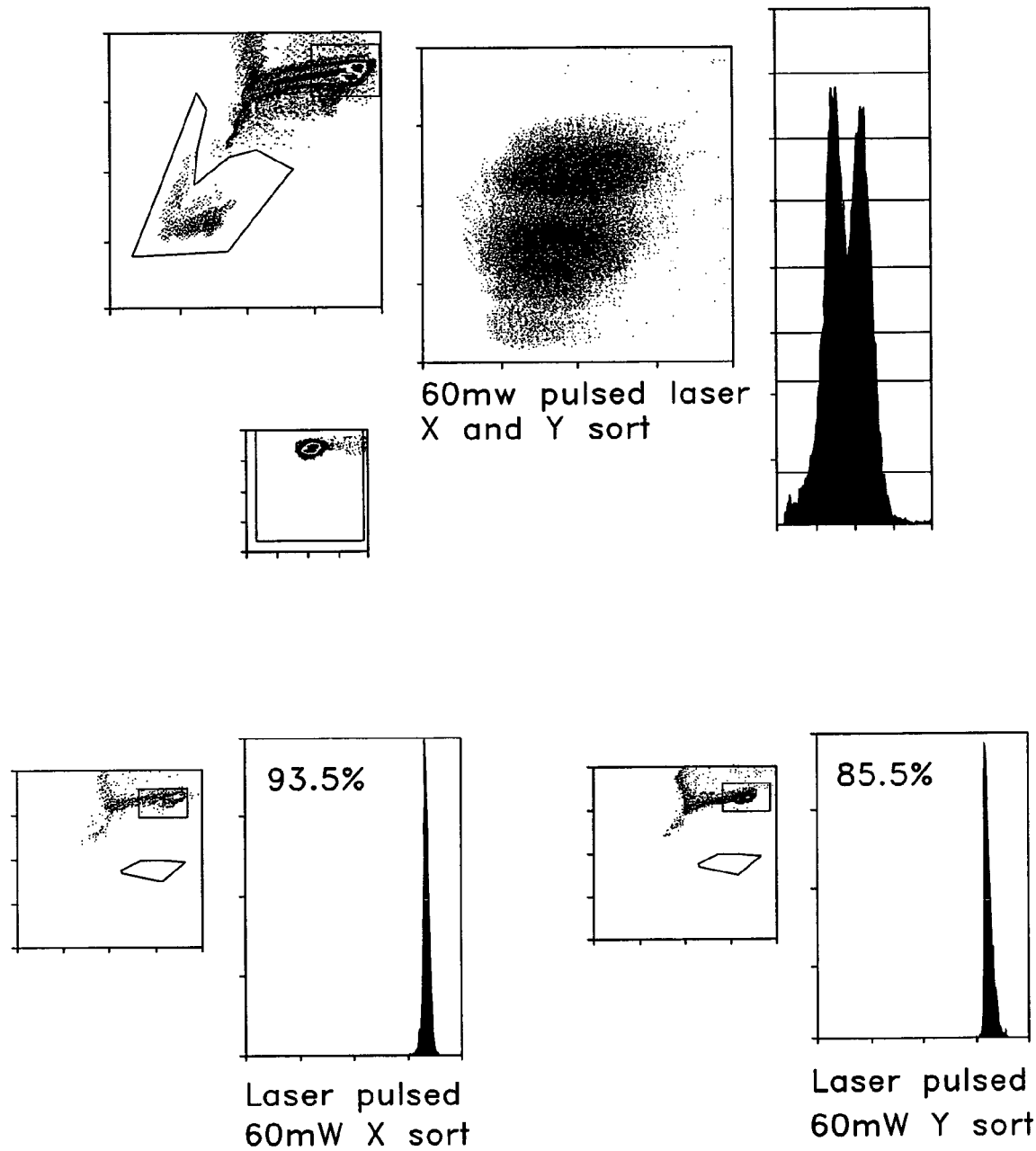

FIG. 15 provides histograms and bivariant plots of X-chromosome bearing and Y-chromosome bearing subpopulations of sperm cells using a flow sort embodiment of the invention which provides a 60 mW pulsed laser beam incident to the sperm cells analyzed.

FIG. 16 provides histograms and bivariant plots of X-chromosome bearing and Y-chromosome bearing subpopulations of sperm cells using a flow sort embodiment of the invention which provides a 90 mW pulsed laser beam incident to the sperm cells analyzed.

FIG. 17 provides histograms and bivariant plots of X-chromosome bearing and Y-chromosome bearing subpopulations of sperm cells using a flow sort embodiment of the invention which provides a 130 mW pulsed laser beam incident to the sperm cells analyzed.

Figure 18:
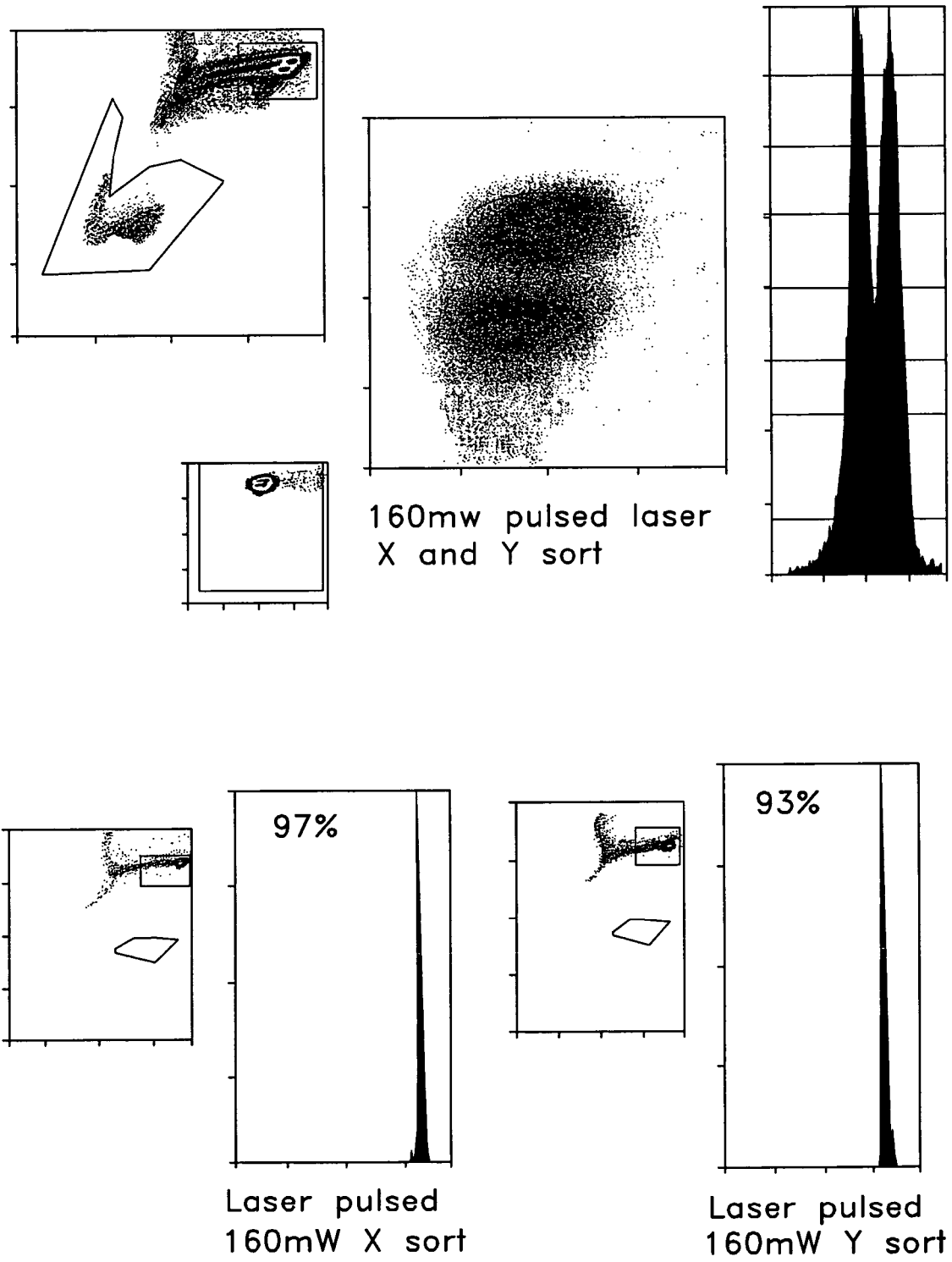
Figure 19:
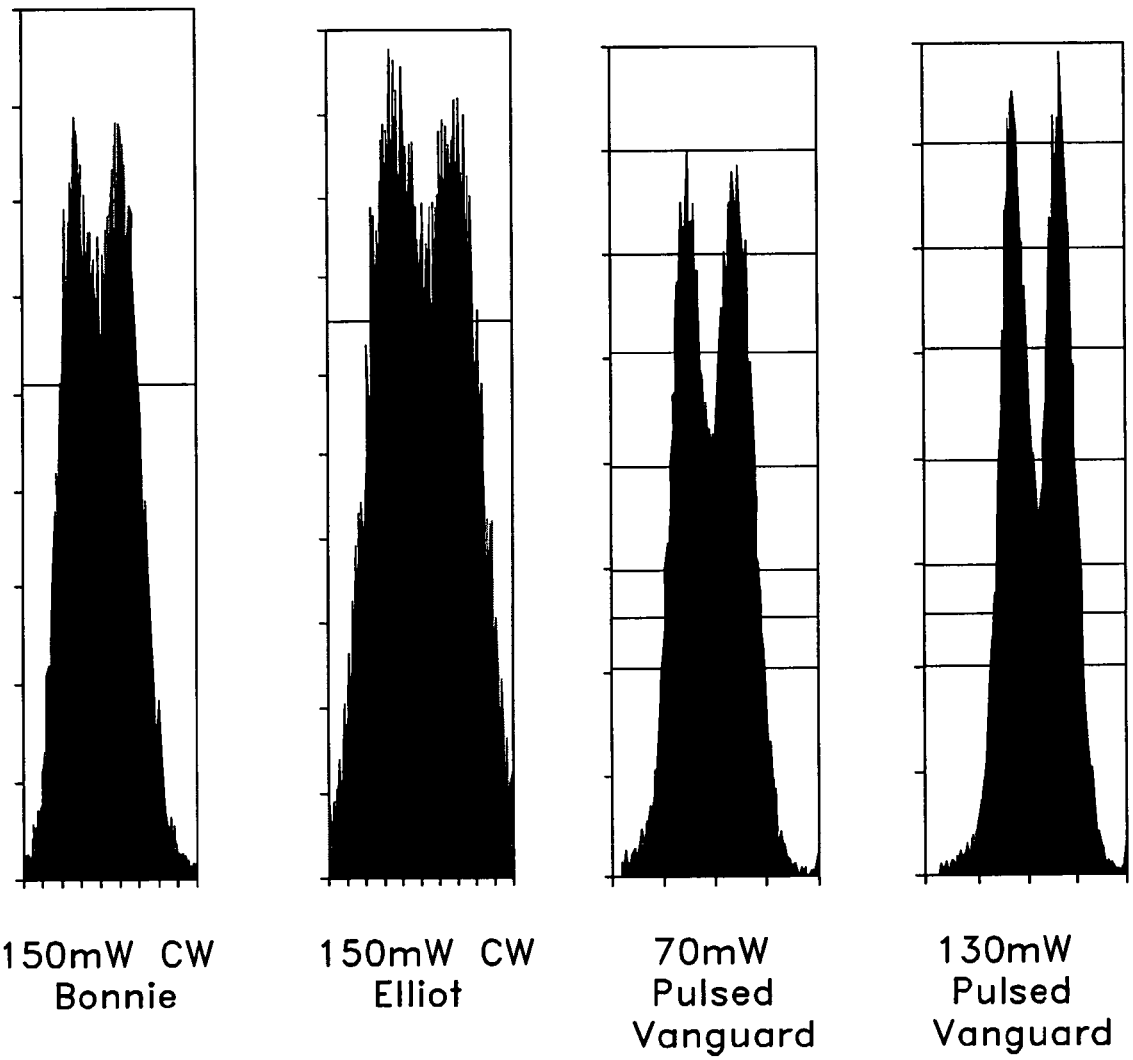

FIG. 18 provides histograms and bivariant plots of X-chromosome bearing and Y-chromosome bearing subpopulations of sperm cells using a flow sort embodiment of the invention which provides a 160 mW pulsed laser beam incident to the sperm cells analyzed FIG. 19 provides histograms of sperm cells analyzed with a flow sort embodiment of the invention compared to a histogram of sperm cells from the same sample analyzed with conventional CW flow sort technology.

V. DETAILED DESCRIPTION OF THE PREFERRED EMBODIMENTS

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
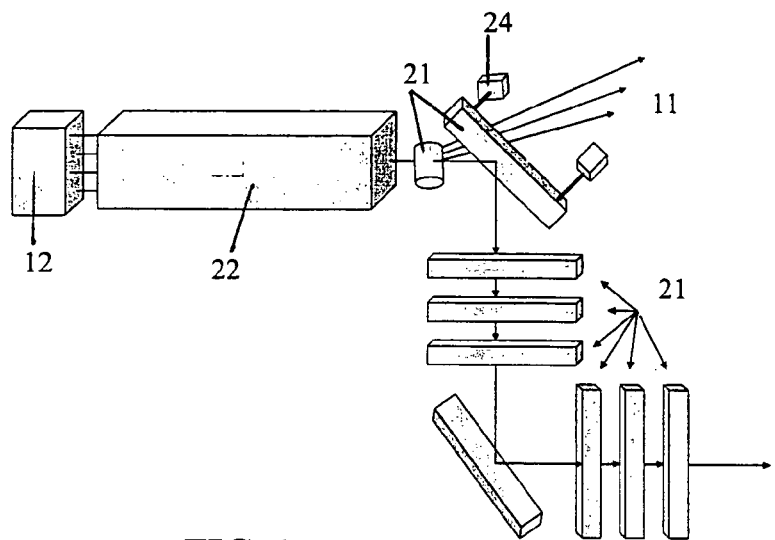

Referring primarily to FIG. 1, the present invention provides, in embodiments, a radiation emitter used with particle analysis systems. In some embodiments of the invention, a radiation emitter (12) or even an intermittingly punctuated radiation element may convert electrical current into photons of radiation of a specific wavelength and may generate radiation or even laser light for analysis of non-biological or biological particles. Radiation (11) may enter a chamber or region (22) in which it may be modulated or even modified, such as but not limited to establishing a coherent wave form. Radiation may be modified by a beam manipulator (21) such as optical elements before it may illuminate a particle or even a particle sample(s).

In some embodiments, beam manipulators (21) such as optical elements may be used and may be located along a light path. Beam manipulators may include mirrors, optically reflective or even refractive mirrors, partially mirrored surfaces, deflectors, beam splitters, refractive objects, lenses, filters, prisms, lenses, or the like. Beam manipulators may modify or even modulate a pulsed laser light by focusing, condensing, de-focusing, expanding, splitting, or the like. Radiation may be split into multiple beams of equal or perhaps even unequal intensity. A radiation beam manipulator may influence a radiation beam such as by adapting a beam or changing a beam as a particular situation may be needed.

With respect to some embodiments of the invention, positional control elements (24) can provide positional control over a mirror, lens, prism, filter, or other optically relevant components. A positional control element may influence the angle of reflection or even refraction of a beam, and may even ultimately direct a final position of a pulsed laser light beam on a particle or particle sample(s). A positional control element may be a mechanical device which may move a mirror along a path, or it may even be a ratcheting or even a stepped device which can provide large numbers of predefined angles for an optical element. A positional control element(s) (24) may be used at any point in a pulsed laser and even a pulsed light assembly or apparatus to modify a beam of pulsed laser light. An oscillator may provide a constant vibration in an optical element and may define a frequency and amplitude.

In order to provide splitting of radiation into at least two light beams, the present invention may include a beam splitter. This may subject sperm cells to a reduced power of radiation than a power of radiation with was originally emitted from a laser source such as radiation emitter. Examples of reduced radiation may include splitting a radiation beam in half, in a fourth of said originally emitted power or even in an eighth of the originally emitted power, as may be represented by FIG. 2. Of course, there are many options in which to reduce power and all are intended to be included within the scope of this disclosure. With a pulsed laser, for example producing a 100 mW output split into 8 equal beams of approximately 120 mW, it may be possible to have 8 flow cytometry nozzles sorting together from one light source.

Figure 2:
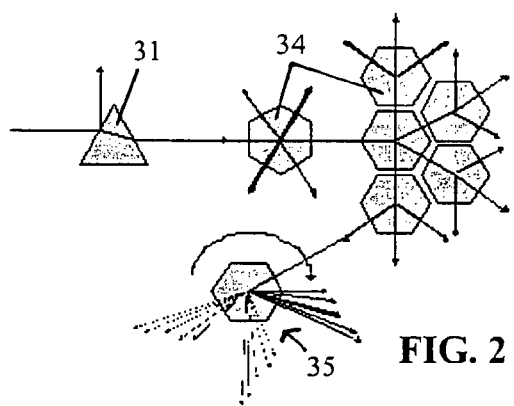

As to other embodiments of the invention, independent beams of pulsed laser light may be equal or may even be unequal in intensity. Split beams can be derived from a source beam of pulsed laser light by the action of optical splitters. As shown by FIG. 2, a beam splitter (31) such as a prism can divide a beam of radiation into at least two beams of the same frequency and pulse rate, but may have equal or even unequal intensities. Split beams of light may have intensities which can be each less intense than, or even additively close to an equivalent to the original beam which entered a splitter or prism. A complex beam splitter or prism, which with multi-faceted, three dimensional geometries can split a beam of pulsed laser light into more than one, certainly two, possibly dozens or even hundreds of independent beams of pulsed laser light.

Complex beam splitters (34) may include a three dimensional packed array of simple splitters or even prisms which can create combined three dimensional geometries of refraction and reflection and can even split a beam of radiation into more than one, certainly two, possibly dozens or even hundreds of independent beams of pulsed laser light. This may differ from a complex beam splitter in that an array of simple splitters and even prisms may allow individual geometries of each component, refractive index of each component, which may allow a much larger number of options. A rotational beam splitter (35) can be rotated on an axis, potentially at very high speeds, such that an extremely large number of pulsed laser light beams may be created to the point where one can no longer speak of actual beams, but rather of each pulse moving in an independent direction, slightly different that the prior pulse. Beam splitters or optical splitters may be used at any point along beam of pulsed laser light.

Another example of a beam manipulator (21) may include filters can be placed in a beam path to modulate or modify a property of a pulsed laser light, and may even reduce the net energy of a particular beam. A large number of filters may be used in series or even in parallel across many different beams of pulsed laser light.

A radiation emitter (12) or even a intermittingly punctuated radiation emitter may be embedded in an integrated fashion into a particle analysis or particle separation system. Alternately, with respect to some embodiments of the invention, a pulsed laser source may be independent and splitters, as described above, may be used to split an original beam of light to provide illumination light to numerous independently operating particle analysis components.

It is understood that a fundamental unit of illumination may be one single pulse of a laser light, and that each pulse or laser light may be split numerous times. Through splitting, filtration or even both, a net energy of any given pulse illuminating a biological object or sample may be perhaps as small as a single photon of light or perhaps as large as an original pulse energy emitted from a laser unit.

It is also understood that the use of splitters, which can divide laser light beams into two or more beams, may increase the number of light beams that can illuminate particles, such as biological objects. In embodiments, a number of pulsed light beams per second that can be directed toward particles can be multiplied with a splitter. It is also understood that the pulses per second may be altered to a desired number of pulses per second, timing of the pulse, and even position the pulse. A pulsed light may be distributed by an apparatus to possibly millions of particles or particle sample(s) which may be located in different positions. Through the use of harmonically synchronized oscillations, rotations, and even geometries, many pulses per second may be delivered to the same particle, sample, or even biological objects. It is particularly understood that, in embodiments, systems may be established with recurring illumination events.

Figure 3:
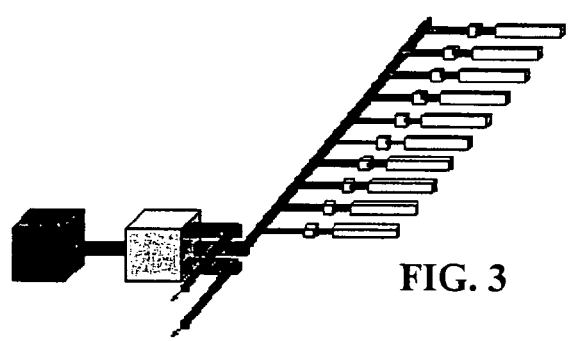
FIG. 3 represents a fluidically connected system according to certain embodiments of the invention.

An embodiment of the present invention may include a system fluidicly connected system, such as a flow cytometer system, as seen in FIG. 3. This may be representative of a multiple number of flow cytometry systems that are linked as one system.

Radiation emitters and even intermittingly punctuated radiation emitters, as described in more detail below, may provide one, two, three or perhaps even more radiation beams having specific frequencies, wavelengths, intensities, and even watts to illuminate the type of particles to be analyzed. An intermittingly punctuated radiation emitter may multiply subject radiation to, for example, sperm cells for a first amount of time and may multiply terminate radiation of sperm cells for a second amount of time (41). This may be represented by FIG. 4.

In embodiments, a first amount of time (40) may include an amount of time radiation occurs and this time may be between about 5 to about 20 picoseconds. A second amount of time (41) may be a radiation off time and may be between about 0.5 to about 20 nanoseconds. Of course, other amounts of time for each of a first amount and a second amount of time may be used and all are understood to be included within the scope of this invention. A cycle of a first and second time may be understood as a repetition (42). Each repetition may include a time of about 2 to about 10 microseconds, yet the repetition may vary. In embodiments, a repetition rate may include between about 50 to about 200 MHz and may even include a rate up to about 80 MHz. Other repetition rates are possible and all are meant to be included within the scope of this disclosure. In embodiments, a radiation emitter may be a Nd:YAG, Nd:YVO$_4$, or the like radiation emitters.

Figure 4:
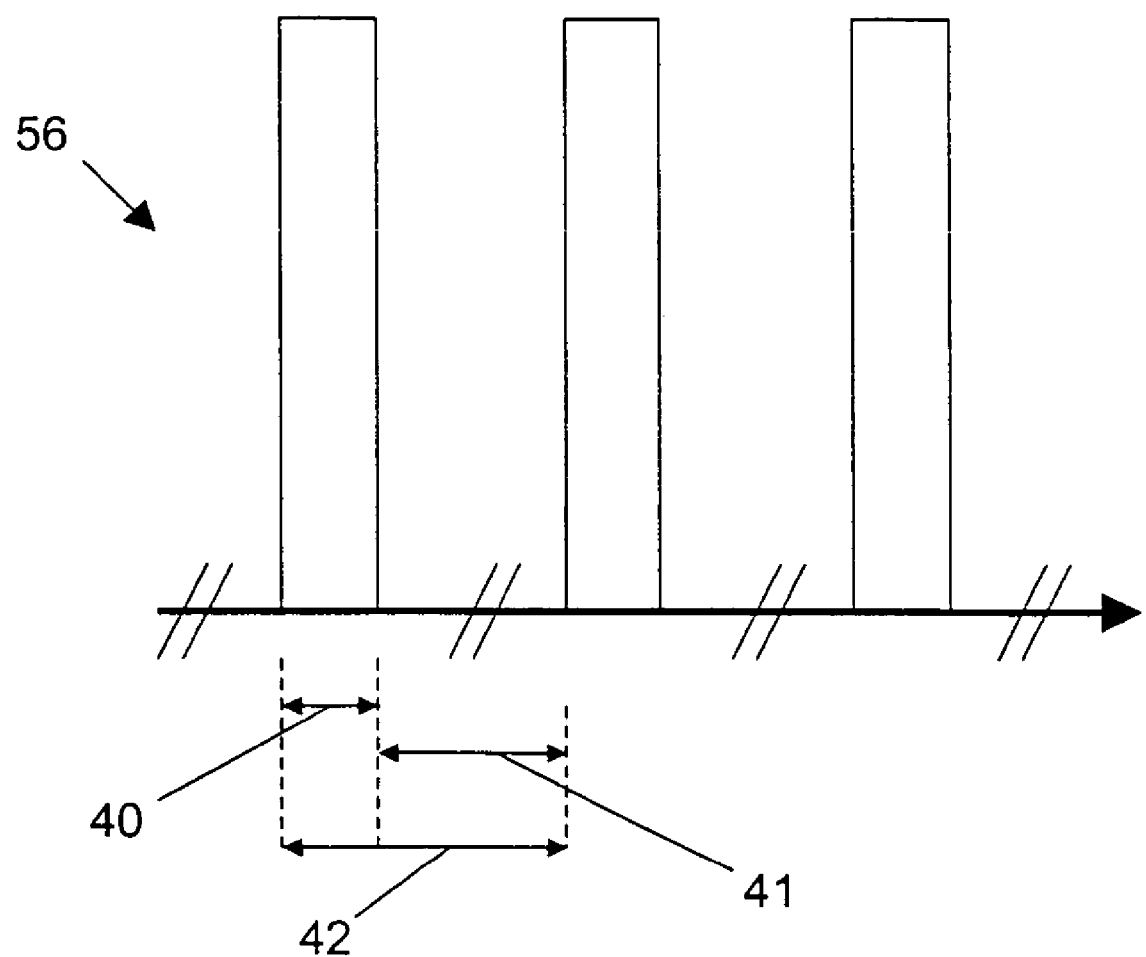
FIG. 4 is a simplified representation of a representative pulse of radiation that may used in some embodiments.

FIG. 4 shows parameters taken into consideration when discussing the differences between continuous wave (CW) lasers or even gas and pulsed lasers or even solid state lasers. As shown by FIG. 4, an intermittingly punctuated radiation emitter (56) may emit radiation that may not be continuous, yet be in short regular pulses which may have a duration time or a first amount of time (40). Following a pulse, there may be a dark period or a second amount of time (41) in which no light may be generated. The total elapsed time between two pulses, a repetition rate, may therefore be the duration time in addition to the dark period. A pulse line width and dark period may be similar in length, and it could be postulated that a laser may actually be illuminating a sample for somewhat less than "half of the time". Alternatively, a pulse line width may be much smaller than a dark period, and thus a sample may be illuminated for only a very small fraction of the time.

Peak energy (36) and a full amount of energy or joules delivered from one pulse of laser light is represented in FIG. 5. Fractional amounts (37) of that energy can be split as described above or put through a neutral density filter. Importantly, one may diminish the amount of light in one pulse used to illuminate a particle by dividing or filtering the beam. For example, a 350 mW beam can be split into 10 equal beams of approximately 35 mW to run 10 independent analysis machines from a single source laser. In practice, the quality of analysis at 35 mW must afford information regarding the characteristics of the particle illuminated, and for commercial applications perhaps afford at least the same amount of information as when particles illuminated with a CW UV laser running at the standard of 150 mW. FIG. 5 may further help in an understanding of the block diagram represented in FIG. 4. Each radiation pulse may be reduced in energy as previously discussed.

An energy density or even watts may be needed to achieve maximum light emission (38) from a particle upon illumination as shown by FIG. 6. It has been contemplated that light input of a continuous wave laser, however, may be so low that a particle may never be fully saturated with illumination (43). An emission light (44) from particles illuminated by a CW laser at a given energy intensity may be constant, as the source light may be constantly refreshing the particle to a certain partial saturation value. By comparison, emission light (39) from the same particle which has been illuminated with pulses may be greater than from a CW laser. Pulses may be short and may have illumination light intensity many orders of magnitude higher than the illumination level of a CW laser. It has also been speculated that a fate of light emission from a particle or particle sample(s) during the dark period may be dependent upon the half-life of emission for the illuminated particle and may even be dependent upon the length of time of the dark period. In the case where a half life may be as long or longer than the dark period, the emission could remain close to maximum during the entire time across all pulses delivered to the sample.

It should also be pointed out that if instead of reducing the input energy by splitting or filtering, one instead uses movement of mirrors and reflectors, one may reduce the number of pulses delivered to a biological sample to as low as one pulse, while retaining the very strong intensity of the pulse. Thus, it is a unique aspect of the invention to provide movement of the full strength pulsed laser beam across a plurality of particles which may for example be entrained in a fluid stream which passes through a flow cytometry nozzle or located on an array or matrix (such as a DNA or protein microarray), or a combination of both, as would be the case of a single laser being oscillated so that it illuminates a small number of flow cytometry nozzles in close proximity.

Now referring primarily to FIG. 8, irradiatable sperm cells may be introduced through a sperm sample injection element (4) which may act to supply irradiatable sperm cells for flow cytometry analysis. Irradiatable sperm cells may be deposited within a nozzle (5) in a manner such that the particles or cells are introduced into a sheath fluid (3). A nozzle may be located in part below an injection point of sperm cells. A sheath fluid (3) may be supplied by a sheath fluid source (46) through a sheath fluid port (2) so that irradiatable sperm cells and sheath fluid may be concurrently fed through a nozzle (5). Accordingly, the present invention may provide establishing a sheath fluid and flowing a sheath fluid into a nozzle, and injecting irradiatable sperm cells into a sheath fluid as shown in FIG. 8.

Further, in embodiments, the present invention may include subjecting irradiatable sperm cells radiation. Radiation may be produced from a radiation emitter (12) as discussed previously. In embodiments the radiation emitter may be a intermittingly punctuated radiation emitter or may even be a continuous wave laser.

In embodiments, the present invention may include multiply subjecting sperm cells to radiation having a wavelength appropriate to activate fluorescence in a sperm cell. The invention may include a fluorescence activation wavelength. Such wavelength may include about 355 nm. Of course, this may include any wavelength that may be needed to activate fluorescence. Such other wavelengths may include 350 nm, 360 nm and other wavelengths and all are meant to be included within the scope of this disclosure.

In embodiments, the present invention may include sufficiently hitting a sperm with radiation to cause an irradiatable sperm to emit fluorescence. This may include providing radiation at certain wavelength, power, energy and the like that is enough to cause an irradiatable sperm to emit fluorescence.

In embodiments, the present invention may provide for exciting irradiatable sperm cells that have been subjected to radiation. When in an excited state, the cells may emit fluorescence. In embodiments, irradiatable sperm cells may be multiply excited with radiation. This may include radiation that is emitted from a intermittingly punctuated radiation emitter.

A pulse of laser light may illuminate particles or even a particle sample(s) at a specific location with an EMR frequency or Hertz, timing such as a clock, intensity or even watts, and even net energy or joules. The particles may absorb the pulsed light, may get excited and may even emit light of the same frequency as that of the pulsed laser light, such as a scatter or may even emit a light of a difference frequency or even fluorescence. The exact nature of the amount of energy absorbed by a particle may be related to the chemical properties of the particle, the chemical properties of any objects attached to or closely associated with the particles, the physical chemical properties of the particle environment, such as biological segregations including membranes, organelles, solutes, pH, temperature, osmolality, colloidal character, or the like, and may even be related to the frequency and intensity of the laser light illuminating the particle. An EMR light emission from a particle, characterized by a wavelength and quantity, can provide highly accurate information about the status of a particle when a pulse of illuminating light is incident. Depending on the nature of the particle and the particle environment, the particle may then emit a florescent light signal, and may do so over a certain period of time defined by a half-life of emission. Typically, a number of pulses of laser light can illuminate a particle or particle sample in a specified period of time, and there can be a corresponding dynamically changing emission of light over the same period, or a time period after illumination.

Emitted fluorescence from each of the sperm cells may be detected with a detection system (23). A detection system may include a fluorescence detector (7) which may be connected to a processing unit (15). While processing the emitted fluorescence, the present invention may include evaluating the emitted signals. Evaluation of emitted fluorescence may include how much fluorescence may be emitted possibly by comparison between the cells or may even possibly be compared to a predetermined number. The present invention may include, in embodiments, selecting an electrical condition to be associated with each of the sperm cells in a sheath fluid flow. An electrical condition may be a charge, voltage or any electrical condition. A drop charge circuit (8) may charge a stream of cells and sheath fluid based upon deduced properties of each of the excited cells. For example, this may be to charge all of the X-chromosome bearing sperm cells with a positive charge, and charging all of the Y-chromosome bearing sperm cells with a negative charge. Of course, while the disclosure focuses primarily upon sperm cells, other particles may be analyzed as discussed in the various embodiments disclosed.

A charged drop may be formed and isolated in a free fall area. A drop may be based upon whether a desired cell does or does not exist within that drop. In this manner the detection system may act to permit a first and second deflection plates (18) to deflect drops based on whether or not they contain the appropriate cell or other item. The deflection plates may be disposed on opposite sides of a free fall area in which a drop may form and the deflection plates may be oppositely charged. As a result, a flow cytometer may act to sort cells by causing them to land in one or more collectors. Accordingly, by sensing some property of the cells or other items, a flow cytometer can discriminate between cells based on a particular characteristic and place them in the appropriate collector. In some embodiments, X-bearing sperm droplets are charged positively and deflected in one direction, and Y-bearing sperm droplets are charged negatively and deflected the other way. A wasted stream which may be unsortable cells may be uncharged and may be collected in collector, an undeflected stream into a suction tube or the like.

In this manner, a sheath fluid may form a sheath fluid environment for the sperm cells to be analyzed. Since the various fluids are provided to the flow cytometer at some pressure, they may flow out of nozzle (5) and exit through a nozzle orifice (47). By providing some type of oscillator (6) which may be very precisely controlled through an oscillator control (45), pressure waves may be established within the nozzle and transmitted to the fluids exiting the nozzle at nozzle orifice. Since an oscillator may act upon the sheath fluid, a stream (19) exiting the nozzle orifice (47) can eventually and regularly forms drops (9). Because the particles or cells are surrounded by the fluid stream or sheath fluid environment, the drops (9) may entrain within them individually isolated particles or cells, such as sperm cells with respect to some embodiments of the invention.

In other embodiments, since the drops can entrain particles or cells, the flow cytometer can be used to separate particles, cells, sperm cells or the like based upon particle or cell characteristics. This is accomplished through a particle or cell detection system (23). The particle or cell detection system involves at least some type of detector (7) which responds to the particles or cells contained within fluid stream. The particle or cell sensing system may cause an action depending upon the relative presence or relative absence of a characteristic, such as fluorochrome bound to the particle or cell or the DNA within the cell that may be excited by an irradiation source such as a radiation emitter (12) generating an irradiation beam to which the particle can be responsive. While each type of particle, cell, or the nuclear DNA of sperm cells may be stained with at least one type of fluorochrome different amounts of fluorochrome bind to each individual particle or cell based on the number of binding sites available to the particular type of fluorochrome used. With respect to spermatozoa, the availability of binding sites for Hoechst 33342 stain is dependant upon the amount of DNA contained within each spermatozoa. Because X-chromosome bearing spermatozoa contain more DNA than Y-chromosome bearing spermatozoa, the X-chromosome bearing spermatozoa can bind a greater amount of fluorochrome than Y-chromosome bearing spermatozoa. Thus, by measuring the fluorescence emitted by the bound fluorochrome upon excitation, it is possible to differentiate between X-bearing spermatozoa and Y-bearing spermatozoa.

As a result, the flow cytometer acts to separate the particle or cells by causing them to be directed to one or more collection containers. For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus is collected in an undeflected stream into a suction tube or the like as discussed in U.S. Pat. No. 6,149, 867 to Seidel, hereby incorporated by reference herein. Naturally, numerous deflection trajectories can be established and collected simultaneously.

Irradiatable sample cells may include a sample cell that is capable of emitting rays of light upon illumination. This may or may not include having stain molecules attached to a sample particle. Some particles may have features that allow them to emit fluorescence naturally without having to add a stain to them.

Laser light incident upon the particle(s) being analyzed may generate at least one, or perhaps even two, three or more beams of scattered light or emitted light having specific frequencies, wavelengths, intensities and perhaps even watts. All or a portion of the scattered light or even emitted light may be captured by a detector. A detector may include a photomultiplier tube or the like detectors.

A detection system may be used to detecting an amount of emitted fluorescence from each of the sperm cells in a flow cytometry system. A detection system or even a sperm cell fluorescence detector may include a photomultiplier tube. In other embodiments a detection system may include an optical lens assembly, a photomultiplier tube and even some sort of analysis system such as a computer. An optical lens assembly may collect emitted fluorescence and transport a collected signal to a photomultiplier tube. The signal detected by a photomultiplier tube may then be analyzed by a computer or the like devices.

A single or perhaps even a multiple digital or analog detector(s) may receive all or even a portion of the scattered light or emission light. Analog or digital processor(s) may convert the signals detected by the detector(s) into analog current or even digital information. The information may accurately represent the identity, frequency, quantity, and even joules of light or EMR received by the detector.

In embodiments, a detector may generate a current or digital signal corresponding to the amount of light quanta hitting the detector. Certain embodiments of the invention, can provide a one dimensional detector which summates all light of the specified wavelength incident upon the detector surface during a specified period of time. The duration or even a total time of detection may be as simple as a fully additive collection or even integration over an entire analysis time of the sample, or it may be a dynamic data set which may record an emission of light from a biological object(s) or sample(s) over a time period. That time period may be as short as the time between two pulses of the pulsed laser light, or it may be as long as many millions of pulses. It is understood that such a detector may become two dimensional when the second dimension of time is considered.

In other embodiments, a two or three dimensional detector may comprise a flat panel, a three dimensional matrix of unit cells or even pixels which can detect an emission light once or more times and can record or report the interaction specific to that individual unit cell. The information relevant to the operator of an apparatus may be a summation or display of the results of many unit cells. This type of detector may include, but is not limited to, photographic film, photographic paper, or even a microchip capable of sending data for imaging on a television screen or computer screen. It is understood that a two dimensional detector may become three dimensional, and three dimensional detector may become dimensional when the additional dimension of time may be considered.

A signal generated by a detector can be processed to provide simple outcomes such as photos. A signal generated by a detector may even be able to allow analysis of many thousands or even millions of biological objects in real time with computer graphics which can give representations to allow a user to modulate or modify an analysis process in real time. In other embodiments, it may be desirable to sort with a magnetic detection.

In embodiments, the present invention may include quantitatively detecting an amount of emitted fluorescence from each of the sperm cells. The quantity of the emitted fluorescence may be detected with a sperm cell fluorescence quantitative detector. Of course this may include other samples. In sperm cells, a X chromosome bearing sperm and a Y chromosome bearing sperm may be distinguished because an X chromosome bearing sperm may emit a different amount of fluorescence than a Y chromosome bearing sperm. In other embodiments, if using other samples besides sperm cells, the present invention may provide distinguishing between a first population of particles and a second population of particles due to a difference in an amount of fluorescence emitted from each population of particles. A distinguishing analysis may be calculated with a detector.

Operating system controlled computer(s) or even graphic user interface controlled computers may use data from an analog or even digital processor(s). A computer may facilitate direct feedback control of a laser and even analytical equipment. A computer may even provide data to support a workstation which may give an operator(s) of an analytical or separation equipment images that may relate to a behavior of the system. This may allow control of the behavior of the system for optimal analysis, quantification, and even separation of a biological object(s) or even a sample(s).

Auxiliary computational, command equipment or even control equipment may provide local network control of analysis, quantification and separation apparatus. Control equipment may communicate in local area networks (LAN) or even wide area networks (WAN) to provide local or perhaps even distant operators capability to initiate, monitor, control, troubleshoot, download data or even instructions, upload data or instructions, terminate, and the like. Control equipment may allow operation of one, two, three or even more apparatus.

Computational subcomponents may correspond to a command and even a control which may be integrated into a pulsed laser design and construction. In some embodiments, computational subcomponents may be independent or even integrated parts of an apparatus and may reside outside a housing of a pulsed laser.

In embodiments, the present invention may provide staining a sperm cell with a fluorescent dye. A stained sperm cell (or in other embodiments, a stained sample) may be stained with fluorochrome and in yet other embodiments, may be stained with Hoechst bisbenzimide H33342 fluorochrome.

In some instances, a large amount of dye may be used to stain a sperm cell. Sperm cells contain deoxyribonucleic acid and deoxyribonucleic acid may have many binding sites that stain (dye) molecules may bind with. Due to the nature of sperm cells, a stained sperm cell may have many molecules of a dye attached to each binding site of a sperm.

In embodiments, the present invention may include staining a sperm sample for a reduced staining time. The staining time may vary due to the type of stain used and even due to the type of sample used, here sperm. Typically, staining sperm with Hoechst 33324 may take about 40 minutes. under other constant conditions. Some examples of a reduced staining time may include the following:

less than about 40 minutes.
less than about 35 minutes;
less than about 30 minutes;
less than about 25 minutes;
less than about 20 minutes;
less than about 15 minutes;
less than about 10 minutes; and
less than about 5 minutes.

Of course, other stain times are certainly possible and all should be understood as represented within the scope of this invention.

In embodiments, the present invention provides distinguishing between a X chromosome bearing sperm and a Y chromosome bearing sperm in a flow cytometer system. A X chromosome bearing sperm may emit a different fluorescence from said Y chromosome. For example, a X chromosome bearing sperm may contain more DNA than a Y chromosome bearing sperm, thus a X chromosome bearing sperm may bind to more dye. When illuminated, a X chromosome bearing sperm may emit a greater fluorescence than a Y chromosome bearing sperm. The difference may provide the ability to distinguish the two chromosome bearing sperms.

The present invention may include, in embodiments, minimally staining sperm cells with a fluorescent dye. A minimum sperm stain may include allowing less stain to bind to each sperm. For example, it may take a certain amount of stain to complete attach stain molecules to each binding site of a sperm cell. It may be an efficient option if less amount of stain could be used while maintaining the ability to achieve a desired result, such as the ability to distinguish between two different cells after radiation. In embodiments, the present invention may include providing a percentage of stain. While a percentage of stain may be as low as 10%, other examples may include about 90%, about 80%, about 70% and about 60%. All stain percentages are understood as included within the scope of this disclosure.

A benefit with respect to sorting sperm cells using a pulsed laser can be a reduction in the amount of stain taken up by sperm cells during staining. Because stains or dyes, such as Hoechst 33342, bind with DNA within sperm cells, stain has been considered a factor detrimental to the viability or fertility of sperm cells. Using a pulsed laser flow sort invention, the amount of stain taken up by sperm cells during staining can be reduced by 20% over the amounts used with conventional CW laser cell sorting technology with similar or better resolution of X-chromosome bearing and Y-chromosome bearing subpopulations. In certain sperm cell samples the amount of stain taken up by the sperm cells can be reduced to as little as 60% of the amount used with the same cells sorted by conventional CW cell sorting technology.

Any kind of sample or particle may be used in a flow cytometry system. A sample may include usable cells, reproductive cells, haploid cells, sperm cells, delicate sample, non-biological particles, biological particles, or any kind of cell that can be used with a flow cytometer system. A useable cell may be a cell that can be used for further processing or analysis after completion through a cytometry system. Specifically, in embodiments, this may include providing a viable cell. Reproductive cells may include cells that can be used to reproduce an organism or even a mammal and the like. Haploid cells may include those cells that have a single set of chromosomes, such as sperm cells. A delicate sample may include a sample that is fragile or may even be easily damaged such as reduction in viability. A delicate sample may have increased sensitivity to certain environments such as the type of stain, the sorting process and other environments.

Particles can be non-biological particles such as plastic beads, biological particles such as diploid cells, haploid sperm cells, or the like. It is to be understood that particles are not limited to cells or beads but can also include other non-biological particles, biological particles, and the like. Particles may include, without limitation: the individual binding sites or attachment sites of a molecule on the surface of a cell or other molecule; large molecules (possibly whether on the surface of a cell or within a cell) such as proteins, single stranded DNA, double stranded DNA, mRNA, tRNA, DNA-RNA duplexes, combined protein nucleic acid structures such as a ribosomes, telomerases or the like, DNA or RNA polymerases, samino acid synthetase; the active site of an enzyme such as luciferase, peroxidase, dehydrogenase or even cytochrome oxidase which may require cofactors such as ATP, NADH or NADPH; free or bound hydride (H—); or even any structure biological or non-biological that can be entrained in a fluid stream and made incident to an illumination beam to generate scattered light or even emission light.

In another embodiment that may contribute to efficiency in a flow cytometry system, the present invention may include subjecting sperm cells to low power radiation. While the range of power that may be used with a flow cytometry system may vary, some possibilities for low power may include:
less than 300 milliwatt;
less than 350 milliwatt;
less than 200 milliwatt;
less than 175 milliwatt;
less than 100 milliwatt;
less than 88 milliwatt;
less than 50 milliwatt; and
less than 25 milliwatt.

Again, other powers of radiation are certainly possible and all should be understood as represented within the scope of this invention.

In some examples, a Vanguard Laser may be used. The Vanguard Laser is manufactured by Spectra-Physics and can emit 80 million pulses per second (80 MHz). *LaserForefront*, Spectra-Physics, No. 30 (2001). Each pulse may have line width of about 12 picoseconds, and a repetition rate of about 10 nanoseconds. This may mean that to an approximation, during a single repetition of 10 nanoseconds, the pulsed laser may illuminate a target for about 12 of 10,000 picoseconds or about 0.12% of the total time. In other words, a sample being illuminated by a pulsed laser may be spending approximately 99.88% of the time in the dark. This may also mean that since a pulsed laser may be delivering 350 milliwatts (mW) of total power, during the short 12 picosecond pulse, an average of 280 Watts may be delivered to a particle. This may be 800 times more intense than a light from a continuous wave (CW) laser running at 350 mW. Since reliable sperm sorting can be performed at 150 mW on a standard CW UV laser, which may represent a factor of 653 fold, it could be hypothesized that it may be possible to run a pulsed laser at as low as $^{150}/_{650}$ or 0.23 mW and still have light intense enough to illuminate a sperm.

In embodiments, the present invention may include utilizing at least one shared resource to process sperm cells. This may help in efficiency of sperm sorting in flow cytometry systems. A shared resource may include a computer system, a sheath fluid, an integrated multiple nozzle device, and the like. In embodiments, a shared resource may include utilizing one radiation source. Radiation may be split into at least two beams and each beam may be directed toward a nozzle and the sample being sorted. In embodiments, the present invention may include one radiation emitter and a beam splitter or may even include one intermittingly punctuated radiation emitter and a beam splitter. A beam splitter may be any kind of beam splitter as previously discussed.

As discussed above, the use of refractive, or semi-reflective splitters provides multiple beams of pulsed laser light derived from the original source light. These beams may have diminished intensity from the original beam, but may be able to each be used to analyze separate particles or particle sample(s). Also discussed above, each beam may be dedicated to an independent analytical or analytical/separation device (for example, but not limited to, a sperm sorting flow cytometer or cell sorter). In some embodiments of the invention, each light beam corresponding to an independent instrument can be split into two light beams of equal intensity and one light beam made incident upon the particle to be analyzed, and the other light beam can provide a reference beam. By comparing the two beams, the absorption of source light by the particle may be measured. Another unique and important attribute of using a single pulsed laser to supply light to dozens or hundreds or thousands of independent analysis or separating machines may be that the entire complex of instruments served by the single light will be using the same light, and to the extent that all machines are performing identical or highly similar activities, it is possible to use the data from all machines as internal references and standards to each other, and by using computers or both which can give local (LAN) as well as distant (WAN) access to the data, to allow operators or persons at a distance to monitor the performance of each machine in real time.

While multiple nozzles may be integrated into one device, separate flow cytometers having only one nozzle may be lined up so that radiation may be directed to or even split between each nozzle.

In embodiments, the present invention may include flowing at least one sheath fluid and sperm cells into at least two nozzles. By multiplying the number of nozzles operating on a single flow cytometer, the amount (number of particles) analyzed and sorted per unit time may be increased. In the case where the operation of the flow cytometer may be in a production setting representing a saleable product, multiple nozzle may increase the number of units produced in a single shift by a single operator, and thus a reduction in the costs of each unit produced.

By operating a number of nozzles on the same device, a controlling instrumentation used on the flow cytometer and operators of the flow cytometer may use statistical analysis of the performance (operation data) of a multiple of nozzles and may use this data for feedback control of single nozzles within the population of the nozzles being used. By operating a number of nozzles on the same device, a single light source providing a multiple of beams (one or more for each nozzle) may reside on the same mounting as the nozzles and thereby reduce the complexities of light paths related to nozzles running on individual mountings, which may be independent of the mounting of the primary illumination source. By operating a number of nozzles on the same device illuminated by multiple beams from a single light source providing the capital, operating, parts, service, and maintenance costs from a single laser may be distributed across a multiple of productive sorting nozzles, and, therefore, reduce costs per unit produced which are allocated to the laser operation.

FIG. 7 shows multiple nozzles (5) which can provide charged drops (9). The multiple nozzles and collector (20) may be arranged so that a number of selected containers may be less than a number of nozzles. Selected containers may include containers having collected one specific type of cell, such as all the X chromosome bearing sperm cells. In this figure, the sorted X chromosome sperm cells may be represented by the containers (32). Here there are three selected containers of a selected cell that have been sorted from four nozzles.

In other embodiments, the present invention provides utilizing collected sorted sperm for insemination of female mammals and may even provide for a mammal produced through use of a sorted sperm cells produced with a flow cytometer system according to any of the embodiments as presented in this disclosure.

In other embodiments, the present invention may include individually controlling or even compositely controlling at least two nozzles. Each nozzle may individually adjusted according to a desired function with an individual nozzle control, or a plurality of nozzles may be adjusted compositely with a single nozzle control device that may be connected to each of the nozzles.

Another way to increase efficiency in a flow cytometry system, the present invention includes rapidly sorting said sperm cells. This may be achieved with a rapid sperm sorter or even a rapid particle sample sorter. Sperm may be sorted at any rate. Such possibilities for a sort rate may include:
 greater than 500 cells per second.
 greater than 1000 cells per second;
 greater than 1500 cells per second;
 greater than 2000 cells per second; and
 greater than 3000 cells per second.

Other sort rates are certainly possible and all should be understood as represented within the scope of this invention.

In embodiments, the present invention may include a particle sample collector such as a sperm cell collector. A collector may be multiple containers, a combined collector having individual container, or any type of collector. For example and as shown in FIG. 9, a combined collector (63) may include a collector for one type of particle (32), such as X chromosome bearing sperm populations, a container for a second type of particle (33) such as Y chromosome bearing sperm populations, and may even have a third container (64) to collect those drops which may not have been charged.

It may be important in designing illumination beams to consider that the closer the illumination source (laser) may be to an analysis point, the less effect any form of movement such as vibrations may have on the path of the beam. It may be desirable to provide an system which reduces the distance between and location of all nozzles to within a very small distance of each other (for example all within 15 cm), and greatly simplifies and enables the use of multiple beams from a single laser light source.

FIG. 9 shows an exploded diagram of components of a flow cytometry system combined into a parallel construction where a multiple of nozzles may be operated on a single apparatus. Although the diagram depicts six nozzles, it is exemplary, such that it might as easily have only 2 or 3 nozzles, or may have as many as 8 or 10 or 12 or even 24 nozzles side by side.

A multiple of incoming laser beams or radiation (11), which in most embodiments could be equal beams derived by splitting from an original source beam located close to the nozzles, shines onto an analysis point which is defined by the intersection of the beam or radiation (11) with a narrow stream of fluid which emits from the nozzle (5). In some embodiments, the analysis point may be at the focal point (60) of a reflective parabolic dish (61) which may reflect emitted light (62) up to the detection surface (58). Unabsorbed laser light which may not be absorbed may be absorbed by a heat sink, or it may be measured by an additional detector to determine an exact real time intensity of the beam. Each nozzle may be equipped with an oscillator (6) which may provide a force causing the stream emitting from the nozzle tip or orifice (47) to break into droplets at defined frequencies such as in the 10,000-100,000 Hz range. Droplets may be charged, and by action of a magnetic field may be separated. In the case of sorting live mammalian sperm for the presence of X or Y chromosomes, there can be 3 streams of droplets: a stream containing primarily X chromosome bearing sperm, which may by example be collected in one container (32) on one side of a collector (20), a stream containing primarily Y chromosome bearing sperm, which may by example be collected in another container (33) on the other side of a collector (20), and a stream containing sperm which may be dead and which may be collected a third container (64) in the middle of a collector (20). In other embodiments, features such as a detection surface (58), parabolic dishes (61), collectors (20) and in some embodiments nozzles (5) and oscillator(s) (6), may be fabricated into single parts or group subassemblies, which may be sandwiched together to manifest the actual sorting nozzle architecture.

In other embodiments of the present invention, detection surfaces may have diameters (57) similar to the diameter of microtiter plate wells, which can be about 5-8 millimeters, and can have distances (59) between two neighboring flow cytometry nozzle tips which are equal to the distance between two wells, which may be about 12-18 mm.

Now, referring primarily to FIG. 10, certain time intervals and light energy quantities which may be derived from the particular properties of light provided by a pulsed laser are shown. The standard lasers used in most flow cytometry and particularly in sperm sorting have been ion tube continuous wave (CW) lasers which emit a fairly constant light flux, pulsed lasers may deliver the same rate of net light. For example, as watts is defined as joules per second, we may consider the period of 1 second. It may be exemplary that for many applications in flow cytometry, as many as 10,000-100,000 individual events may be analyzed in 1 second, so that each event requires illumination energies of approx $\frac{1}{10,000}$-$\frac{1}{100,000}$ joules.

In contrast, the pulsed laser may emit the same net light in regular pulses. In FIG. 15, which represents an arbitrary time axis, each pulse of laser light (68) can emit a certain energy, and have a certain illumination pulse duration. When a pulse may illuminate a particle, a fluorescent emission pulse may occur from that particle which can be represented by an emission curve (65). An emission curve can represents a classic exponential decay function where maximum emission is at the start and the rate of emission (decay) is along a corresponding half life curve. Based on some definition of final decay, for example to the point where emission is $\frac{1}{1000}$ of original emission, or about 10 half lives, an emission pulse duration (67) can be established. There may also be a period commencing from the final decay point occurring at the end of the time summated by illumination pulse duration and emission pulse duration (67) and the beginning of the next illumination pulse, which can be defined as the resting period. The total sum of these periods may the period between pulses which may be the interpulse period and is typically the inverse of the frequency of the laser.

Using a detection surface, it may be possible to analyze the light output emitted from a particle emission pulse and specifically measuring the summated total of energy from the emission pulse, which may be an integration of the area (66) under the decay curve (65). This measurement (70) may be stored as an analog electrical charge in a charge storage device such as an appropriate capacitor, of it may be converted to a digital value (70) which can be stored in a digital memory device. Given that the emission pulse occurs as a dynamic emission event, which through a photodiode/amplifier system may be translated in realtime to an electrical current (or voltage differential), measurements of current or voltage at multiple points during the particle emission may allow the derivative of the decay curve to be determined (71). These can be useful values in statistical analysis of multiple identical illumination events of the same particle.

In flow cytometry, which is a broad field in which the instant invention may be used, particles which are being illuminated by a laser are commonly flowing in a fluid stream or a flow cell past a fixed point upon which a laser beam is focused. In FIG. 11, a rate of flow of particles past the point of illumination can be a function of the volume flux of the stream, and the concentration of the particles. An illumination period (72) of time in which the particle is being illuminated may be determined by the flow rate and the size of the particle in the direction of the flow. When the particle may be illuminated by a pulsed laser generating individual emission pulses (73) which can occur in interpulse periods much less than the illumination period (72) of the particle, then a large number of individual emission pulses may be derived from the particle (74). In contrast, when a particle may be illuminated during the same period by a continuous wave (CW) laser, there may be a long emission over the period (75), which can commonly be detected as a peak profile of current over the period. A measurement of the emission from particles illuminated by CW lasers are a single long analog events without natural internal cut points and so either the entire value may be integrated, or the event may be sampled at a discreet multiple of times, or segments of the event are integrated.

In other embodiments, lasers may be used where the illumination pulse duration may be much smaller than an interpulse period which may itself be much shorter than the particle illumination period (72). For example, when the Vanguard Laser is used for the sorting of sperm at approximately 25,000 events per second, the laser which has 80,000,000 illumination pulses per second will deliver approximately 3000 pulses per event, and about 5-10% or 150-300 pulses occur in the particle illumination period (72). Also, the pulse duration is about 10 picoseconds ($10^{-11}$ sec), the interpulse period is about 10 nanoseconds ($10^{-8}$ seconds), and the pulse emission period is less than 1 nanosecond.

As may be understood from FIG. 12, an illumination pulse may initiating a sensing routine. The instant invention may use a laser pulses as an internal clock to the entire analysis system. Advantages are that each illumination pulse, which is very brief and very strong, can be used to initiate each clock cycle. Within a single clock cycle, a computational subroutine may run which uses the resting period to calculate specific values for each illumination/emission event, and cache the result prior to the initiation of the next clock cycle. An analysis of individual particles could be manifested over a multiple of clock cycles (for example 150-300), such that statistical analysis of all emission events mapping to a single particle may occur, and averaged values related to the measurement of the quantity particle and the position of the particle may be cached. The period between a multiple of events, which may be dominated by periods without emissions, may be used to map the identity and distances and using the momentary gating criteria to effect the sort. Values of operating parameters and results within each sort may be cached for viewing at the 1 minute level, possibly operator status, and graphic or summations for entire sort runs may be generated. In FIG. 17, using the example of sperm being sorted using a Vanguard Laser, the clock cycle may be about $10^{-8}$ seconds. Each clock cycle encompasses three periods. The illumination pulse of $10^{-11}$ seconds, the emission period of $10^{-9}$ seconds, and the resting period of $9 \times 10^{-9}$ seconds. Each clock cycle (77) occurs approximately 300 times in each analysis event of $3 \times 10^{-6}$ seconds. Time between analysis events averages $2 \times 10^{-5}$ seconds. The time between each analysis and the sort (79) is approximately $5 \times 10^{-2}$ seconds. Operators will usually want to observe net historical data over the most recent minute (80) and be able to view the progress/history of data over the entire sample from start of sort (81).

There may be many hierarchical layers of data occurring dynamically. At the same time, with a number of nozzles all sorting the same sample at the same time, there are simultaneous events occurring in each nozzle at each hierarchical layer. As it would be labor intensive and inefficient for the operator to control each nozzle, the statistical analysis and algorithmic mapping should allow the operator to view status, history, and averages of all nozzles in aggregate and note only nozzles which are not functioning near the mean of the group. The operator also needs to use commands to change the sorting, which should effect all nozzles at one time.

The data may also be shared between control functions across multiple nozzles and over time to allow the system to make automatic adjustments such as: adjusting optical mirror positions to assure equal laser light in each beam; tracking the performance of each nozzle to make early identification of nozzle occlusion events; tracking the performance of each nozzle to identify differential flow rates and even comparing one or more semen samples with direct comparisons.

All of these various calculations, in real time, can be calibrated very precisely in time, as they may all use the very high frequency laser clock. Thus, in the parallelized flow cytometer, a pulsed laser may serve as an important integration component for all of the data being generated in a multiple of nozzles.

Referring primarily to FIG. 13, since it may be desirable to stain samples just prior to sorting, sorting a sample for a period of time before staining a second sample which may have been sorted and repeating this process several times may create samples which have been stained and sorted at different times, but may be pooled as a single batch. Aggregated data (82) for each sample may be compared across a multiple of nozzles and multiple of sorts (83), for example, from the same ejaculate of a certain bull. Comparisons of the same bull over multiple days (84) and comparisons between various bulls (85) can give a history. The data from this history may reside within the operating system and may be used to assist operators in choosing staining concentrations or times, or to help identify ejaculates which are sorting worse than their normal sorting. Also, if high-throughput resort analysis is available, predicted sex ratios versus. actual sex ratios may be determined, and the aggregated sex ratios may be compared to identify settings and methods which different operators may be using, or to identify operators who are consistently getting lower results. Also, trends in the sorting performance may become visible which dictate special maintenance such as cleaning of optics, replacement of nozzle, mirror assemblies, or the like.

Now referring primarily to FIGS. 14 through 18, embodiments of the invention are shown using a pulsed laser in the context of flow sorting of sperm cells. Various results from experiments run at different powers of radiation beams are shown. The different experiments included 20 mW, 60 mW, 90 mW, 130 mW and 160 mW power and each power was created using neutral density filters. These embodiments can provide high-purity sperm sorting for enrichment of X or Y-chromosome bearing sperm cells which can even be up to 98% in purity.

In yet other embodiments, the present invention may provide collecting at least two populations of sample particles, more specifically, collecting a sorted population of X chromosome bearing sperm and collecting a sorted population of Y chromosome bearing sperm. A collector may be provided to collect each sorted population. Accordingly, the present invention may include a X chromosome bearing sperm collector and a Y chromosome sperm collector. It may be important to sort and collect each population at a high purity. A high purity sorted population of X chromosome bearing sperm and said Y chromosome bearing sperm may include a percentage of purity. Of course, any percentage of purity may exist and some examples may include:

greater than 85% purity;
greater than 90% purity;
greater than 95% purity;
greater than 96% purity; and
greater than 98% purity.

Other percentages of purity are certainly possible and all should be understood as represented within the scope of this invention.

Typical pulsed lasers having characteristics similar to that set out by Table 1 or Table 2 can be used with the invention.

TABLE 1

| Vanguard 150 mW Output Power |
| --- |
| Average Output Power [W] |
| 0.15 |
| UV Beam Size [mm] |
| 1 |
| Energy per Pulse [J] |
| 1.875E−09 |
| Peak Power [W] |
| 234.375 |
| Power per cm^2 [W/cm^2] |
| 2.98E+04 |

TABLE 2

| Vanguard 350 mW Output Power |
| --- |
| Average Output Power [W] |
| 0.35 |
| UV Beam Size [mm] |
| 1 |
| Energy per Pulse [J] |
| 4.375E−09 |
| Power per Pulse [W] |
| 546.875 |
| Power per cm^2 [W/cm^2] |
| 6.96E+04 |

FIGS. 14 through 18 show univariate histograms and a bivariate dot plots from sorting of Hoechst 33342 stained bovine sperm cells. Sperm cells sorted were obtained from the same freshly ejaculated bull sperm diluted to 200×10$^6$ sperm cells per mL and incubated in Hoechst 33342 at 34° C. for 45 min.

With respect to the particular histograms and bivariant plots shown by FIGS. 14 through 19, the event rate (illumination of the sperm cells as they pass through the pulsed laser beam) was established at 20,000 events per second. The sort rate (separation of the sperm cells differentiated by analysis) into subpopulations was varied from 850-3500 depending on the power used. The results are also set out by Table 3.

TABLE 3

| Pulsed Laser Power Setting | Purity X % | Purity Y % |
| --- | --- | --- |
| 20 mW pulsed | 96.5 | 91.0 |
| 60 mW pulsed | 93.5 | 85.5 |
| 90 mW pulsed | 96.0 | 89.5 |
| 130 mW pulsed | 96.0 | 91.0 |
| 160 mW pulsed | 97.0 | 93.0 |

As can be understood from Table 3, using a pulsed laser sperm cells can be sorted into high purity X-chromosome bearing and Y-chromosome bearing subpopulations. For each laser power setting between 20 mW and 160 mW sorted subpopulations had a purity of up to 97.0% of the correct sex type.

Now referring primarily to FIG. 19, histograms compare the resolution of the same sample of sperm cells using conventional CW flow sorting technology and with an embodiment of the flow sorting invention utilizing a pulsed laser beam. Importantly, pulsed laser illumination of stained sperm cells provides superior resolution of X-chromosome bearing sperm cells and Y-chromosome bearing sperm cells. This is true even when the pulsed laser beam has a power significantly lower than the compared to conventional CW flow sorter technology. Even when the pulsed power is 130 mW, 70 mW or even $^{20}/_{150}$ of the power used in the compared to CW flow sorter technology. The histograms of the pulsed laser experiments show a cleaner separation of the two peaks as compared to the continuous wave experiments.

In embodiments, the present invention may include providing a high resolution of a sorted population of sperm cells. A higher resolution may be indicative of the purity of a sorted population. While many different resolution values may exist, some examples of high resolutions may include:

greater than 7.0;
greater than 7.5;
greater than 8.0;
greater than 8.5;
greater than 9.0; and
greater than 9.2.

Of course, other resolution values may exist and all are to be understood as represented within the scope of the invention.

As discussed above, lower laser power analysis of particles, and in this particular embodiment of the invention sperm cells, resolves the long standing problem of having to have a dedicated laser source for each flow sorter. By reducing the laser power required, even without achieving any other benefit, multiple flow cytometers, flow sorters, or cell sorters can be operated using a single laser source. For example, when sorting is accomplished at about 20 mW, a single 350 mW pulsed laser can be used to provide illumination light for as many as 18 separately functioning flow cytometers or flow sorters used to separate sperm cells on the basis of bearing an X or Y chromosome.

Again referring to FIG. 19, another important benefit provided by a pulsed laser invention in the context of sorting sperm cells can be increased resolution of X-chromosome bearing and Y-chromosome bearing subpopulations even when sperm cell samples, such as those used in this specific example, are stored for long periods of time at about 5° C., such as 18 hours or longer, or frozen and thawed prior to staining and analysis, the resolution of sorted sperm cells can improved with the pulsed laser invention compared to conventional CW laser technology.

In embodiments, the present invention may include sorting sperm cells at a low coincidence rate. Some examples of low coincidence rates may include:
- less than 4400;
- less than 4000;
- less than 3700; and
- less than 3600.

Again, other low coincidence rates are certainly possible and all should be understood as represented within the scope of this invention.

The present invention may include, in embodiments, collecting sorted populations of sperm cells at a high collection rate. A high collection may increase productivity and even efficiency. Some examples of high collection rates may include:
- greater than 2400 sperm per second;
- greater than 2600 sperm per second;
- greater than 2900 sperm per second;
- greater than 3000 sperm per second; and
- greater than 3100 sperm per second.

Other collection rates are possible and all are meant to be included within the scope of this invention.

In yet other embodiments, the present invention may include detecting sperm cells at an event rate of between about 10,000 to about 60,000 sperm cells per second. Of course, an event rate may be greater than 10,000 or even lower than 60,000 cells per second.

A benefit with respect to sorting sperm cells using the pulsed laser invention can be higher sorting speeds. When resolution of a particular sample is increased, the sort rate of subpopulations of sperm cells to a given purity can be increased.

Another benefit with respect to sorting sperm cells using the pulsed laser invention can be a higher purity sort. When resolution of a particular sample is increased, the purity of the subpopulations of sperm cells can be increased.

A pulsed laser invention may be understood to have application with respect to any particular particle characteristic which may be differentiated by change of illumination intensity or by detectable light emission upon illumination with a pulsed light beam. While the applicant has provided specific examples of differentiating the amount of DNA within a cell using the invention, it to be understood that these examples are illustrative of how to make and use the invention with regard to the wide variety of non-biological and biological particles, including, but not limited to, viral particles, polyploid cells, diploid cells, haploid cells (such as sperm cells obtained from any species of mammal such as any type or kind of bovine, ovine, porcine, or equine sperm cells; or sperm cells obtained from any type or kind of elk, deer, oxen, buffalo, goats, camels, rabbits, or lama; or sperm cells obtained from any marine mammal such as whales or dolphins; or sperm cells obtained from any rare or endangered species of mammal; or sperm cells obtained from a zoological species of mammal; or sperm cells obtained from a rare or prize individual of a species of mammal; or sperm cells obtained from an individual of a species of mammal that used to produce dairy or meat products. In embodiments, sperm cells may include any type of sperm cells such as but not limited to, mammals, bovine sperm cells, equine sperm cells, porcine sperm cells, ovine sperm cells, camelid sperm cells, ruminant sperm cells, canine sperm cells and the like.

It is understood that the present invention may exist in unique advantages when combined with other aspects of the various references incorporated.

It is also to be understood that these specific examples provided are not intended to limit the variety of applications to which the invention may be used, but rather are intended to be illustrative how to make and use the numerous embodiments of the invention for application with analytical devices such as flow cytometers, cell sorters, microarray analyzers, imaging microscopes, or microimaging equipment, which may easily be built to contain two or more, and perhaps thousands or even millions parallel channels for analysis, and in such that each of these separate channels is capable to perform the identical or very similar function to a single flow cytometry sorting nozzle, they may be considered "machines", and it is understood that even a very small device which could be held in a persons hand, may contain many hundreds or many thousands of such "machines" and only be able to function if the use of illumination light is similar or identical to the inventions described herein.

Example 1

Purified fixed bull sperm heads (also described as bull sperm nuclei), stained in standard conditions with DNA binding stain Hoechst 33342, are used as a performance standard to calibrate a sperm sorting flow cytometer prior to the sorting of live sperm. A pulsed laser (Spectrophysics VNGD350-HMD355) delivering 300 mW of energy at 355 nm and 80 MHz illuminates the sample analysis stream in a flow cytometer operating at standard settings and provides the histogram plot shown in Fig. Ex 1. This demonstrates that a standard sperm sorting flow cytometer equipped with the pulsed laser is able to resolve bull sperm nuclei into X-chromosome bearing and Y-chromosome bearing populations using standard conditions.

Example 2

A sample of live bull sperm is stained in standard conditions with DNA binding stain Hoechst 33342. A pulsed laser (Spectrophysics VNGD350-HMD355) delivering 300 mW of energy at 355 nm and 80 MHz illuminates the sample analysis stream in a flow cytometer operating at standard settings sorting said sperm and provides the histogram plot shown in Fig Ex 2. This demonstrates that a standard sperm sorting flow cytometer equipped with the pulsed laser is able to resolve live sperm into X-chromosome bearing and Y-chromosome bearing populations under standard conditions.

The above sample is sorted for collection of X-chromosome bearing sperm, and the sort collection rate is 3800 live X-chromosome bearing sperm second. A resort analysis of the sample prepared in said manner measures the purity of said sorted sample to be 95%. This demonstrates that a standard sperm sorting flow cytometer equipped with the pulsed laser is able to enrich the content of a sperm population from one in which approximately 50% of the sperm are X-chromosome bearing sperm, to one in which 95% of the sperm are X-chromosome bearing sperm.

Said sorted sperm above are further processed by standard methods for packaging into artificial insemination straws, are cryopreserved by the standard freezing method, and are thawed for analysis of motility of the sperm. Percent motility at various points in the procedure is determined to be: After stain 80%, after sorting 70%, after cooling 65%, after freezing and thawing at 0 minutes 45%, 30 minutes after thawing 45%, 120 minutes after thawing 35%. This demonstrates that a standard sperm sorting flow cytometer equipped with the pulsed laser is able to enrich live stained sperm samples which appear normal in respect to the sperm motility.

Example 3

A sample of live bull sperm is stained in standard conditions with DNA binding stain Hoechst 33342. A pulsed laser (Spectrophysics VNGD350-HMD355) delivering 300 mW of energy at 355 nm and 80 MHz is equipped with beam splitters and neutral density filters, in five separate conditions, to provide illumination energy beam levels of 160 mW (53% of beam power), 130 mW (43% of beam power), 90 mW (30% of beam power), 60 mW (20% of beam power), and 20 mW (6.6% of beam power), respectively, to illuminate the sample analysis stream of a sperm sorting flow cytometer operating at standard settings sorting said stained sperm and providing the 5 histogram plots shown in Fig Ex 3. This demonstrates that a standard sperm sorting flow cytometer equipped with the pulsed laser is able to clearly resolve live sperm with energies as low as 60 mW (20% of the beam).

The above samples are sorted at each of the 5 beam energy settings for collection of X-chromosome bearing sperm and Y-chromosome bearing sperm in separate fractions, and the sort collection rate is 850-3500 X-chromosome bearing or Y-chromosome bearing sperm second, depending on the power used, with lower powers associated with lower sort collection rates. A resort analysis of the samples prepared in said manner measures the purity of said sorted samples as shown in Table Ex 3. This demonstrates that a standard sperm sorting flow cytometer equipped with the pulsed laser delivering beam energies in the range of 20 mW to 160 mW is consistently able to enrich the content of a sperm population from one in which approximately 50% of the sperm are X-chromosome bearing sperm, to one in which 95% or higher of the sperm are X-chromosome bearing sperm, and simultaneously to one in which 90% or higher of the sperm are Y-chromosome bearing sperm.

TABLE 4

| Beam Energy (Pulsed) | % Purity - X | % Purity - Y |
|---|---|---|
| 20 mW | 96.5 | 91.0 |
| 60 mW | 93.5 | 85.5 |
| 90 mW | 96.0 | 89.5 |
| 130 mW | 96.0 | 91.0 |
| 160 mW | 97.0 | 93.0 |

Example 4

A sample of live bull sperm is stained in standard conditions with DNA binding stain Hoechst 33342. A pulsed laser (Spectrophysics VNGD350-HMD355) delivering 300 mW of energy at 355 nm and 80 MHz is equipped with beam splitters and neutral density filters, in two separate conditions, to provide illumination energy beam levels of 130 mW (43% of beam power) and 70 mW (23% of beam power), respectively, to the sample analysis stream of a flow cytometer operating at standard settings sorting said stained sperm. As comparison, the same sample is analyzed on two identical but different flow cytometers operating at standard settings and equipped with a CW (continuous wave) lasers delivering 150 mW in both cases. This demonstrates that even with lower beam energies a standard sperm sorting flow cytometer equipped with the pulsed laser provides superior resolution capability when compared to a same standard sperm sorting flow cytometer equipped with a standard CW laser.

Example 5

A sample of live bull sperm is stained in standard conditions with DNA binding stain Hoechst 33342 with the standard concentration of Hoechst 33342 being defined as 100% level of stain (control). Two additional samples are prepared which are identical except that they are stained with 80% or 60% of the amount of Hoechst 33342 stain, respectively. A pulsed laser (Spectrophysics VNGD350-HMD355) delivering 300 mW of energy at 355 nm and 80 MHz is equipped with beam splitters and neutral density filters, in two separate conditions, to provide illumination energy beam levels of 150 mW (50% of beam power) and 90 mW (30% of beam power), respectively, to the sample analysis stream of a flow cytometer operating at standard settings sorting said stained sperm with 3 different concentrations of stain used. The resolution between X-chromosome bearing and Y-chromosome bearing sperm for these 6 conditions are provided in the 6 histogram plots shown in Fig Ex 5. This demonstrates that lesser amounts of Hoechst 33342 stain may be used to prepare sperm samples for sorting on a standard sperm sorting flow cytometer, if higher pulsed beam energies are also used.

Example 6

Purified fixed bull sperm heads (also described as bull sperm nuclei), stained in standard conditions with DNA binding stain Hoechst 33342, are used as a performance standard to calibrate a sperm sorting flow cytometer prior to the sorting of live sperm. A pulsed laser (Spectrophysics VNGD350-HMD355) delivering 300 mW of energy at 355 nm and 80 MHz and equipped with a beam splitter to provide an illumination energy beam level of 150 mW (50% of beam power) illuminates the sample analysis stream of a flow cytometer operating at standard settings. Said stained nuclei are analyzed at 20,000 events/second (a rate comparable to the rate used in live bull sperm analysis), as well as at 59,000 events/second. The resolution between X-chromosome bearing and Y-chromosome bearing bull sperm nuclei for these 2 event rate conditions are provided in the 2 histogram plots shown in Fig Ex 6. This demonstrates, that for ideal particles such as nuclei standards, the event rates of analysis may be increased as much as 3-fold with only modest loss in the resolution between X-chromosome bearing and Y-chromosome bearing bull sperm nuclei.

Example 7

Samples of live bull sperm from 4 different bulls were stained in standard conditions with DNA binding stain Hoechst 33342. A pulsed laser (Spectrophysics VNGD350-HMD355) delivering 300 mW of energy at 355 nm and 80 MHz is equipped with beam splitters and neutral density filters, in two separate conditions, to provide illumination energy beam levels of 300 mW (100% of beam power) and 150 mW (50% of beam power), respectively, to the sample analysis stream of a flow cytometer operating at standard settings sorting said stained sperm samples. As comparison, the same samples are sorted on an identical but different flow cytometer operating at standard settings and equipped with a CW (continuous wave) laser delivering 150 mW of energy in the illumination beam. The samples are bulk sorted, which means both X-chromosome bearing and Y-chromosome bearing sperm fractions are pooled. The sorted sperm samples are cryopreserved using standard procedures and the percent of post thaw sperm motilities, as well as the percent of live and dead using PI staining with flow cytometry analysis are scored. The averages for all 4 bulls with the 3 different illumination conditions are shown in Table 5. This demonstrates without statistical significance that all three conditions of illumination yield similar numbers of intact viable sperm after sorting.

TABLE 5

| Laser (mW) | % Motility at 0 min post thaw | % Motility at 90 min post thaw | % Live at 0 min post thaw | % Live at 90 min post thaw |
| --- | --- | --- | --- | --- |
| CW (150 mW) | 50.0 | 42.5 | 43.5 | 40.6 |
| Pulsed (150 mW) | 46.3 | 42.5 | 40.0 | 37.9 |
| Pulsed (300 mW) | 48.1 | 36.3 | 40.3 | 37.2 |

Example 8

Samples of live bull sperm from 5 different bulls are stained in standard conditions with DNA binding stain Hoechst 33342, with the standard concentration of Hoechst 33342 being defined as 100% level of stain (control). Two additional samples from the same 5 bulls are prepared which are identical except that they are stained with 80% or 60% of the amount of Hoechst 33342 stain, respectively.

A pulsed laser (Spectrophysics VNGD350-HMD355) delivering 300 mW of energy at 355 nm and 80 MHz is equipped with beam splitters and neutral density filters, in two separate conditions, to provide illumination energy beam levels of 150 mW (50% of beam power) and 90 mW (30% of beam power), respectively, to the sample analysis stream of a flow cytometer operating at standard settings sorting said stained sperm samples. As comparison, the same samples are sorted on an identical but different flow cytometer operating at standard settings and equipped with a CW (continuous wave) laser delivering 150 mW of energy in the illumination beam.

For the sorting procedures on all these samples, the average values for resolution (higher values are better), the coincidence rates (lower values are better), the sort collection rates (higher values are better) are compared and shown in Table 6. This demonstrates that sorting efficiencies in all conditions tested with the pulsed laser were equal to or better than the sorting efficiencies achieved using the standard CW laser.

TABLE 6

| Stain(%)/Laser (mW) | Resolution | Co-incidence rate | Sort Rate |
| --- | --- | --- | --- |
| 100/150 pulsed | 8.0 | 3570 | 3160 |
| 100/90 pulsed | 9.3 | 3560 | 2610 |
| 80/150 pulsed | 8.2 | 3600 | 3160 |
| 80/90 pulsed | 9.6 | 3500 | 2480 |
| 60/150 pulsed | 8.6 | 3600 | 2940 |
| 60/90 pulsed | 9.8 | 3520 | 2450 |
| 100/150 CW | 7.6 | 4380 | 2720 |

The same samples are bulk sorted, which means both X-chromosome bearing and Y-chromosome bearing sperm fractions are pooled. The sorted sperm samples are cryopreserved using standard procedures and the percent of post thaw motilities, as well as the percent of live/dead using PI staining with flow cytometry analysis are scored. The averages for all 5 bulls with the 7 different stain and illumination conditions are shown in Table 7. This demonstrates that sperm viability and live counts in all conditions tested with the pulsed laser were equal to or better than the sperm viability and live counts achieved using the standard CW laser and standard stain.

TABLE 7

| Stain(%)/Laser (mW) | % Motility at 0 min post thaw | % Motility at 120 min post thaw | % Live at 30 min post thaw | % Live at 120 min post thaw |
| --- | --- | --- | --- | --- |
| 100/150 pulsed | 43.3 | 34.0 | 36.8 | 32.4 |
| 100/90 pulsed | 42.8 | 33.5 | 35.3 | 33.2 |
| 80/150 pulsed | 42.8 | 33.8 | 35.1 | 35.1 |
| 80/90 pulsed | 42.0 | 35.3 | 35.2 | 29.7 |
| 60/150 pulsed | 40.8 | 31.0 | 35.8 | 35.1 |
| 60/90 pulsed | 41.0 | 32.8 | 34.4 | 33.7 |
| 100/150 CW | 39.8 | 33.3 | 33.4 | 28.6 |

Example 9

Samples of live bull sperm from 5 different bulls and 2-6 replicates were stained in standard conditions with DNA binding stain Hoechst 33342 (80%) and bulk sorted under standard conditions in a sperm sorting flow cytometer at event rates of 23,000 sperm/second. A pulsed laser (Spectrophysics VNGD350-HMD355) delivering 300 mW of energy at 355 nm and 80 MHz is equipped with beam splitter to provide illumination energy beam level of 150 mW (50% of beam power) to the sample analysis stream of a flow cytometer operating at standard settings sorting said stained sperm samples.

As a control comparison, same samples of live bull sperm from 5 different bulls and 2-6 replicates were stained in standard conditions with DNA binding stain Hoechst 33342 (100%) and these samples were sorted on an identical but different flow cytometer operating at standard settings and equipped with a CW (continuous wave) laser delivering 150 mW of energy in the illumination beam.

Said various sperm samples were used at concentrations of 200,000 sperm/ml or 1 million sperm/ml to inseminate matured bovine oocytes in standard procedures of in-vitro fertilization (IVF). Cleavage and 2 cell rates at 2.75 days post-insemination, blastocyst development rates at 7.75 days post-insemination, total cell numbers in blastocyst and the blastocyst quality at 7.75 days were measured. The average results for 587 oocytes inseminated with sorted sperm prepared from the system equipped with the pulsed laser, and for 558 oocytes inseminated with sorted sperm prepared from the system equipped with the CW laser are shown in Table 8. Note: lower numbers for blastocyst quality are better. This demonstrates that sperm prepared by a standard sperm sorting flow cytometer equipped with the pulsed laser is capable of fertilizing oocytes in standard IVF procedures and exhibits similar cleavage and blastocyst rates, with the mean quality of blastocysts being slightly better when inseminated with sperm sorted using the standard flow cytometer equipped with the pulsed laser.

TABLE 8

| Laser (mW) | % Cleaved | % 2 cell | % blastocyst | quality of blastocyst | cell counts in blastocyst |
| --- | --- | --- | --- | --- | --- |
| CW (150 mW) | 50.7 | 27.3 | 6.7 | 2.7 | 131.8 |
| Pulsed (150 mW) | 49.7 | 29.5 | 5.2 | 2.1 | 136.2 |

Example 10

Samples of live bull sperm from 3 different bulls, on multiple days, were stained in standard conditions with DNA binding stain Hoechst 33342 (100%) and bulk sorted under standard conditions in a sperm sorting flow cytometer at event rates of 20-23,000 sperm/second. A pulsed laser (Spectrophysics VNGD350-HMD355) delivering 300 mW of energy at 355 nm and 80 MHz is equipped with a beam splitter to provide illumination energy beam level of 150 mW (50% of beam power) to the sample analysis stream of a flow cytometer operating at standard settings sorting said stained sperm samples.

As a control comparison, same samples of live bull sperm from the same 3 different bulls on same days, were stained in standard conditions with DNA binding stain Hoechst 33342 (100%) and these samples were sorted on an identical but different flow cytometer operating at standard settings and equipped with a CW (continuous wave) laser delivering 150 mW of energy in the illumination beam.

Said various sperm samples were used in amounts of 2 million sperm per cyropreserved artificial insemination straw containing 0.25 ml of fluid.

Control straws containing 10 million unsorted sperm, and control straws containing 2 million X enriched sperm sorted using a sperm sorting flow cytometer equipped with a the standard CW laser were used.

In a heterospermic analysis, X-fractions from CW laser sorts were mixed in equal sperm numbers with Y-fractions from pulsed laser sorts to create the #1 comparison. Y-fractions from CW laser sorts were mixed in equal sperm numbers with X-fractions from pulsed laser sorts to create the #2 comparison. Identification of sex in fetuses at 60 days was used as a marker to assign the sex outcome, and accordingly, the likely condition (which laser) can be attributed to successful fertilization. The heterospermic method is particularly useful, as all other factors than sorting procedure are internally controlled in each insemination.

Holstein heifers weighing approximately 750 pounds were synchronized using CIDR/Lutalase. Thereafter observed (AM or PM) for standing heat and were inseminated at 12-24 hours after heat observation. Using 2 inseminators, and a single deep uterine insemination treatment, with 5 test groups spaced approximately one month apart, at a single farm, pregnancy rates and sex of fetus were determined at 60 days post insemination using ultrasonograhy. The results shown in Table 9 demonstrate that the sperm sorted with a standard sperm sorting flow cytometer equipped with a pulsed laser give essentially identical pregnancy rates as sperm sorted using a standard sperm sorting flow cytometer equipped with the standard CW laser.

TABLE 9

| Sperm dose type | % Conception Rate | Preganancies/ Inseminations |
|---|---|---|
| Unsexed control containing 10 million total sperm | 62.5 | 55/88 |
| X-sexed control containing 2 million total sperm | 56.4 | 101/179 |
| Heterospermic #1 containing 2 million total sperm | 50.0 | 45/90 |
| Heterospermic #2 containing 2 million total sperm | 58.4 | 52/89 |
| Pregancies attributed to CW laser | 49.50% | 48/97 |
| Pregancies attributed to pulsed laser | 50.50% | 49/97 |

Example 11

A sample of live dolphin sperm was collected at poolside, shipped via air freight, and stained with Hoechst 33342 approximately 6 hours after collection. The sorting efficiencies for the single stained sample were then tested on two identical Mo Flo SX sperm sorters, in one case equipped with a pulsed laser (Spectrophysics VNGD350-HMD355) delivering 300 mW of energy at 355 nm and 80 MHz equipped with a beam splitter to provide illumination energy beam level of 150 mW (50% of beam power), and the second case with an Innova 90-6 (CW—continuous wave) laser delivering 150 mW of beam energy. The dolphin ejaculate was stained 3 times, and in each case sorted for approximately 2 hours.

Using the CW laser, with sorter event rates at 30,000/sec an average co-incidence rate of 6430/sec was observed, X-chromosome bearing sperm were collected at an average rate of 3450/sec and a total of 72 million sperm were collected in 7 hours for an average recovery of 10.3 million sperm per hour.

Using the pulsed laser, with sorter event rates at 30,000/sec an average co-incidence rate of 5400/sec was observed, X-chromosome bearing sperm were collected at an average rate of 3930/sec and a total of 79.5 million sperm were collected in 6.33 hours for an average recovery of 12.6 million sperm per hour.

The recovered sperm from both samples has X purities of >95% and post-thaw motility of >50%.

Example 12

A sample of live canine sperm was collected from a common dog housed at a kennel and stained about 3 hours later with a non-optimized quantity of Hoechst 33342. The stained sperm were analyzed by a standard sperm sorter equipped with a pulsed laser (Spectrophysics VNGD350-HMD355) delivering 300 mW of energy at 355 nm and 80 MHz equipped with a beam splitter to provide illumination energy beam level of 150 mW (50% of beam power). Approximately 43% of the sperm were correctly oriented. From the correctly oriented stained canine sperm, approximately 32% were collected as X-chromosome bearing sperm, and approximately 36% were collected as Y-chromosome bearing sperm. Visual inspection by microscope showed high numbers of canine sperm in both samples to be motile.

Example 13

The standard CW laser uses a cathode tube which requires an average input of 12 KW of electrical power, and a large volume of cooling water, or a chiller with a load of approximately 15 KW. The pulsed laser (Spectrophysics VNGD350-HMD355 delivering 300 mW of energy at 355 nm and 80 MHz) requires approximately 500 watts (0.5 KW).

The standard CW laser also requires replacement of the cathode tube after approximately 5000 hours of use, at a replacement cost of about $12,000, whereas the VNG pulsed laser is expected to have 30,000+ hours of operation before refurbishment of head element at similar costs.

A commercial operation using the sperm sorting flow cytometers to sort sperm for production of artificial insemination straws, running 24 hours per day, year-round, may be expected to operate lasers for 8,640 hours per year.

Electric utility and water rates in Fort Collins quoted for the year 2004 were used to calculate the operating costs of the standard CW laser, in the first case cooled by utility water and in the second case cooled using electric powered chiller. The pulsed laser requires no cooling. The comparative costs are shown in Table 10. This demonstrates that the pulsed laser has significant benefits in reducing the costs of operation of a sperm sorting flow cytometer.

TABLE 10

| Cost component | CW laser with water cooling | CW laser with electric chiller cooling | Pulsed Laser |
|---|---|---|---|
| Electrical Charges | $ 4,389 | $ 9,828 | $ 183 |
| Water Charges | $ 6,483 | $ 0 | $ 0 |
| Laser tube or rebuild | $20,736 | $20,736 | $3,456 |
| TOTAL (1 year) | $31,608 | $30,564 | $3,639 |

The following previously presented claims are part of the disclosure:

1. A method of flow cytometry sperm processing comprising the steps of:
   establishing a sheath fluid;
   flowing said sheath fluid into a nozzle;
   injecting irradiatable sperm cells into said sheath fluid;
   multiply subjecting said irradiatable sperm cells to radiation for a first amount of time;
   multiply terminating said radiation of said irradiatable sperm cells for a second amount of time;
   multiply exciting said irradiatable sperm cells with said radiation;
   emitting fluorescence from said excited sperm cells;
   detecting an amount of said emitted fluorescence from each of said sperm cells;
   evaluating said amount of emitted fluorescence from each of said sperm cells;
   selecting an electrical condition to be associated with each of said sperm cells in said sheath fluid flow;
   charging a stream of said irradiatable sperms cell and sheath fluid based upon deduced properties of each of said excited sperm cells in said sheath fluid flow;
   forming a charged drop;
   isolating said charged drop from said sheath fluid flow;
   deflecting said charged drops;
   sorting said sperm cells; and
   collecting said sorted sperm cells.

2. A method of flow cytometry sperm processing according to claim 1 wherein said step of detecting an amount of said emitted fluorescence from each of said sperm cells comprises the step of quantitatively detecting an amount of said emitted fluorescence from each of said sperm cells.

3. A method of flow cytometry sperm processing according to claim 2 wherein said step of quantitatively detecting an amount of said emitted fluorescence from each of said sperm cells comprises the step of distinguishing between a X-chromosome bearing sperm and a Y-chromosome bearing sperm wherein said X-chromosome bearing sperm emits a different fluorescence from said Y-chromosome.

4. A method of flow cytometry sperm processing according to claim 1 wherein said step of sorting said sperm cells comprises the step of rapidly sorting said sperm cells.

5. A method of flow cytometry sperm processing according to claim 4 wherein said step of rapidly sorting said sperm cells comprises the step of sorting at a rate greater than 500 cells per second.

6. A method of flow cytometry sperm processing according to claim 4 wherein said step of rapidly sorting said sperm cells comprises the step of sorting at a rate selected from a group consisting of:
   greater than 1000 cells per second;
   greater than 1500 cells per second;
   greater than 2000 cells per second; and
   greater than 3000 cells per second.

7. A method of flow cytometry sperm processing according to claim 1 and further comprising the step of utilizing a beam manipulator.

8. A method of flow cytometry sperm processing according to claim 7 wherein said step of utilizing a beam manipulator comprises the step of utilizing a beam manipulator selected from a group consisting of mirrors, deflectors, beam splitters, prisms, refractive objects, lenses and filters.

9. A method of flow cytometry sperm processing according to claim 1 wherein said step of detecting an amount of said emitted fluorescence from each of said sperm cells comprises the step of detecting an amount of said emitted fluorescence from each of said sperm cells with a detection system.

10. method of flow cytometry sperm processing according to claim 9 wherein said step of detecting an amount of said emitted fluorescence from each of said sperm cells with a detection system comprise the step of utilizing a photomultiplier tube.

11. A method of flow cytometry sperm processing according to claim 1 wherein said step of injecting irradiatable sperm cells into said sheath fluid comprises the step of staining said sperm with a fluorescent dye.

12. A method of flow cytometry sperm processing according to claim 11 wherein said step of staining said sperm with a fluorescent dye comprises the step of staining said sperm with fluorochrome.

13. A method of flow cytometry sperm processing according to claim 12 wherein said step of staining said sperm with fluorochrome comprises the step of staining said sperm with Hoechst bisbenzimide H33342 fluorochrome.

14. A method of flow cytometry sperm processing according to claim 11 or 12 wherein said step of staining said sperm with a fluorescent dye comprises the step of staining said sperm with a large amount of dye.

15. A method of flow cytometry sperm processing according to claim 14 wherein said step of staining said sperm with a large amount of dye comprises the step of attaching several stain molecules to binding sites on a deoxyribonucleic acid.

16. A method of flow cytometry sperm processing according to claim 11 or 13 wherein said step of multiply subjecting said irradiatable sperm cells to radiation for a first amount of time comprises the step of multiply subjecting said irradiatable sperm cells to radiation having a wavelength appropriate to activate fluorescence in said irradiatable sperm.

17. A method of flow cytometry sperm processing according to claim 16 wherein said step of multiply subjecting said irradiatable sperm cells to radiation having a wavelength appropriate to activate fluorescence in said irradiatable sperm comprises the step of providing a wavelength of said radiation of 355 nm.

18. A method of flow cytometry sperm processing according to claim 11 or 13 wherein said step of staining said sperm with a fluorescent dye comprises the step of staining said sperm for a reduced staining time.

19. A method of flow cytometry sperm processing according to claim 18 wherein said step of staining said sperm for a reduced staining time comprises the step of staining said sperm for less than about 40 minutes.

20. A method of flow cytometry sperm processing according to claim 18 wherein said reduced staining time is selected from a group consisting of:
less than about 35 minutes;
less than about 30 minutes;
less than about 25 minutes;
less than about 20 minutes;
less than about 15 minutes;
less than about 10 minutes; and
less than about 5 minutes.

21. A method of flow cytometry sperm processing according to claim 1 or 11 wherein said step of multiply exciting said irradiatable sperm cells with said radiation comprises the step of sufficiently hitting said sperm with said radiation to cause said irradiatable sperm to emit fluorescence.

22. A method of flow cytometry sperm processing according to claim 1 wherein said step of multiply subjecting said irradiatable sperm cells to radiation for a first amount of time comprises the step of multiply subjecting said irradiatable sperm cells to low power radiation.

23. A method of flow cytometry sperm processing according to claim 22 wherein said step of multiply subjecting said irradiatable sperm cells to low power radiation comprises the step of providing a low power radiation of less than 300 mW.

24. A method of flow cytometry sperm processing according to claim 22 wherein said step of multiply subjecting said irradiatable sperm cells to low power radiation comprises the step of selecting a low power from the group consisting of:
less than 350 milliwatt;
less than 200 milliwatt;
less than 175 milliwatt;
less than 100 milliwatt;
less than 88 milliwatt;
less than 50 milliwatt; and
less than 25 milliwatt.

25. A method of flow cytometry sperm processing according to claim 1 and further comprising the step of splitting said radiation into at least two light beams.

26. A method of flow cytometry sperm processing according to claim 25 wherein said step of splitting said radiation into at least two light beams comprises the step of subjecting said sperm cells with a reduced power of radiation than which was originally emitted from a laser source.

27. A method of flow cytometry sperm processing according to claim 26 wherein said step of subjecting said sperm cells with a reduced power of radiation than which was originally emitted from a laser source comprises the step selecting said reduced power from a group consisting of a half, a fourth and an eighth said originally emitted power.

28. A method of flow cytometry sperm processing according to claim 1 wherein said step of detecting an amount of said emitted fluorescence from each of said sperm cells comprises the step of distinguishing between a X chromosome bearing sperm and a Y chromosome bearing sperm wherein said X chromosome bearing sperm emits a different fluorescence from said Y chromosome.

29. A method of flow cytometry sperm processing according to claim 1 or 28 wherein said step of collecting said sorted sperm cells comprises the step of collecting a sorted population of X chromosome bearing sperm and collecting a sorted population of Y chromosome bearing sperm.

30. A method of flow cytometry sperm processing according to claim 29 wherein said step of collecting a sorted population of X chromosome bearing sperm and collecting a sorted population of Y chromosome bearing sperm comprises the step of collecting said populations at a high purity.

31. A method of flow cytometry sperm processing according to claim 30 wherein said step of collecting said populations at a high purity comprises the step of selecting said high purity from a group consisting of:
greater than 85% purity;
greater than 90% purity;
greater than 95% purity;
greater than 96% purity; and
greater than 98% purity.

32. A method of flow cytometry sperm processing according to claim 30 wherein said step of collecting said populations at a high purity comprises the step of a providing a high resolution of said sorted sperm.

33. A method of flow cytometry sperm processing according to claim 32 wherein high resolution of said sorted sperm is selected from a group consisting of:
greater than 7.0;
greater than 7.5;
greater than 8.0;
greater than 8.5;
greater than 9.0; and
greater than 9.2.

34. A method of flow cytometry sperm processing according to claim 1 wherein said step of sorting said sperm cells comprises the step of sorting said sperm cells at a low coincidence rate.

35. A method of flow cytometry sperm processing according to claim 34 wherein said low coincidence rate is selected from the group consisting of:
less than 4400;
less than 4000;
less than 3700; and
less than 3600.

36. A method of flow cytometry sperm processing according to claim 29 wherein said step of collecting a sorted population of X chromosome bearing sperm and collecting a sorted population of Y chromosome bearing sperm comprises the step of collecting said populations at a high collection rate.

37. A method of flow cytometry sperm processing according to claim 36 wherein said high collection rate is selected from a group consisting of:
greater than 2400 sperm per second;
greater than 2600 sperm per second;
greater than 2900 sperm per second;
greater than 3000 sperm per second; and
greater than 3100 sperm per second.

38. A method of flow cytometry sperm processing according to claim 1 wherein said step of detecting an amount of said emitted fluorescence from each of said sperm cells comprises the step of detecting said sperm cells at an event rate of between about 10,000 to about 60,000 sperm cells per second.

39. A method of flow cytometry sperm processing according to claim 1 wherein said step of multiply subjecting said irradiatable sperm cells to radiation comprises the step of initiating a sensing routine.

40. A method of flow cytometry sperm processing according to claim 1 wherein said step of multiply subjecting said irradiatable sperm cells to radiation for a first amount of time comprises the step multiply subjecting said irradiatable sperm cells to radiation for a first amount of time between about 5 to about 20 picoseconds.

41. A method of flow cytometry sperm processing according to claim 1 or 40 multiply terminating said radiation of said irradiatable sperm cells for a second amount of time comprises the step of multiply terminating said radiation of said irradiatable sperm cells for a second amount of time between about 0.5 to about 20 nanoseconds.

42. A method of flow cytometry sperm processing according to claim 41 and further comprising providing a repetition rate between about 2 to about 10 microseconds.

43. A method of flow cytometry sperm processing according to claim 42 wherein said step of providing a repetition rate comprises the step of providing a repetition rate between 50-200 MHz.

44. A method of flow cytometry sperm processing according to claim 42 wherein said step of providing a repetition rate comprises the step of providing a repetition rate of up to about 80 MHz.

45. A method of flow cytometry sperm processing according to claim 11 wherein said step of staining said sperm with a fluorescent dye comprises the step of minimally staining said sperm with a fluorescent dye.

46. A method of flow cytometry sperm processing according to claim 45 wherein said step of minimally staining said sperm with a fluorescent dye comprises the step of allowing less stain to bind to said sperm.

47. A method of flow cytometry sperm processing according to claim 45 or 46 wherein said step of minimally staining said sperm with a fluorescent dye comprises the step of providing a percentage of stain selected from a group consisting of about 90%, about 80%, about 70% and about 60% of a maximum stain.

48. A method of flow cytometry sperm processing according to claim 1 wherein said step of forming a charged drop comprises the step of oscillating said sheath fluid to form said charged drop.

49. A method of flow cytometry sperm processing according to claim 1 wherein said step of injecting irradiatable sperm cells into said sheath fluid comprises injected sperm cells selected from a group consisting of mammals, bovine sperm cells, equine sperm cells, porcine sperm cells, ovine sperm cells, camelid sperm cells, ruminant sperm cells, and canine sperm cells.

50. A method of flow cytometry sperm processing according to claim 1 wherein said step of flowing said sheath fluid into a nozzle comprises the step of flowing at least one sheath fluid and said sperm cells into at least two nozzles.

51. A method of flow cytometry sperm processing according to claim 50 and further comprising the step of collecting X chromosome bearing sperm populations and Y chromosome bearing sperm populations in a collector, wherein said collector is selected from the group consisting of multiple containers and a combined collector having a individual containers.

52. A method of flow cytometry sperm processing according to claim 51 and further comprising the step of providing a number of selected containers less than a number of nozzles.

53. A method of flow cytometry sperm processing according to claim 1 or 50 and further comprising the step of utilizing at least one shared resource to process said sperm cells.

54. A method of flow cytometry sperm processing according to claim 53 wherein said step of utilizing at least one shared resource to process said sperm cells comprises the steps of:
utilizing one radiation source;
splitting said radiation into at least two beams; and
directing each of said beams to said nozzle and said sperm cells.

55. A method of flow cytometry sperm processing according to claim 54 and further comprising the step of subjecting said radiation to at least two nozzles of identical flow cytometers.

56. A method of flow cytometry sperm processing according to claim 1 and further comprising the step of utilizing said collected sorted sperm for insemination of female mammals.

57. A method of flow cytometry sperm processing according to claim 1 wherein said steps of multiply subjecting said irradiatable sperm cells to radiation for a first amount of time and multiply terminating said radiation of said irradiatable sperm cells for a second amount of time comprises the step of utilizing a pulsed laser.

58. A method of flow cytometry sperm processing according to claim 57 wherein said step of utilizing a pulsed laser comprises the step of a utilizing said pulsed laser selected from a group consisting of Nd:YAG and Nd:YVO$_4$.

59. A mammal produced through use of a sorted sperm cells produced with a flow cytometer system according to claim 1, 2, 13, 23, 40, or 49.

60. A method of flow cytometry sample processing comprising the steps of:
establishing at least one sheath fluid;
flowing said at least one sheath fluid into at least two nozzles;
injecting at least one irradiatable sample into said at least one sheath fluid;
utilizing at least one shared resource to process said at least one irradiatable sample;
subjecting said irradiatable sample to radiation;
exciting said irradiatable sample with said radiation;
emitting fluorescence from said excited sample;
detecting an amount of said emitted fluorescence from each particle in said sample;
evaluating said amount of emitted fluorescence from each particle in said sample;
selecting an electrical condition to be associated with each particle of said sample in said sheath fluid flow;
charging a stream of said irradiatable sample and sheath fluid based upon deduced properties of each particle of said sample in said sheath fluid flow;
forming a charged drop;
isolating said charged drop from said sheath fluid flow;
deflecting said charged drops;
sorting said sample; and
collecting said sorted sample.

61. A method of flow cytometry sample processing according to claim 60 wherein said step of injecting at least one irradiatable sample into said at least one sheath fluid comprises the step of injecting usable cells into said at least one sheath fluid.

62. A method of flow cytometry sample processing according to claim 61 wherein said step of injecting usable cells into said at least one sheath fluid comprises the step of injecting reproductive cells into said at least one sheath fluid.

63. A method of flow cytometry sample processing according to claim 62 wherein said step of injecting reproductive cells into said at least one sheath fluid comprises the step of injecting haploid cells into said at least one sheath fluid.

64. A method of flow cytometry sample processing according to claim 63 wherein said step of injecting haploid cells into said at least one sheath fluid comprises the step of injecting sperm cells into said at least one sheath fluid.

65. A method of flow cytometry sample processing according to claim 60 wherein said step of injecting at least one irradiatable sample into said at least one sheath fluid comprises the step of injecting a delicate sample into said at least one sheath fluid.

66. A method of flow cytometry sample processing according to claim 60 wherein said step of injecting at least one irradiatable sample into said at least one sheath fluid comprises the step of injecting a sample selected from a group consisting of non-biological particles, biological particles, and sperm.

67. A method of flow cytometry sample processing according to claim 60 wherein said step of subjecting said irradiatable sample to radiation comprises the step of subjecting said irradiatable sample to a continuous wave laser.

68. A method of flow cytometry sample processing according to claim 60 wherein said step subjecting said irradiatable sample to radiation comprises the steps of:
    multiply subjecting said irradiatable sample to radiation for a first amount of time;
    multiply terminating said radiation of said irradiatable sample for a second amount of time; and
    multiply exciting said irradiatable sample with said radiation.

69. A method of flow cytometry sample processing according to claim 60 wherein said step of utilizing said at least one shared resource to process said at least one irradiatable sample comprises the step of utilizing one radiation source for subjecting said irradiatable sample in said at least two nozzles.

70. A method of flow cytometry sample processing according to claim 69 wherein said step of utilizing one radiation source for subjecting said irradiatable sample in said at least two nozzles comprises the step of splitting a radiation beam into at least two beams and directing one beam toward each of said at least two nozzles.

71. A method of flow cytometry sample processing according to claim 60 and further comprising the step of splitting said radiation into at least two light beams.

72. A method of flow cytometry sample processing according to claim 71 wherein said step of splitting said radiation into at least two light beams comprises the step of subjecting said with a reduced power of radiation than which was originally emitted from a laser source.

73. A method of flow cytometry sample processing according to claim 72 wherein said step of subjecting said with a reduced power of radiation than which was originally emitted from a laser source comprises the step of selecting said reduced power from a group consisting of a half, a fourth, and an eighth of said originally emitted power.

74. A method of flow cytometry sample processing according to claim 60 wherein said step of detecting an amount of said emitted fluorescence from each particle in said sample comprises the step of quantitatively detecting an amount of said emitted fluorescence from each particle in said sample.

75. A method of flow cytometry sample processing according to claim 74 wherein said step of quantitatively detecting an amount of said emitted fluorescence from each particle in said sample comprises the step of distinguishing between a first population of particles and a second population of particles wherein said first population of particles emits a different fluorescence from said second population of particles.

76. A method of flow cytometry sample processing according to claim 74 wherein said step of injecting at least one irradiatable sample into said at least one sheath fluid comprises the step of injecting at least one irradiatable sperm cells into said at least one sheath fluid and wherein said step of quantitatively detecting an amount of said emitted fluorescence from each particle in said sample comprises distinguishing between a X chromosome bearing sperm and a Y chromosome bearing sperm wherein said X chromosome bearing sperm emits a different fluorescence from said Y chromosome.

77. A method of flow cytometry sample processing according to claim 60 wherein said step of sorting said sample comprises the step of rapidly sorting said sample.

78. A method of flow cytometry sample processing according to claim 77 wherein said step of rapidly sorting said sample cells comprises the step of sorting at a rate greater than 500 cells per second.

79. A method of flow cytometry sample processing according to claim 77 wherein said step of rapidly sorting said sample cells comprises the step of sorting at a rate selected from a group consisting of
    greater than 1000 cells per second;
    greater than 1500 cells per second;
    greater than 2000 cells per second; and
    greater than 3000 cells per second.

80. A method of flow cytometry sample processing according to claim 60 and further comprising the step of utilizing a beam manipulator.

81. A method of flow cytometry sample processing according to claim 80 wherein said step of utilizing a beam manipulator comprises the step of utilizing a beam manipulator selected from a group consisting of mirrors, deflectors, beam splitters, prisms, refractive objects, lenses and filters.

82. A method of flow cytometry sample processing according to claim 60 wherein said step of detecting an amount of said emitted fluorescence from said sample comprises the step of detecting an amount of said emitted fluorescence from said sample with a detection system.

83. A method of flow cytometry sample processing according to claim 82 wherein said step of detecting an amount of said emitted fluorescence from said sample with a detection system comprises the step of utilizing a photomultiplier tube.

84. A method of flow cytometry sample processing according to claim 60 wherein said step of injecting irradiatable sample comprises the step of staining said sample with fluorescent dye.

85. A method of flow cytometry sample processing according to claim 84 wherein said step of staining said sample with fluorescent dye comprises the step of staining said sample with fluorochrome.

86. A method of flow cytometry sample processing according to claim 85 wherein said step of staining said sample with fluorochrome comprises the step of staining said sample with Hoechst bisbenzimide H33342 fluorochrome.

87. A method of flow cytometry sample processing according to claim 84 or 86 wherein said step of subjecting said irradiatable sample to radiation comprises the step of subjecting said irradiatable sample to radiation having a wavelength appropriate to activate fluorescence in said irradiatable sample.

88. A method of flow cytometry sample processing according to claim 87 wherein said step of subjecting said irradiatable sample to radiation having a wavelength appropriate to activate fluorescence in said irradiatable sample comprises the step of providing a wavelength of said radiation of 355 nm.

89. A method of flow cytometry sample processing according to claim 84 or 86 wherein said step of staining said sample comprises the step of staining said sample for a reduced staining time.

90. A method of flow cytometry sample processing according to claim 89 wherein said step of staining for a reduced time comprises the step of staining said sample for less than about 40 minutes.
91. A method of flow cytometry sample processing according to claim 89 wherein said reduced staining time is selected from a group consisting of
    less than about 35 minutes;
    less than about 30 minutes;
    less than about 25 minutes;
    less than about 20 minutes;
    less than about 15 minutes;
    less than about 10 minutes; and
    less than about 5 minutes.
92. A method of flow cytometry sample processing according to claim 60 or 84 wherein said step of exciting said irradiatable sample with said radiation comprises the step of sufficiently hitting said sample with said radiation to cause said irradiatable sample to emit fluorescence.
93. A method of flow cytometry sample processing according to claim 60 wherein said step of subjecting said irradiatable sample to radiation comprises the step of subjecting said sample with low power radiation.
94. A method of flow cytometry sample processing according to claim 93 wherein said step of subjecting said sample with low power radiation comprises the step providing a low power radiation of less than 300 mW.
95. A method of flow cytometry sample processing according to claim 93 wherein said step of subjecting said sample with low power radiation comprises the step of selecting a low power from the group consisting of:
    less than 350 milliwatt;
    less than 200 milliwatt;
    less than 175 milliwatt;
    less than 100 milliwatt;
    less than 88 milliwatt;
    less than 50 milliwatt; and
    less than 25 milliwatt.
96. A method of flow cytometry sample processing according to claim 60 wherein said step of detecting an amount of said emitted fluorescence from each particle in said sample comprises the step of distinguishing between a first population of particles and a second population of particles wherein said first population of particles emits a different fluorescence from said second population of particles.
97. A method of flow cytometry sample processing according to claim 60 wherein said step of collecting said sorted sample comprises the step of collecting at least two populations of sample particles.
98. A method of flow cytometry sample processing according to claim 97 wherein said step of collecting at least two populations of sample particles comprises the step of collecting a sorted population of X chromosome bearing sperm and collecting a sorted population of Y chromosome bearing sperm.
99. A method of flow cytometry sample processing according to claim 97 or 98 wherein said step of collecting said populations comprises the step of collecting said populations at a high purity.
100. A method of flow cytometry sample processing according to claim 99 wherein said step of collecting said populations at a high purity comprises the step of selecting said high purity from a group consisting of:
    greater than 85% purity;
    greater than 90% purity;
    greater than 95% purity;
    greater than 96% purity; and
    greater than 98% purity.
101. A method of flow cytometry sample processing according to claim 99 wherein said step of collecting said populations at a high purity comprises the step of a providing a high resolution of said sorted sample.
102. A method of flow cytometry sample processing according to claim 101 wherein high resolution of said sorted sample is selected from a group consisting of:
    greater than 7.0;
    greater than 7.5;
    greater than 8.0;
    greater than 8.5;
    greater than 9.0; and
    greater than 9.2.
103. A method of flow cytometry sample processing according to claim 60 wherein said step of sorting said sample comprises the step of sorting said sample cells at a low coincidence rate.
104. A method of flow cytometry sample processing according to claim 103 wherein said low coincidence rate is selected from the group consisting of:
    less than 4400;
    less than 4000;
    less than 3700; and
    less than 3600.
105. A method of flow cytometry sample processing according to claim 97 wherein said step of collecting at least two populations of sample particles comprises the step of collecting said populations at a high collection rate.
106. A method of flow cytometry sample processing according to claim 105 wherein said high collection rate is selected from a group consisting of:
    greater than 2400 particles per second;
    greater than 2600 particles per second;
    greater than 2900 particles per second;
    greater than 3000 particles per second; and
    greater than 3100 particles per second.
107. A method of flow cytometry sample processing according to claim 60 wherein said step of detecting an amount of said emitted fluorescence from each particle in said sample comprises the step of detecting at an event rate of between about 10,000 to about 60,000 particles per second.
108. A method of flow cytometry sample processing according to claim 60 wherein said step of subjecting said irradiatable sample to radiation comprises the step of initiating a sensing routine.
109. A method of flow cytometry sample processing according to claim 68 wherein said step of multiply subjecting said irradiatable sample to radiation for a first amount of time comprises the step multiply subjecting said irradiatable sample to radiation for a first amount of time between about 5 to about 20 picoseconds.
110. A method of flow cytometry sample processing according to claim 68 or 109 multiply terminating said radiation of said irradiatable sample for a second amount of time comprises the step of multiply terminating said radiation of said irradiatable sample for a second amount of time between about 0.5 to about 20 nanoseconds.
111. A method of flow cytometry sample processing according to claim 110 and further comprising providing a repetition rate between about 2 to about 10 microseconds.
112. A method of flow cytometry sample processing according to claim 111 wherein said step of providing a repetition rate comprises the step providing a repetition rate between 50-200 MHz.

113. A method of flow cytometry sample processing according to claim 111 wherein said step of providing a repetition rate comprises the step providing a repetition rate of up to about 80 MHz.

114. A method of flow cytometry sample processing according to claim 84 wherein said step of staining said samples with a fluorescent dye comprises the step of minimally staining said samples with a fluorescent dye.

115. A method of flow cytometry sample processing according to claim 114 wherein said step of minimally staining samples with a fluorescent dye comprises the step of allowing less stain to bind to said sample.

116. A method of flow cytometry sample processing according to claim 114 or 115 wherein said step of minimally staining said samples with a fluorescent dye comprises the step of providing a percentage of stain selected from a group consisting of about 90%, about 80%, about 70% and about 60% of a maximum stain.

117. A method of flow cytometry sample processing according to claim 60 wherein said step of forming a charged drop comprises the step of oscillating said sheath fluid to form said charged drop.

118. A method of flow cytometry sample processing according to claim 64 wherein said step of injecting sperm cells into said at least one sheath fluid comprises injected sperm cells selected from a group consisting of mammals, bovine sperm cells, equine sperm cells, porcine sperm cells, ovine sperm cells, camelid sperm cells, ruminant sperm cells, and canine sperm cells.

119. A method of flow cytometry sample processing according to claim 60 wherein said step of collecting said sorted sample comprises the step of collecting said sorted sample in a collector, wherein said collector is selected from the group consisting of multiple containers and a combined collector having a individual containers.

120. A method of flow cytometry sample processing according to claim 119 further comprising the step of providing a number of selected containers less than a number of nozzles.

121. A method of flow cytometry sample processing according to claim 64 and further comprising the step of utilizing said collected sorted sample for insemination of female mammals.

122. A method of flow cytometry sample processing according to claim 68 wherein said step of multiply subjecting said irradiatable sample to radiation for a first amount of time and said step of multiply terminating said radiation of said irradiatable sample for a second amount of time comprises the step of utilizing a pulsed laser.

123. A method of flow cytometry sample processing according to claim 122 wherein said step of utilizing a pulsed laser selected from a group consisting of Nd:YAG and Nd:YVO$_4$.

124. A method of flow cytometry sample processing according to claim 60 and further comprising the step of individually controlling said at least two nozzles.

125. A method of flow cytometry sample processing according to claim 60 and further comprising the step of compositely controlling said at least two nozzles.

126. A mammal produced through use of a sorted sperm cells produced with a flow cytometer system according to claim 64, 76, or 118.

127. A flow cytometry system for sperm comprising:
a sheath fluid port to introduce a sheath fluid;
a sample injection element having an injection point through which irradiatable sperm cells may be introduced into said sheath fluid;
a nozzle located in part below said injection point;
an oscillator to which said a sheath fluid is responsive;
an intermittingly punctuated radiation emitter;
a sperm cell fluorescence detector;
a processing unit connected to said sperm cell fluorescence detector;
a drop charge circuit to apply an electrical condition to a stream of said irradiatable sperm cells and sheath fluid;
a first and second deflection plate each disposed on opposite sides of a free fall area in which a drop forms, wherein said first and second deflection plates are oppositely charged; and
a sperm cell collector.

128. A flow cytometry system for sperm according to claim 127 wherein said sperm cell fluorescence detector comprises a sperm cell fluorescence quantitative detector.

129. A flow cytometry system for sperm according to claim 128 wherein said sperm cell fluorescence quantitative detector comprises a detector between an X chromosome bearing sperm and a Y chromosome bearing sperm.

130. A flow cytometry system for sperm according to claim 127 and further comprising a rapid sperm sorter.

131. A flow cytometry system for sperm according to claim 130 wherein said rapid sperm sorter comprises a sort rate of greater than 500 cells per second.

132. A flow cytometry system for sperm according to claim 130 wherein said rapid sperm sorter comprises a sort rate selected from a group consisting of
greater than 1000 cells per second;
greater than 1500 cells per second;
greater than 2000 cells per second; and
greater than 3000 cells per second.

133. A flow cytometry system for sperm according to claim 127 and further comprising a radiation beam manipulator.

134. A flow cytometry system for sperm according to claim 133 wherein said radiation beam manipulator is selected from a group consisting mirrors, deflectors, beam splitters, prisms, refractive objects, lenses and filters.

135. A flow cytometry system for sperm according to claim 127 wherein said sperm cell fluorescence detector comprises a photomultiplier tube.

136. A flow cytometry system for sperm according to claim 127 wherein said irradiatable sperm cells comprises stained sperm cells.

137. A flow cytometry system for sperm according to claim 136 wherein said stain comprises fluorochrome.

138. A flow cytometry system for sperm according to claim 137 wherein said stain comprises Hoechst bisbenzimide H33342 fluorochrome 139. A flow cytometry system for sperm according to claim 136 or 137 wherein said stain comprises a large amount of dye.

140. A flow cytometry system for sperm according to claim 139 wherein said large amount of dye comprises dye bound to most of binding sites on a deoxyribonucleic acid.

141. A flow cytometry system for sperm according to claim 136 or 138 wherein said intermittingly punctuated radiation emitter comprises a fluorescence activation wavelength.

142. A flow cytometry system for sperm according to claim 141 wherein said fluorescence activation wavelength comprises 355 nm.

143. A flow cytometry system for sperm according to claim 127 wherein said intermittingly punctuated radiation emitter comprises low power radiation.

144. A flow cytometry system for sperm according to claim 143 wherein said low power radiation comprises less than about 300 mW.

145. A flow cytometry system for sperm according to claim 143 wherein said low power radiation is selected from a group consisting of:
less than 350 milliwatt;
less than 200 milliwatt;
less than 175 milliwatt;
less than 100 milliwatt;
less than 88 milliwatt;
less than 50 milliwatt; and
less than 25 milliwatt.

146. A flow cytometry system for sperm according to claim 127 and further comprising a beam splitter.

147. A flow cytometry system for sperm according to claim 127 wherein said sperm cell fluorescence detector comprises detector between an X chromosome bearing sperm and a Y chromosome bearing sperm.

148. A flow cytometry system for sperm according to claim 127 wherein said sperm collector comprises a X chromosome bearing sperm collector and a Y chromosome sperm collector.

149. A flow cytometry system for sperm according to claim 147 or 148 and further comprising a high purity sorted population of said X chromosome bearing sperm and said Y chromosome bearing sperm.

150. A flow cytometry system for sperm according to claim 149 wherein said high purity is selected from a group consisting of:
greater than 85% purity;
greater than 90% purity;
greater than 95% purity;
greater than 96% purity; and
greater than 98% purity.

151. A flow cytometry system for sperm according to claim 149 and further comprising sorted sperm cells at a high resolution.

152. A flow cytometry system for sperm according to claim 151 wherein said high resolution is selected from a group consisting of:
greater than 7.0;
greater than 7.5;
greater than 8.0;
greater than 8.5;
greater than 9.0; and
greater than 9.2.

153. A flow cytometry system for sperm according to claim 127 and further comprising a low coincidence rate.

154. A flow cytometry system for sperm according to claim 153 wherein said low coincidence rate is selected from the group consisting of:
less than 4400;
less than 4000;
less than 3700; and
less than 3600.

155. A flow cytometry system for sperm according to claim 148 and further comprising a high collection rate.

156. A flow cytometry system for sperm according to claim 155 wherein said high collection rate is selected from a group consisting of:
greater than 2400 sperm per second;
greater than 2600 sperm per second;
greater than 2900 sperm per second;
greater than 3000 sperm per second; and
greater than 3100 sperm per second.

157. A flow cytometry system for sperm according to claim 127 and further comprising an event rate between about 10,000 to about 60,000 sperm cells per second.

158. A flow cytometry system for sperm according to claim 127 wherein said intermittingly punctuated radiation emitter comprises a radiation time between about to about 20 picoseconds.

159. A flow cytometry system for sperm according to claim 127 or 158 wherein said intermittingly punctuated radiation emitter comprises a radiation off time between about 0.5 to about 20 nanoseconds.

160. A flow cytometry system for sperm according to claim 159 and further comprising a repetition rate between about 2 to about 10 microseconds.

161. A flow cytometry system for sperm according to claim 160 wherein said repetition rate comprises between about 50 to about 200 MHz.

162. A flow cytometry system for sperm according to claim 160 wherein said repetition rate comprises up to about 80 MHz.

163. A flow cytometry system for sperm according to claim 136 wherein said stained sperm cells comprises a minimum sperm stain.

164. A flow cytometry system for sperm according to claim 163 wherein said minimum sperm stain comprises less stain bound to said sperm cells.

165. A flow cytometry system for sperm according to claim 163 or 164 wherein said minimum sperm stain comprises a percentage of stain selected from a group consisting of about 90%, about 80%, about 70% and about 60% of a maximum stain.

166. A flow cytometry system for sperm according to claim 127 wherein said sperm cells comprises sperm cells selected from a group consisting of mammal sperm cells, bovine sperm cells, equine sperm cells, porcine sperm cells, ovine sperm cells, camelid sperm cells, ruminant sperm cells, and canine sperm cells.

167. A flow cytometry system for sperm according to claim 127 wherein said nozzle comprises at least two nozzles.

168. A flow cytometry system for sperm according to claim 167 wherein said sperm cell collector is selected from the group consisting of multiple containers and a combined collector having a individual containers.

169. A flow cytometry system for sperm according to claim 168 and further comprising a number of selected containers less than a number of nozzles.

170. A flow cytometry system for sperm according to claim 127 or 167 and further comprising at least one shared resource.

171. A flow cytometry system for sperm according to claim 170 wherein said shared resource comprises one intermittingly punctuated radiation emitter and a beam splitter.

172. A flow cytometry system for sperm according to claim 127 wherein said intermittingly punctuated radiation emitter comprises pulsed laser.

173. A flow cytometry system for sperm according to claim 172 wherein said pulsed laser is selected from a group consisting of Nd:YAG and Nd:YVO$_4$.

174. A mammal produced through use of a sorted sperm cell produced with a flow cytometer system according to claim 127, 128, 144, 158, or 166.

175. A flow cytometry system comprising:
at least one sheath fluid port to introduce a sheath fluid;
at least one sample injection element having an injection point through which an irradiatable sample may be introduced into said sheath fluid;

at least two nozzles located in part below said at least one injection point;
an oscillator to which said sheath fluid is responsive;
a radiation emitter;
a particle sample fluorescence detector;
a processing unit connected to said particle sample fluorescence detector;
a drop charge circuit to apply an electrical condition to a stream of said irradiatable sample cells and sheath fluid;
a first and second deflection plate each disposed on opposite sides of a free fall area in which a drop forms, wherein said first and second deflection places are oppositely charged; and
a particle sample collector.

176. A flow cytometry system according to claim 175 wherein said sample comprises usable cells.
177. A flow cytometry system according to claim 176 wherein said usable cells comprises reproductive cells.
178. A flow cytometry system according to claim 177 wherein said reproductive cells comprises haploid cells.
179. A flow cytometry system according to claim 178 wherein said haploid cells comprises sperm cells.
180. A flow cytometry system according to claim 175 wherein said sample comprises delicate sample.
181. A flow cytometry system according to claim 175 wherein said sample comprises sample is selected from a group consisting of non-biological particles, biological particles and sperm.
182. A flow cytometry system according to claim 175 wherein said radiation emitter comprises a continuous wave laser.
183. A flow cytometry system according to claim 175 wherein said radiation emitter comprises an intermittingly punctuated radiation emitter.
184. A flow cytometry system according to claim 175 and further comprising at least one shared resource.
185. A flow cytometry system according to claim 184 wherein said shared resource comprises one radiation emitter and a beam splitter.
186. A flow cytometry system according to claim 175 and further comprising a beam splitter.
187. A flow cytometry system according to claim 175 wherein said particle sample cell fluorescence detector comprises a particle sample cell fluorescence quantitative detector.
188. A flow cytometry system according to claim 187 wherein said particle sample fluorescence quantitative detector comprises a detector between two different particles.
189. A flow cytometry system according to claim 187 wherein said sample comprises sperm cells and wherein said sperm cell fluorescence quantitative detector comprises detector between an X chromosome bearing sperm and a Y chromosome bearing sperm.
190. A flow cytometry system according to claim 175 and further comprising a rapid particle sample sorter.
191. A flow cytometry system according to claim 190 wherein said rapid particle sample sorter comprises a sort rate of greater than 500 cells per second.
192. A flow cytometry system according to claim 190 wherein said rapid particle sample sorter comprises a sort rate selected from a group consisting of:
greater than 1000 cells per second;
greater than 1500 cells per second;
greater than 2000 cells per second; and
greater than 3000 cells per second.
193. A flow cytometry system according to claim 175 and further comprising a radiation beam manipulator.
194. A flow cytometry system according to claim 193 wherein said radiation beam manipulator is selected from a group consisting mirrors, deflectors, beam splitters, prisms, refractive objects, lenses and filters.
195. A flow cytometry system according to claim 175 wherein said fluorescence detector comprises a photomultiplier tube.
196. A flow cytometry system according to claim 175 wherein said irradiatable sample comprises a stained sample.
197. A flow cytometry system according to claim 196 wherein said stain comprises fluorochrome.
198. A flow cytometry system according to claim 197 wherein said stain comprises Hoechst bisbenzimide H33342 fluorochrome.
199. A flow cytometry system according to claim 196 or 198 wherein said radiation emitter comprises a fluorescence activation wavelength.
200. A flow cytometry system according to claim 199 wherein said fluorescence activation wavelength comprises 355 nm.
201. A flow cytometry system according to claim 175 wherein said radiation emitter comprises low power radiation.
202. A flow cytometry system according to claim 201 wherein said low power radiation comprises less than 300 mW.
203. A flow cytometry system according to claim 201 wherein said low power radiation is selected from a group consisting of:
less than 350 milliwatt;
less than 200 milliwatt;
less than 175 milliwatt;
less than 100 milliwatt;
less than 88 milliwatt;
less than 50 milliwatt; and
less than 25 milliwatt.
204. A flow cytometry system according to claim 175 a detector between two different particles.
205. A flow cytometry system according to claim 175 wherein said particle sample collector comprises a collector of at least two populations of particles.
206. A flow cytometry system according to claim 205 wherein said collector of at least two populations of particles comprises a X chromosome bearing sperm collector and a Y chromosome sperm collector.
207. A flow cytometry system according to claim 205 or 206 and further comprising a high purity of said sorted populations.
208. A flow cytometry system according to claim 207 wherein said high purity is selected from a group consisting of:
greater than 85% purity;
greater than 90% purity;
greater than 95% purity;
greater than 96% purity; and
greater than 98% purity.
209. A flow cytometry system according to claim 207 and further comprising a sorted sample at a high resolution.
210. A flow cytometry system according to claim 209 wherein said high resolution is selected from a group consisting of:
greater than 7.0;
greater than 7.5;
greater than 8.0;
greater than 8.5;
greater than 9.0; and
greater than 9.2.
211. A flow cytometry system according to claim 175 and further comprising a low coincidence rate.
212. A flow cytometry system according to claim 211 wherein said low coincidence rate is selected from the group consisting of:

less than 4400;
less than 4000;
less than 3700; and
less than 3600.
213. A flow cytometry system according to claim 205 and further comprising a high collection rate.
214. A flow cytometry system according to claim 213 wherein said high collection rate is selected from a group consisting of:
greater than 2400 particles per second;
greater than 2600 particles per second;
greater than 2900 particles per second;
greater than 3000 particles per second; and
greater than 3100 particles per second.
215. A flow cytometry system according to claim 175 and further comprising an event rate between about 10,000 to about 60,000 particles per second.
216. A flow cytometry system according to claim 183 wherein said intermittingly punctuated radiation emitter comprises a radiation time between about 5 to about 20 picoseconds.
217. A flow cytometry system according to claim 183 or 216 intermittingly punctuated radiation emitter comprises a radiation off time between about 0.5 to about 20 nanoseconds.
218. A flow cytometry system according to claim 217 and further comprising a repetition rate between about 2 to about 10 microseconds.
219. A flow cytometry system according to claim 218 wherein said repetition rate comprises between about 50 to about 200 MHz.
220. A flow cytometry system according to claim 218 wherein said repetition rate comprises up to about 80 MHz.
221. A flow cytometry system according to claim 196 wherein said stained sample comprises a minimum sample stain.
222. A flow cytometry system according to claim 221 wherein said minimum sample stain comprises less stain bound to said sample particles.
223. A flow cytometry system according to claim 221 or 222 wherein said minimum stain comprises a percentage of stain selected from a group consisting of about 90%, about 80%, about 70% and about 60% of a maximum stain.
224. A flow cytometry system according to claim 179 wherein said sperm cells comprises sperm cells selected from a group consisting of mammal sperm cells, bovine sperm cells, equine sperm cells, porcine sperm cells, ovine sperm cells, camelid sperm cells, ruminant sperm cells, and canine sperm cells.
225. A flow cytometry system according to claim 175 wherein said particle sample collector is selected from the group consisting of multiple containers and a combined collector having a individual containers.
226. A flow cytometry system according to claim 225 and further comprising a number of selected particle containers less than a number of nozzles.
227. A flow cytometry system according to claim 183 wherein said intermittingly punctuated radiation emitter comprises a pulsed laser.
228. A flow cytometry system according to claim 227 said pulsed laser is selected from a group consisting of Nd:YAG and Nd:YVO$_4$.
229. A flow cytometry system according to claim 175 and further comprising an individual nozzle control.
230. A flow cytometry system according to claim 175 and further comprising a composite nozzle control.
231. A mammal produced through use of a sorted sperm cell produced with a flow cytometer system according to claim 179, 189, 224.

As can be easily understood from the foregoing, the basic concepts of the present invention may be embodied in a variety of ways. It involves both sorting techniques as well as devices to accomplish the appropriate sorting system. In this application, the sorting techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims included in this or in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. This patent application seeks examination of as broad a base of claims as deemed within the applicant's right and is designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed herein and in the table of references as listed below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. PATENT DOCUMENTS

| DOCUMENT NO | DATE | NAME | CLASS | SUBCLASS | FILING DATE |
|---|---|---|---|---|---|
| 2002/0113965 A1 | Aug. 22, 2002 | Roche et al. | 356 | 339 | Oct. 02, 2001 |
| 2002/0141902 A1 | Oct. 03, 2002 | Ozasa et al. | 422 | 85.09 | Mar. 27, 2002 |
| 2002/0186375 A1 | Dec. 12, 2002 | Asbury et al. | 356 | 440 | May 01, 2001 |
| 2003/0098421 A1 | May 29, 2003 | Ho | 250 | 458.1 | Nov. 27, 2001 |
| 2003/0207461 A1 | Nov. 06, 2003 | Bell et al. | 436 | 172 | Nov. 14, 2001 |
| 2003/0209059 A1 | Nov. 13, 2003 | Kawano et al. | 73 | 53.01 | Mar. 28, 2003 |
| 2004/0005582 A1 | Jan. 08, 2004 | Shipwash | 435 | 6 | Dec. 19, 2002 |
| 3,893,766 | Jul. 08, 1975 | Hogg | 356 | 36 | Jun. 14, 1973 |
| 4,362,246 | Dec. 07, 1982 | Adair | 209 | 3.3 | Jun. 14, 1980 |
| 4,660,971 | Apr. 28, 1987 | Sage et al. | 356 | 39 | May 03, 1984 |
| 4,988,619 | Jan. 29, 1991 | Pinkel | 435 | 30 | Nov. 30, 1987 |
| 5,088,816 | Feb. 18, 1992 | Tomioka et. al | 356 | 39 | Mar. 06, 1990 |
| 5,135,759 | Aug. 04, 1992 | Johnson | 424 | 561 | Apr. 26, 1991 |
| 5,315,122 | May 24, 1994 | Pinsky, et al. | 250 | 461.2 | |
| 5,371,585 | Dec. 06, 1994 | Morgan et al. | 356 | 246 | Nov. 10, 1992 |
| 5,439,362 | Aug. 08, 1995 | Spaulding | 424 | 185.1 | Jul. 25, 1994 |
| 5,466,572 | Nov. 14, 1995 | Sasaki et al. | 435 | 2 | Apr. 25, 1994 |
| 5,483,469 | Jan. 09, 1996 | Van den Engh et al. | 364 | 555 | Aug. 02, 1993 |
| 5,596,401 | Jan. 21, 1997 | Kusuzawa | 356 | 23 | Sep. 14, 1994 |
| 5,602,039 | Feb. 11, 1997 | Van den Engh | 436 | 164 | Oct. 14, 1994 |
| 5,602,349 | Feb. 11, 1997 | Van den Engh | 73 | 864.85 | Oct. 14, 1994 |
| 5,660,997 | Aug. 26, 1997 | Spaulding | 435 | 7.21 | Jun. 07, 1995 |
| 5,690,895 | Nov. 25, 1997 | Matsumoto et al. | 422 | 73 | Dec. 06, 1996 |
| 5,700,692 | Dec. 23, 1997 | Sweet | 436 | 50 | Sep. 27, 1994 |
| 5,726,364 | Mar. 10, 1998 | Van den Engh | 73 | 864.85 | Feb. 10, 1997 |
| 5,793,485 | Aug. 11, 1998 | Gourley | 356 | 318 | Jan. 13, 1997 |
| 5,895,922 | Apr. 20, 1999 | Ho | 250 | 491.2 | May 23, 1997 |
| 5,985,216 | Nov. 16, 1999 | Rens, et al. | 422 | 73 | Jul. 24, 1997 |
| 6,149,867 | Nov. 21, 2000 | Siedel, et al. | 422 | 73 | Dec. 31, 1997 |
| 6,177,277 B1 | Jan. 23, 2001 | Soini | 436 | 63 | Jan. 03, 1996 |
| 6,263,745 | Jul. 24, 2001 | Buchanan, et al. | | | Dec. 03, 1999 |
| 6,357,307 | Mar. 19, 2002 | Buchanan, et al. | 73 | 865.5 | Jul. 20, 2001 |
| 6,411,835 B1 | Jun. 25, 2002 | Modell et al. | 600 | 407 | Feb. 02, 1999 |
| 6,463,314 B1 | Oct. 08, 2002 | Haruna | 600 | 407 | Feb. 19, 1999 |
| 6,528,802 | Mar. 04, 2003 | Karsten, et al. | 250 | 459.1 | Jun. 01, 2001 |
| 6,534,308 B1 | Mar. 18, 2003 | Palsson et al. | 435 | 288.7 | Nov. 30, 1999 |
| 6,537,829 | Mar. 25, 2003 | Zarling, et al. | 436 | 514 | Dec. 01, 1999 |
| 6,577,387 B2 | Jun. 10, 2003 | Ross, III et al. | 356 | 124 | Dec. 29, 2000 |
| 6,590,911 B1 | Jul. 08, 2003 | Spinelli et al | 372 | 22 | Jun. 02, 2000 |
| 6,604,435 | Mar. 13, 2002 | Buchanan, et al. | | | Aug. 12, 2003 |
| 6,618,679 B2 | Sep. 09, 2003 | Loehrlein et al. | 702 | 20 | Jan. 27, 2001 |
| 6,642,018 B1 | Nov. 04, 2003 | Koller et al. | 435 | 40.5 | Mar. 13, 2000 |
| 6,667,830 B1 | Dec. 23, 2003 | Iketaki et al. | 359 | 368 | Apr. 09, 1999 |
| 6,671,044 B2 | Dec. 30, 2003 | Ortyn et al. | 356 | 326 | Nov. 16, 2001 |
| 6,673,095 B2 | Jan. 06, 2004 | Nordquist | 607 | 89 | Feb. 12, 2001 |

II. FOREIGN PATENT DOCUMENTS

| DOCUMENT NO | DATE | COUNTRY |
|---|---|---|
| EP 0 288 029 | Apr. 20, 1988 | Europe |
| WO 96/12171 | Apr. 25, 1996 | PCT |
| WO 98/34094 | Aug. 06, 1998 | PCT |
| WO 99/05504 | Jul. 24, 1998 | PCT |
| WO 99/33956 | Jul. 08, 1999 | PCT |
| WO 01/40765 | Jun. 07, 2001 | PCT |
| WO 01/40765 | Jul. 06, 2001 | PCT |
| WO 01/85913 | Nov. 15, 2001 | PCT |

III. OTHER DOCUMENTS (Including Author, Title, Date, Pertinent Pages, Etc.)

Dean, P. N., et al., "Hydrodynamic orientation of spermatozoa heads for flow cytometry", Biophysical Journal. 23: 7-13, 1978

Elmes, R. S., et al., "Evaluation of the Spectra Physics Vanguard laser as a new UV light source for Flow Cytometry," Laboratory for Cell Analysis, Comprehensive Cancer Center, University of California, 4 pages _ (Date)

Fulwyler, M. J. 1977. Hydrodynamic orientation of cells. J Histochem. Cytochem. 25: 781-783.

Gurnsey, M. P., and Johnson, L. A., "Recent improvements in efficiency of flow cytometric sorting of X and Y-chromosome bearing sperm of domestic animals: a review", 1998, New Zealand Society of Animal Protection, three pages.

Johnson, L. A., et al., "Enhanced flow cytometric sorting of mammalian X and Y sperm: high speed sorting and orienting No. 77.1e for artificial insemination", Theriogenology. 49(1): 361. abstr., 1998

Johnson L. A., et al., "Flow cytometry of X- and Y-chromosome bearing sperm for DNA using an improved preparation method and staining with Hoechst 333-42", Garnete Research 17: 203-212, 1987

Johnson L. A., et al., "Modification of a laser-based flow cytometer for high resolution DNA analysis of mammalian spermatozoa", Cytometry 7: 266-273, 1986

Johnson, L. A., et al., "Improved flow sorting resolution of X- and Y-chromosome bearing viable sperm separation using dual staining and dead cell gating", Cytometry 17 (suppl 7): 83, 1994

Johnson, L. A., et al., "Sex Preselection: High Speed Flow Cytometric Sorting of X and Y sperm for Maximum efficiency", Theriogenology 52: 1323-1341, 1999

Johnson L. A., et al., "Sex preseletion in rabbits: Live births from X and Y sperm separated by DNA and cell sorting", Bio Reprod 41: 199-203, 1989.

Kachel, V., et al., "Uniform Lateral Orientation, Caused by Flow Forces, of Flat Particles in Flow-Through Systems", The Journal of Histochemistry and Cytochemistry, 1997, Vol. 25, No. 7, pp 774-780.

Lightwave Electronics, "Xcyte", www.LightwaveElectronics.com, 2 pp.

"Introducing the Vanguard - 4 Watts of UV from a Quasi-cw, all solid state laser," LaserForefront, A Monthly Update On The State Of Technologies In The Laser Industry 2001, No. 30

Rens, W., et al., "Improved Flow Cytometric Sorting of X- and Y-Chromosome Bearing Sperm: Substantial Increase in Yield of Sexed Semen", Molecular Reproduction and Development, 1999, pp 50-56.

Rens, W., et al., "A Novel Nozzle for More Efficient Sperm Orientation to Improve Sorting Efficiency of X and Y Chromosome-Bearing Sperm", Technical Notes, Cytometry 33, 1998, pp 476-481.

Siedel, G. E. Jr., Herickhoff, L. A., Schenk, J. L., Doyle, S. P. and Green, R. D. 1998. Artificial insemination of heifers with cooled, unfrozen, and sexed semen. 1998. Theriogenology. 49(1): 365

Spectra-Physics Products "FCbar$^{tm}$," 2 pages, printed Nov. 14, 2002

Spectra-Physics, The Solid State Laser Company "Vanguard 4 Watts of UV from a quasi-cw, all solid state laser.", 3 pages, printed Nov. 14, 2002

Spectra-Physics, The Solid State Laser Company, "Vanguard 350-HMD 355, www.spectra-physics.com, 3 pp.

Spectra-Physics, The Solid State Laser Company, "Vanguard 2000-HM 532, www.spectra-physics.com, 3 pp.

Time-Bandwidth ® Products, "GE-100-XHP", www.tbwp.com, 2 pages, January 2002.

US National Phase Application Number 09/355,461 filed Sep. 17, 1999

Welch G. R., et al., "Fluidic and optical modifications to a FACS IV for flow sorting of X- and Y-chromosome bearing sperm based on DNA", Cytometry 17 (suppl. 7): 74, 1994

In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

What is claimed is:

1. A method of flow cytometry sperm processing comprising the steps of:

establishing a sheath fluid;

flowing said sheath fluid into at least one nozzle;

providing a percentage of a fluorescent dye stain as compared to a standard control, said percentage of stain selected from a group consisting of about 90%, about 80%, about 70%, and about 60% of maximum stain;

staining sperm cells with said percentage of said fluorescent dye stain to provide irradiatable stained sperm cells;

injecting said irradiatable stained sperm cells into said sheath fluid;

utilizing one radiation source;

splitting a radiation into at least two beams;

directing each of said beams to said at least one nozzle and said sperm cells;
multiply subjecting said irradiatable sperm cells to said radiation for a first amount of time;
multiply terminating said radiation of said irradiatable sperm cells for a second amount of time;
multiply exciting said irradiatable sperm cells with said radiation;
wherein said step of multiply subjecting said irradiatable sperm cells to said radiation for said first amount of time and said step of multiply terminating said radiation of said irradiatable sperm cells for said second amount of time and said step of multiply exciting said irradiatable sperm cells with said radiation are performed in a sequential manner then repeated in order at a repetition rate;
emitting fluorescence from said excited sperm cells;
detecting an amount of said emitted fluorescence from each of said sperm cells;
evaluating said amount of emitted fluorescence from each of said sperm cells;
selecting an electrical condition based on the amount of emitted and detected fluorescence from each of said sperm cells to be associated with each of said sperm cells in said sheath fluid flow;
charging a stream of said irradiatable sperms cell and sheath fluid based on the amount of emitted and detected fluorescence from each of said sperm cells in said sheath fluid flow;
forming a charged drop having one of said sperm cells located therein;
isolating said charged drop from said sheath fluid flow;
deflecting said charged drops;
sorting said sperm cells; and
collecting said sorted sperm cells.

2. A method of flow cytometry sperm processing according to claim 1 wherein said step of detecting an amount of said emitted fluorescence from each of said sperm cells comprises the step of quantitatively detecting an amount of said emitted fluorescence from each of said sperm cells.

3. A method of flow cytometry sperm processing according to claim 2 wherein said step of quantitatively detecting an amount of said emitted fluorescence from each of said sperm cells comprises the step of distinguishing between a X-chromosome bearing sperm and a Y-chromosome bearing sperm wherein said X-chromosome bearing sperm emits a different fluorescence from said Y-chromosome bearing sperm.

4. A method of flow cytometry sperm processing according to claim 1 wherein said step of sorting said sperm cells comprises the step of rapidly sorting said sperm cells at a rate greater than 500 cells per second.

5. A method of flow cytometry sperm processing according to claim 1 wherein said step of sorting said sperm cells comprises the step of rapidly sorting said sperm cells at a rate selected from a group consisting of:
greater than 1000 cells per second;
greater than 1500 cells per second;
greater than 2000 cells per second; and
greater than 3000 cells per second.

6. A method of flow cytometry sperm processing according to claim 1 and further comprising the step of utilizing a beam manipulator.

7. A method of flow cytometry sperm processing according to claim 6 wherein said step of utilizing a beam manipulator comprises the step of utilizing a beam manipulator selected from a group consisting of mirrors, deflectors, beam splitters, prisms, refractive objects, lenses and filters.

8. A method of flow cytometry sperm processing according to claim 1 wherein said step of detecting an amount of said emitted fluorescence from each of said sperm cells comprises the step of detecting an amount of said emitted fluorescence from each of said sperm cells with a detection system.

9. A method of flow cytometry sperm processing according to claim 8 wherein said step of detecting an amount of said emitted fluorescence from each of said sperm cells with a detection system comprise the step of utilizing a photomultiplier tube.

10. A method of flow cytometry sperm processing according to claim 1 wherein said step of staining said sperm with said fluorescent dye comprises the step of staining said sperm with fluorochrome.

11. A method of flow cytometry sperm processing according to claim 1 wherein said step of multiply subjecting said irradiatable sperm cells to radiation for a first amount of time comprises the step of multiply subjecting said irradiatable sperm cells to radiation having a wavelength appropriate to activate fluorescence in said irradiatable sperm.

12. A method of flow cytometry sperm processing according to claim 11 wherein said step of multiply subjecting said irradiatable sperm cells to radiation having a wavelength appropriate to activate fluorescence in said irradiatable sperm comprises the step of providing a wavelength of said radiation of 355 nm.

13. A method of flow cytometry sperm processing according to claim 1 wherein said step of staining said sperm with said fluorescent dye comprises the step of staining said sperm for a reduced staining time of less than about 40 minutes.

14. A method of flow cytometry sperm processing according to claim 1 wherein said step of staining said sperm with said fluorescent dye comprises the step of staining said sperm for a reduced staining time selected from a group consisting of:
less than about 35 minutes;
less than about 30 minutes;
less than about 25 minutes;
less than about 20 minutes;
less than about 15 minutes;
less than about 10 minutes; and
less than about 5 minutes.

15. A method of flow cytometry sperm processing according to claim 1 wherein said step of multiply exciting said irradiatable sperm cells with said radiation comprises the step of sufficiently hitting said sperm with said radiation to cause said irradiatable sperm to emit fluorescence.

16. A method of flow cytometry sperm processing according to claim 1 wherein said step of multiply subjecting said irradiatable sperm cells to radiation for a first amount of time comprises the step of multiply subjecting said irradiatable sperm cells to low power radiation of less than 300 mW.

17. A method of flow cytometry sperm processing according to claim 1 wherein said step of multiply subjecting said irradiatable sperm cells to radiation for a first amount of time comprises the step of multiply subjecting said irradiatable sperm cells to low power radiation selected from the group consisting of:
less than 350 milliwatt;
less than 200 milliwatt;
less than 175 milliwatt;
less than 100 milliwatt;
less than 88 milliwatt;
less than 50 milliwatt; and
less than 25 milliwatt.

18. A method of flow cytometry sperm processing according to claim 1 wherein said step of splitting said radiation into at least two light beams comprises the step of subjecting said sperm cells with a reduced power of radiation than which was originally emitted from a laser source.

19. A method of flow cytometry sperm processing according to claim 18 wherein said step of subjecting said sperm cells with a reduced power of radiation than which was originally emitted from a laser source comprises the step selecting said reduced power from a group consisting of a half, a fourth and an eighth said originally emitted power.

20. A method of flow cytometry sperm processing according to claim 1 wherein said step of detecting an amount of said emitted fluorescence from each of said sperm cells comprises the step of distinguishing between a X chromosome bearing sperm and a Y chromosome bearing sperm wherein said X chromosome bearing sperm emits a different fluorescence from said Y chromosome bearing sperm.

21. A method of flow cytometry sperm processing according to claim 1 wherein said step of collecting said sorted sperm cells comprises the step of collecting a sorted population of X chromosome bearing sperm and collecting a sorted population of Y chromosome bearing sperm.

22. A method of flow cytometry sperm processing according to claim 21 wherein said step of collecting a sorted population of X chromosome bearing sperm and collecting a sorted population of Y chromosome bearing sperm comprises the step of collecting said populations at a high purity, wherein said high purity is selected from a group consisting of:
    greater than 85% purity;
    greater than 90% purity;
    greater than 95% purity;
    greater than 96% purity; and
    greater than 98% purity.

23. A method of flow cytometry sperm processing according to claim 21 and further comprising the step of providing high resolution of said sorted sperm, said high resolution selected from a group consisting of:
    greater than 7.0;
    greater than 7.5;
    greater than 8.0;
    greater than 8.5;
    greater than 9.0; and
    greater than 9.2.

24. A method of flow cytometry sperm processing according to claim 21 wherein said step of collecting a sorted population of X chromosome bearing sperm and collecting a sorted population of Y chromosome bearing sperm comprises the step of collecting said populations at a high collection rate selected from a group consisting of:
    greater than 2400 sperm per second;
    greater than 2600 sperm per second;
    greater than 2900 sperm per second;
    greater than 3000 sperm per second; and
    greater than 3100 sperm per second.

25. A method of flow cytometry sperm processing according to claim 1 wherein said step of sorting said sperm cells comprising the step of sorting said sperm cells at a low coincidence rate selected from the group consisting of:
    less than 4400;
    less than 4000;
    less than 3700; and
    less than 3600.

26. A method of flow cytometry sperm processing according to claim 1 wherein said step of detecting an amount of said emitted fluorescence from each of said sperm cells comprises the step of detecting said sperm cells at an event rate of between about 10,000 to about 60,000 sperm cells per second.

27. A method of flow cytometry sperm processing according to claim 1 wherein said step of multiply subjecting said irradiatable sperm cells to radiation comprises the step of initiating a sensing routine.

28. A method of flow cytometry sperm processing according to claim 1 wherein said step of multiply subjecting said irradiatable sperm cells to radiation for a first amount of time comprises the step multiply subjecting said irradiatable sperm cells to radiation for a first amount of time between about 5 to about 20 picoseconds.

29. A method of flow cytometry sperm processing according to claim 1 wherein said step of multiply terminating said radiation of said irradiatable sperm cells for a second amount of time comprises the step of multiply terminating said radiation of said irradiatable sperm cells for a second amount of time between about 0.5 to about 20 nanoseconds.

30. A method of flow cytometry sperm processing according to claim 29 and further comprising providing said repetition rate between about 2 to about 10 microseconds.

31. A method of flow cytometry sperm processing according to claim 30 wherein said step of providing a repetition rate comprises the step of providing a repetition rate between 50-200 MHz.

32. A method of flow cytometry sperm processing according to claim 30 wherein said step of providing a repetition rate comprises the step of providing a repetition rate of up to about 80 MHz.

33. A method of flow cytometry sperm processing according to claim 1 wherein said step of forming a charged drop comprises the step of oscillating said sheath fluid to form said charged drop.

34. A method of flow cytometry sperm processing according to claim 1 wherein said step of injecting irradiatable sperm cells into said sheath fluid comprises injected sperm cells selected from a group consisting of mammals, bovine sperm cells, equine sperm cells, porcine sperm cells, ovine sperm cells, camelid sperm cells, ruminant sperm cells, and canine sperm cells.

35. A method of flow cytometry sperm processing according to claim 1 wherein said step of flowing said sheath fluid into said at least one nozzle comprises the step of flowing at least one sheath fluid and said sperm cells into at least two nozzles.

36. A method of flow cytometry sperm processing according to claim 35 and further comprising the step of collecting X chromosome bearing sperm populations and Y chromosome bearing sperm populations in a collector, wherein said collector is selected from the group consisting of multiple containers and a combined collector having a individual containers.

37. A method of flow cytometry sperm processing according to claim 36 and further comprising the step of providing a number of selected containers less than a number of nozzles.

38. A method of flow cytometry sperm processing according to claim 1 and further comprising the step of subjecting said radiation to at least two nozzles of identical flow cytometers.

39. A method of flow cytometry sperm processing according to claim 1 and further comprising the step of utilizing said collected sorted sperm for insemination of female mammals.

40. A method of flow cytometry sperm processing according to claim 1 wherein said steps of multiply subjecting said irradiatable sperm cells to radiation for a first amount of time and multiply terminating said radiation of said irradiatable sperm cells for a second amount of time comprises the step of utilizing a pulsed laser.

41. A method of flow cytometry sperm processing according to claim 40 wherein said step of utilizing a pulsed laser comprises the step of a utilizing said pulsed laser selected from a group consisting of Nd:YAG and Nd:YVO$_4$.

42. A flow cytometry system for sperm comprising:
a sheath fluid port to introduce a sheath fluid;
a sample injection element having an injection point through which irradiatable sperm cells may be introduced into said sheath fluid, said irradiatable sperm cells comprises stained sperm cells having a percentage of stain as compared to a standard control, said percentage of stain selected from a group consisting of about 90%, about 80%, about 70%, and about 60% of maximum stain;
a nozzle located in part below said injection point;
an oscillator to which said a sheath fluid is responsive;
a pulsed laser;
a beam splitter;
a sperm cell fluorescence detector to detect fluorescence from said irradiatable sperm cells located in a stream flowing out of said nozzle; said sperm cell fluorescence detector located near said stream of irradiatable sperm cells;
a processing unit connected to said sperm cell fluorescence detector to evaluate detected fluorescence from said irradiatable sperm cells;
a drop charge circuit located near said stream of irradiatable sperm cells flowing out of said nozzle to apply an electrical condition to a stream of said irradiatable sperm cells and sheath fluid, said drop charge circuit is responsive to said processing unit and applies said electrical condition based on said evaluated detected fluorescence;
a first and second deflection plate responsive to said processing unit, each plate disposed on opposite sides of a free fall area in which a drop forms, wherein said first and second deflection plates are oppositely charged; and
a sperm cell collector located below said first and second deflection plates.

43. A flow cytometry system for sperm according to claim 42 wherein said sperm cell fluorescence detector comprises a sperm cell fluorescence quantitative detector.

44. A flow cytometry system for sperm according to claim 43 wherein said sperm cell fluorescence quantitative detector comprises a detector between an X chromosome bearing sperm and a Y chromosome bearing sperm.

45. A flow cytometry system for sperm according to claim 42 and further comprising a rapid sperm sorter having a sort rate of greater than 500 cells per second.

46. A flow cytometry system for sperm according to claim 42 and further comprising a rapid sperm sorter having a sort rate selected from a group consisting of
greater than 1000 cells per second;
greater than 1500 cells per second;
greater than 2000 cells per second; and
greater than 3000 cells per second.

47. A flow cytometry system for sperm according to claim 42 and further comprising a radiation beam manipulator.

48. A flow cytometry system for sperm according to claim 47 wherein said radiation beam manipulator is selected from a group consisting mirrors, deflectors, beam splitters, prisms, refractive objects, lenses and filters.

49. A flow cytometry system for sperm according to claim 42 wherein said sperm cell fluorescence detector comprises a photomultiplier tube.

50. A flow cytometry system for sperm according to claim 42 wherein said stain comprises fluorochrome.

51. A flow cytometry system for sperm according to claim 42 wherein said pulsed laser comprises a fluorescence activation wavelength of 355 nm.

52. A flow cytometry system for sperm according to claim 42 wherein said pulsed laser comprises low power radiation of less than about 300 mW.

53. A flow cytometry system for sperm according to claim 42 wherein said pulsed laser comprises low power radiation selected from a group consisting of:
less than 350 milliwatt;
less than 200 milliwatt;
less than 175 milliwatt;
less than 100 milliwatt;
less than 88 milliwatt;
less than 50 milliwatt; and
less than 25 milliwatt.

54. A flow cytometry system for sperm according to claim 42 wherein said sperm cell fluorescence detector comprises detector between an X chromosome bearing sperm and a Y chromosome bearing sperm.

55. A flow cytometry system for sperm according to claim 54 and further comprising a high purity population of said X chromosome bearing sperm and said Y chromosome bearing sperm selected from a group consisting of:
greater than 85% purity;
greater than 90% purity;
greater than 95% purity;
greater than 96% purity; and
greater than 98% purity.

56. A flow cytometry system for sperm according to claim 54 and further comprising sorted sperm cells at a high resolution selected from a group consisting of:
greater than 7.0;
greater than 7.5;
greater than 8.0;
greater than 8.5;
greater than 9.0; and
greater than 9.2.

57. A flow cytometry system for sperm according to claim 42 wherein said sperm collector comprises a X chromosome bearing sperm collector and a Y chromosome sperm collector.

58. A flow cytometry system for sperm according to claim 57 and further comprising a high collection rate selected from a group consisting of:
greater than 2400 sperm per second;
greater than 2600 sperm per second;
greater than 2900 sperm per second;
greater than 3000 sperm per second; and
greater than 3100 sperm per second.

59. A flow cytometry system for sperm according to claim 42 and further comprising a low coincidence rate selected from the group consisting of:
less than 4400;
less than 4000;
less than 3700; and
less than 3600.

60. A flow cytometry system for sperm according to claim 42 wherein said pulsed laser comprises a radiation time between about 5 to about 20 picoseconds.

61. A flow cytometry system for sperm according to claim 60 wherein said pulsed laser comprises a radiation off time between about 0.5 to about 20 nanoseconds.

62. A flow cytometry system for sperm according to claim 61 and further comprising a repetition rate of said radiation time and said radiation off time between about 2 to about 10 microseconds.

63. A flow cytometry system for sperm according to claim 62 wherein said repetition rate comprises between about 50 to about 200 MHz.

64. A flow cytometry system for sperm according to claim 62 wherein said repetition rate comprises up to about 80 MHz.

65. A flow cytometry system for sperm according to claim 42 wherein said sperm cells comprises sperm cells selected from a group consisting of mammal sperm cells, bovine sperm cells, equine sperm cells, porcine sperm cells, ovine sperm cells, camelid sperm cells, ruminant sperm cells, and canine sperm cells.

66. A flow cytometry system for sperm according to claim 42 wherein said nozzle comprises at least two nozzles.

67. A flow cytometry system for sperm according to claim 66 wherein said sperm cell collector is selected from the group consisting of multiple containers and a combined collector having a individual containers.

68. A flow cytometry system for sperm according to claim 67 and further comprising a number of selected containers less than a number of nozzles.

69. A flow cytometry system for sperm according to claim 42 wherein said pulsed laser is selected from a group consisting of Nd:YAG and Nd:YVO$_4$.

* * * * *